US007358230B2

(12) United States Patent
Alberts

(10) Patent No.: US 7,358,230 B2
(45) Date of Patent: Apr. 15, 2008

(54) CONSERVED DIAPHANOUS-RELATED FORMIN AUTOREGULATORY DOMAIN (DAD)

(75) Inventor: Arthur S. Alberts, Lowell, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 496 days.

(21) Appl. No.: 10/312,042

(22) PCT Filed: Jun. 22, 2001

(86) PCT No.: PCT/US01/20051

§ 371 (c)(1),
(2), (4) Date: Jul. 1, 2003

(87) PCT Pub. No.: WO01/98343

PCT Pub. Date: Dec. 27, 2001

(65) Prior Publication Data

US 2004/0072301 A1 Apr. 15, 2004

(51) Int. Cl.
| A61K 38/17 | (2006.01) |
| C07K 14/39 | (2006.01) |
| C07K 14/435 | (2006.01) |
| C07K 14/47 | (2006.01) |
| C07K 14/46 | (2006.01) |
| A61K 38/18 | (2006.01) |

(52) U.S. Cl. .............. 514/12; 514/13; 530/326
(58) Field of Classification Search .......... 530/326; 514/12, 13
See application file for complete search history.

(56) References Cited

U.S. PATENT DOCUMENTS 5,985,574 A * 11/1999 King et al. ............. 435/6
6,111,072 A * 8/2000 Narumiya et al. ......... 530/350

FOREIGN PATENT DOCUMENTS

WO WO 01 71042 A 9/2001

OTHER PUBLICATIONS

Alberts et al, Apr. 10, 1998, The Journal of Biological Chemistry, vol. 273, No. 15, pp. 8816-8622.*
Bowie, Science, 247: 1306-1310, 1990.*
Burgess et al, J. Cell Biology, 111: 2129-2138, 1990.*
Lazar et al, Molecular and Cellular Biology, 8: 1247-1252, 1988.*
Watanabe, N. et al. The EMBO Journal, 16(11): 3044-3056, 1997.*
Harris, S.D. et al. The EMBO Journal, 16(12): 3474-3483, 1997.*
Castrillon, D. H. et al. Development, 120: 3367-3377, 1994.*
Evangelista, M. et al., Science, 276: 118-122, 1997.*
Accession CAA96179 (MIPS, Database GenPept, NCBI, 1997.*
Accession No. AF094519, Tominaga, et al., Database GenBank, NCBI, 1998.*
Bione, S. et al, Am. J. Hum. Genet., 62: 533-541, 1998.*
Tominaga, T. , et al., "Diaphanous-Related Formins Bridge Rho GTPase and Src Tyrosine Kinase Signaling", Molecular Cell, vol. 5, No. 1, pp. 13-25, (Jan. 1, 2000).
Alberts, A.S., et al., "Analysis Of RhoA-Binding Proteins Reveals An Interaction Domain Conserved In Heterotrimeric G Protein Beta Subunits And The Yeast Response Regulator Protein Skn7", The Journal Of Biological Chemistry, vol. 273, No. 15, pp. 8616-8622, (Apr. 10, 1998).
Watanabe, N., et al., "Cooperation Between mDia1 And ROCK In Rho-Induced Actin Reorganization", Nature Cell Biology, vol. 1, No. 3, pp. 136-143, (Jul. 3, 1999).
Imamura, H., et al., "Bni1p And Bnr1p: Downstream Targets Of The Rho Family Small G-Proteins Which Interact With Profilin And Regulate Actin Cytoskeleton In *Saccharomyces cerevisiae*", The EMBO Journal, vol. 16, No. 10, pp. 2745-2755, (May 15, 1997).
Kawai, J., et al., "Functional Annotation Of A Full-Length Mouse cDNA Collection", Nature, vol. 409, No. 6821, pp. 685-690, (Feb. 8, 2001).
Alberts, A.S., "Identification Of A Carboxyl-Terminal Diaphanous-Related Formin Homology Protein Autoregulatory Domain", The Journal of Biological Chemistry, vol. 276, No. 4, (Jan. 26, 2001).

* cited by examiner

*Primary Examiner*—Alana M. Harris
*Assistant Examiner*—Anne L. Holleran
(74) *Attorney, Agent, or Firm*—Douglas H. Siegel; Price, Heneveld, Cooper, DeWitt & Litton, LLP

(57) ABSTRACT

The Diaphanousrelated formins (DRFs) constitute a subclass of FH proteins known for their ability to bind activated Rho subfamily of small GTP-binding proteins which link FH proteins to cellular signalling pathways. The present inventor has identified a new homology domain unique to the DRFs that termed the DRF-autoregulatory domain (DAD) in the extreme Cterminus. DAD is involved in intramolecular binding with the GTPase binding domain (GBD) of the DRFs. Disclosed herein are compositions and methods that can disrupt this binding, and cause changes in cells including actin polymerization and/or stabilization of actin fibers resulting in growth inhibition or cell death by apoptosis. A preferred composition is peptide or polypeptide of no more than about 130 amino acids comprising the DAD peptide having the amino acid sequence [GA]-[VA]-M-D-x-L-L-E-x-L-[KRQ]-x-[GA]-[SGA]-[AP] (wherein amino acids within a set of brackets are interchangeable and x means any amino acid). Fusion proteins comprising DAD are also disclosed as are nucleic acids and expression vectors encoding these peptides and proteins.

15 Claims, 21 Drawing Sheets

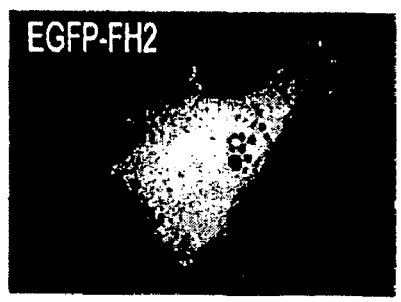 
FIG. 2A-1  FIG. 2A-2
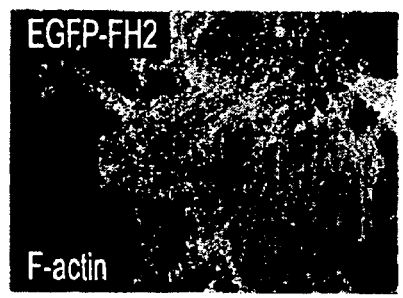 
FIG. 2A-3  FIG. 2A-4
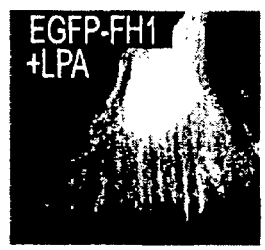  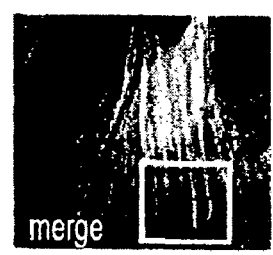
FIG. 2B-1  FIG. 2B-2  FIG. 2B-3
  
FIG. 2B-4  FIG. 2B-5  FIG. 2B-6

| pGAD (LEU) | mDia2 | GBD | FH1 | FH2 | DAD |
|---|---|---|---|---|---|
| pGBT9 (TRP) | 0 | 0 | 0 | 0 | 0 |
| Rho-V14S190 | 64 | 32 | 0 | 0 | 0 |
| DAD | 64 | 16 | 0 | 0 | 0 |
| SrcSH3 | 32 | 0 | 32 | 0 | 0 |
FIG. 3A
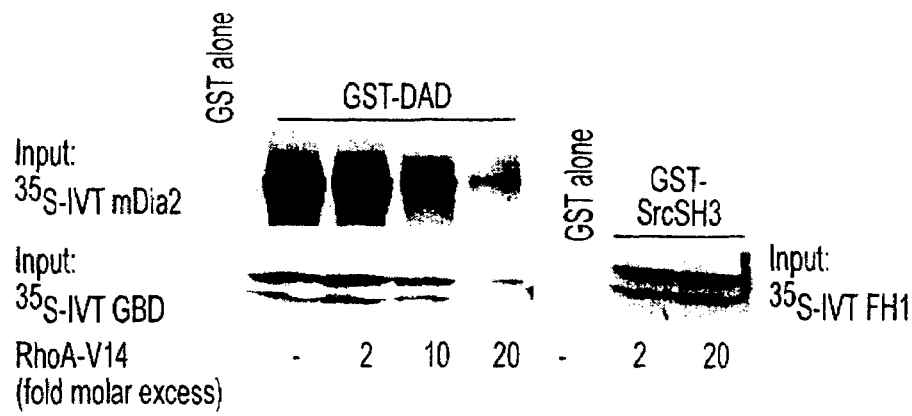
FIG. 3B
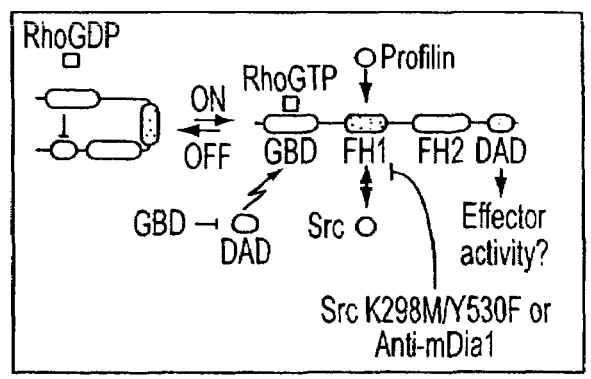
FIG. 3C

DAD

DAD

DAD

GBD
DAD

GBD
DAD

FH2
DAD

DAD

DAD+
Src K298M/Y530F

DAD+ anti-mDia1

ΔGBD-mDia2+
anti-mDia1

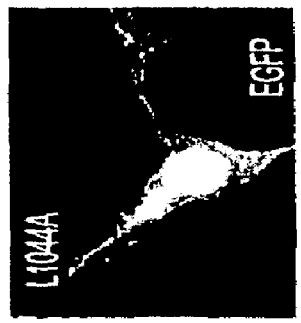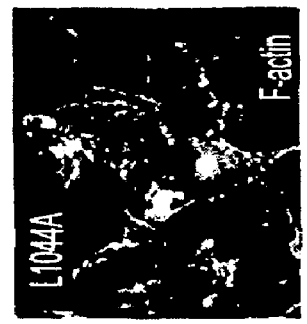

DAD: Dia-*autoregulatory* domain

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| mDia1 | D | E | T | G | V | M | D | S | L | L | E | A | L | Q | S | G | A | A | F | . | . | . | . | . | R | R | K | R | G |
| mDia3 | D | E | T | G | V | M | D | N | L | L | E | A | L | Q | S | G | A | A | F | . | . | R | D | R | R | K | R | I |
| mDia2 | D | E | T | G | V | M | D | S | L | L | E | A | L | Q | S | G | A | A | F | . | . | R | D | R | R | K | R | T |
| Diaphanous | T | Q | E | G | V | M | D | S | L | L | E | A | L | Q | T | G | S | A | F | G | Q | R | N | R | Q | A | R | R | Q | R | N |
| Bni1p | D | R | R | A | V | M | D | K | L | L | E | Q | L | K | N | A | G | P | A | K | S | D | P | . | S | S | A | R | K | R | A |
| SepA | A | T | S | G | A | M | D | S | L | L | E | K | L | R | A | A | P | Q | A | K | D | Q | . | R | D | R | R | R | A |

FIG. 6A

WASP (WH2) homology

| | | | | | | | | | | | | | | | | | | | | | | | | |
|---|---|---|---|---|---|---|---|---|---|---|---|---|---|---|---|---|---|---|---|---|---|---|---|---|
| WASP | G | R | G | A | L | L | D | Q | I | R | Q | G | I | Q | L | N | K | T | P | G | A | P | . | . . . |
| N-WASP | G | R | D | A | L | L | D | Q | I | R | Q | G | I | Q | L | K | S | V | A | D | G | Q | . . . . |
| WIP | G | R | N | A | L | L | S | D | I | S | K | G | K | K | L | K | K | T | V | D | . . . . . . |
| Cofilin | G | R | D | A | L | L | G | D | I | R | K | G | M | K | L | K | K | A | E | T | . . . . . . |
| Scar1 | A | R | S | V | L | L | E | A | I | R | K | G | I | Q | L | R | K | V | E | E | Q | R | E | . . . |
| mDia2 | V | M | D | S | L | L | E | A | L | Q | S | G | A | A | F | R | D | R | R | K | R | T | P | K | L . |
| mDia3 | V | M | D | N | L | L | E | A | L | Q | S | G | A | A | F | R | D | R | R | K | R | I | P | . . . |
| mDia1 | V | M | D | S | L | L | E | A | L | Q | S | G | A | A | F | R | . . | R | K | G | P | . . . |
| Diaphanous | V | M | D | S | L | L | E | A | L | Q | T | G | S | A | F | G | Q | R | N | R | Q | A | R | R | Q | R |
| Bni1p | V | M | D | K | L | L | E | Q | L | K | N | A | G | P | A | K | S | D | P | S | S | A | R | K | R | A |
| SepA | A | M | D | S | L | L | E | K | L | R | A | A | P | Q | A | K | D | Q | R | D | R | R | R | R | A | basic region

| | | | | | | | | | | | |
|---|---|---|---|---|---|---|---|---|---|---|---|
| H | V | M | Q | K | R | S | R | A | I | H | WASP |
| A | E | I | K | K | R | R | K | A | I | A | ActA |
| E | E | V | K | K | R | K | K | A | V | L | Cofilin |
| A | F | R | D | R | R | K | R | T | P | K | mDia2 |

15 mDia2 DAD

```
aa 1036  D E T G V M D S L L E A L Q S G A A F R D R R R R T P K L K D
                    1041    1044                1057      1060  1063  1065
         M1041A     L1044A
                    ↑
                    Induces ruffles
```

|           |         |
|-----------|---------|
| A         |         |
|    A      |         |
|           | A       R1057A |
|           |  A      R1058A |
|           |   A     R1059A |
|           |    A    R1060A |
|         A A         R1055A/D1056A |
|           E E       R1057E/R1058E |
|           E E       K1059E/R1060E |
|                 E E K1063E/K1065E |

FIG. 9A

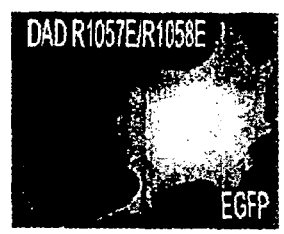
FIG. 9B-1    FIG. 9B-2    FIG. 9B-3
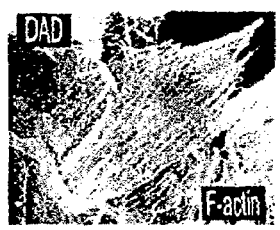
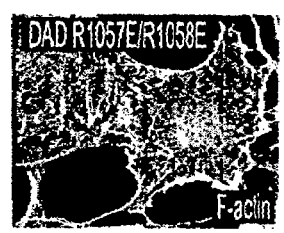
FIG. 9B-4    FIG. 9B-5    FIG. 9B-6
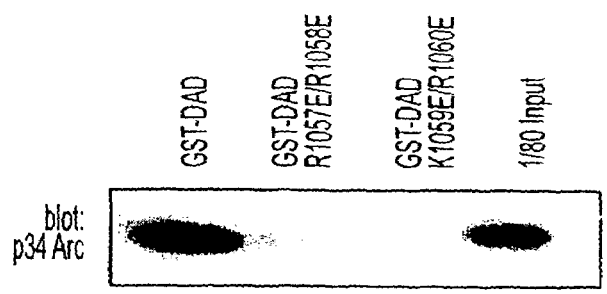
FIG. 9C

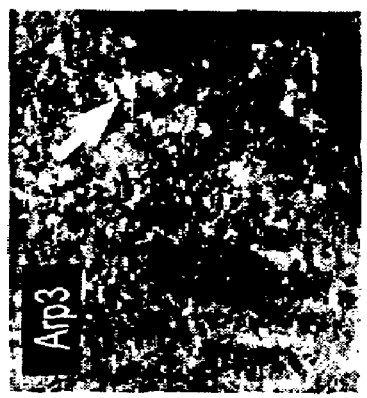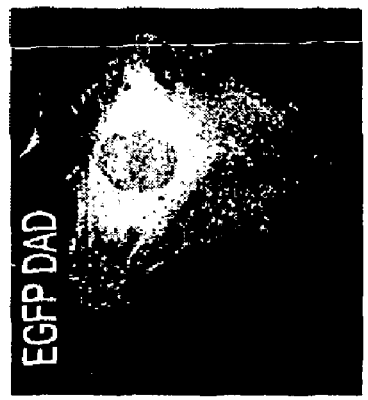

CONSERVED DIAPHANOUS-RELATED FORMIN AUTOREGULATORY DOMAIN (DAD)

BACKGROUND OF THE INVENTION

1. Field of the Invention

The present invention in the fields of molecular biology, biochemistry and medicine relates to novel protein domains involved in cytoskeletal events that are useful as a research tool and as inhibitors of cell growth, inducers of apoptosis and anticancer therapeutics.

2. Description of the Background Art

The recently discovered formin homology (FH) protein family participate in a range of actin-mediated processes affecting cell polarity and shape, including the in spatial and temporal coordination of cytokinesis. Substantial evidence indicates that FH proteins fulfil these functions by interacting, through distinct domains, with the actin-binding proteins profilin as well as the Arp2/3 complex and GTP-binding proteins of the Rho family.

The FH proteins were defined on the basis of conservation in sequence and protein organization among two *Drosophila melanogaster* proteins, DIAPHANOUS (DIA) and CAPPUCCINO (CAPU), a yeast protein, Bni1p, and a mouse protein, formin. Subsequently, additional genes encoding FH proteins have been found in fungi, plants, worms and mammals; there are now nearly a dozen characterized family members (Table 1). FH proteins are 1000 to 2000 amino acids in length and contain two conserved sequence domains, termed FH1 and FH2. FH1 domains average ~100 amino acids in length, and most are extremely proline rich, with multiple stretches of consecutive proline residues. FH2 domains are conserved regions of ~130 residues found only among members of the FH protein family.

The FH1 and FH2 domains in all family members are separated by ~160 aa, whereas the lengths of the flanking regions vary considerably. Blocks of sequence similarity within these variably sized regions have become recognizable as the number of known family members has increased. Sequence conservation has also been detected in regions surrounding the FH2 domain.

All of the FH proteins other than CAPU contain one or more coiled-coil regions, as predicted by the NEWCOILS and PAIRCOILS algorithms. Typically, one coiled-coil region lies N-terminal to the FH1 domain, and one or two lie within or C-terminal to the FH2 region. Coiled-coil domains are common among cytoskeletal proteins and provide the potential for homotypic and heterotypic interactions.

Database searches with a consensus FH2 domain indicate that eukaryotes contain multiple FH genes (Table 1). In *Saccharomyces cerevisiae*, for which a complete genome sequence is available, there are two recognizable FH genes (BNI1 and BNR1), whereas there are at least three in other species (e.g., sequences U40187, U88314 and Z78013 in *Caenorhabditis elegans*). Although the two FH genes in *S. cerevisiae* overlap in function, the same does not appear to be true for the pairs of genetically identified FH genes in flies and fission yeast.

TABLE 1

FH PROTEIN FAMILY MEMBERS

| Protein | Species | Cellular functions | Pairing partners[a] | Accession no. |
|---|---|---|---|---|
| Bni1p | S. cerevisiae | Cytokinesis; cell polarity | Profilin, Rho1p, Cdc42p, Bud6p/Alp3p | Z71547 |
| Bnr1p | S. cerevisiae | Cytokinesis; cell polarity | Profilin, Rho4p | Z47047 |
| cdc12 | S. pombe | Cytokinesis | Profilin | Z68136 |
| fus1 | S. pombe | Cell polarity | | L37838 |
| SepA | A. nidulans | Cytokinesis; cell polarity | | U83658 |
|  | A. thaliana | | | Z97338 |
| CYK1 | C. elegans | Cytokinesis | | U40187 |
| CAPU | D. melanogaster | Cell polarity | Profilin | U34258 |
| DIA | D. melanogaster | Cytokinesis | Profilin | U11288 |
| inDia | M. musculus | | Profilin, Rho | U96963 |
| hDIA | H. sapiens | | | |
| Formin | M. musculus | | WW motifs, SH3 domains | X62379 |

[a]Endogenous interactions with the pairing partners listed have been confirmed only for the yeast FH proteins.
[b]This Table is reproduced Table 1 of Wasserman, Trends in Cell Biology 8:111-115, 1998; cited reference numbers are those listed in the Wasserman publication.
Abbreviations: *A. nidulans*, *Aspergillus nidulans*; *A. thaliana*, *Arabidopsis thaliana*; CAPU, CAPPUCCINO; *C. elegans*, *Caenorhabditis elegans*; DIA, DIAPHANOUS; *D. melanogaster*, *Drosophila melanogaster*; FH, formin homology; *H. sapiens*, *Homo sapiens*; *M. musculus*, *Mus musculus*; *S. cerevisiae*, *Saccharomyces cerevisiae*; *S. pombe*, *Schizosaccharomyces pombe*; SH3, Srchomology 3.

The Diaphanousrelated formins (DRFs) constitute a subclass of FH proteins known for their ability to bind activated Rho subfamily of small GTP-binding proteins (Wasserman, S. *Trends in Cell Biol*, 1998, 8:111-115). Members of the Rho subfamily of GTP-binding proteins link FH proteins to cellular signalling pathways. Rho proteins, Ras-related GTPases, regulate cell adhesion, motility, bud-site selection and contractile processes (Takai, Y. et al. (1995) *Trends Biochem. Sci.* 20, 227-231; Narumiya, S. (1996) *J. Biochem.* 120, 215-228). The Rho subfamily includes the Rho, Rac and Cdc42 proteins, of which both Rho and Cdc42 are required for cytokinesis. It is these two proteins that interact with members of the FH family.

Ridley and Hall first demonstrated in 1992 that Rho small GTPase activation was both necessary and sufficient for the formation of actin stress fibers. Ridley, A. J. et al., *Cell* 70, 389-99 (1992a). Since then, two Rho GTPase bindimg proteins, Rho-kinase, or ROCK, and the Diaphanous-related Formin Homology proteins (DRFs) have been shown to be critical effectors in Rho-regulated actin remodeling (Ridley, A. J. *Nat Cell Biol* 1, E64-6 (1999)). Co-expression of activated variants of these two effectors are sufficient to recapitulate actin stress fibers caused by expression of activated RhoA (Kohno, H. et al., *EMBO J* 15, 6060-8 (1996); Watanabe, N. et al., *Nat. Cell Biol.* 1, 136-143 (1999); Nakano, K. et al., *Mol Cell* 5, 13-25 (2000); Tominaga, T. et al., *Mol Cell* 5, 13-25 (2000)). While ROCK has multiple substrates that participate in cytoskeletal remodeling, such as LIM kinase and the myosin-binding subunit (MBS) of myosin phosphatase (reviewed in Amano, M. et al., *Exp Cell Res* 261, 44-51 (2000)), none of the known DRF binding partners, including Src, IRSp53 and the actin-binding proteins, profilin, EF1α or Bud6p/Aip3p, appear to have a direct role in DRF-controlled actin remodeling (Watanabe, Y. et al., *Mol Cell Biol* 17, 2615-23 (1997); Umikawa, M. et al., *Oncogene* 16, 2011-6 (1998); Fujiwara, T. et al., *Biochem. Biophys. Res. Comm.* 271, 626-629 (2000); Ozaki-Kuroda, K. et al., *Mol Cell Biol* 21, 827-39 (2001); Suetsugu, S. et al., *Embo J* 17, 6516-26 (1998)). Instead, these factors likely have an obligatory role in targeting the Rho-regulated DRF complex to specific cellular regions or modulate DRF effects on the cytoskeleton.

In the budding yeast *Saccharomyces cerevisiae*, the DRFs include Bni1 and Bnr1 Evangelista, M. et al. (1997) *Science* 276, 118-122; Kohno, H. et al. (1996) *EMBO J.* 15, 6060-6068). Three mammalian DRF genes have been identified in mice/humans, respectively: mDia1/aNA1 Watanabe, N. et al. (1999) *Nature Cell Biol.* 1:136-143; Lynch, E. D. et al. (1997) *Science* 278, 1315-1318, mDia2/Dia2 (Alberts, A. S. et al., *Cell* 92, 475-487 (1998)), and mDia3/DIA (Bione, S. et al., *Am J Hum Genet* 62, 533-541 (1998)). mDia1 has been shown to bind activated RhoA-C and mDia2 binds RhoA, B and Cdc42 (Watanabe, N. et al., supra; Watanabe, N. et al. (1997) *EMBO J.* 16, 3044-3056). Based on primary amino acid sequence homology, the DRF family contains four conserved domains: the GTPase-binding domain (GBD) in the amino-terminus, three FH domains, the proline-rich FH1, FH2, and the FH3 domains (Petersen, J. et al., *J Cell Biol* 141, 1217-1228 (1998); Castrillon, D. H. et al. (1994) *Development* 120, 3367-3377). The present inventor has identified a new homology domain unique to the DRFs that termed the DRF-autoregulatory domain (DAD) in the extreme carboxyterminus that is described herein.

Studies in budding yeast showed that the DRFs are critical Rho effectors (Kohno et al., supra; Evangelista et al., supra). In mammalian cells, inhibition of the DRFs by microinjected antibodies showed that the DRFs are required for cytokinesis, stress fiber formation and activation of the transcription factor SRF (Tominaga, T et al., (2000) *Molec. Cell* 5:13-25). Expression of deregulated or 'activated' DRFs, created by removal of their GBD's, is sufficient to induce actin polymerization and gene expression in the absence of extracellular stimulation [Tominaga et al., supra; Watanabe. et al. (1999) supra; Evangelista et al., supra]. These activated mouse DRFs also cooperate with another small GTPase effector, Rhokinase or ROCK, to induce stress fibers in fibroblasts (Nakano, K. et al., *Mol Biol Cell* 10, 2481-2491 (1999); Tominaga et al., supra; Watanabe, N. et al., supra.).

The DRFs act as adaptor molecules in cells and bridge signaling and remodeling pathways by binding to several signaling kinases and scaffolding proteins via SH3 domain interactions with the proline-rich FH1 domain. These include Src non-receptor tyrosine kinase family (Kikyo, M. et al. *Oncogene* 18, 7046-7054 (1999)), Hoflp (Fujiwara, T. et al., *Biochem. Biophys. Res. Comm.* 271, 626-629 (2000)), DIP-1 (Chang, F. et al., *J Cell Biol* 137, 169-182 (1997)), and IRSp53/BAIAP2 (Watanabe et al., 1997, supra). The actin binding protein profilin also interacts with FH1 domains (Imamura, H. et al. *Embo J* 16, 2745-2755 (1997); Tominaga, T. et al. supra; Narumiya, S., et al., *FEBS Lett* 410, 68-72 (1997); Mikawa, M. et al., *Oncogene* 16, 2011-2016 (1998)). Other actin binding factors EF1α and Bud6p/Aip3p associate with Bni1p through other regions (Evangelista, M. et al., supra; Suetsugu, S., et al., *FEBS Lett* 457, 470-474 (1999)). The significance of profilin binding to the mammalian DRF family members has yet to be elucidated, as it does not appear to be an important factor in Rho-regulated actin remodeling (Sotiropoulos, A. et al., *Cell* 98, 159-169 (1999)). It may act, however, as an actin-monomer sensor in an SRF regulatory pathway (Kikyo, M. et al., supra; Nakano, K. et al., supra).

Bni1p, mDia1 and mDia2 have been shown to be 'activated' or deregulated by removal of their GTPase binding domains. Expression of □GBD-mDia1 and -mDia2 in fibroblasts activates SRF in the absence of extracellular stimulation in addition to cooperating with another small GTPase effector, Rho-kinase or ROCK, to induce stress fibers ((Watanabe, N. et al., 1999, supra; Kikyo et al., supra; Zhao, Z. S. et al., *Mol Cell Biol* 18, 2153-2163 (1998)). These truncation experiments suggested that the GTPase binding domain of the DRFs contained a negative regulatory activity. Many signaling molecules contain autoregulatory domains. For example, p21-activated kinase (PAK1)

Frost, J. A. et al., *J Biol Chem* 273, 28191-28198 (1998); Burbelo, P. D. et al., *J Biol Chem* 270, 29071-29074 (1995)) and Src-family kinases bear domains that modulate their activity through intramolecular associations (Kim, A. S. et al., *Nature* 404, 151-158 (2000)). The PAK1 autoinhibitory domain is adjacent to the CRIB domain (Welch, M. D., *Trends Cell Biol* 9, 423-427 (1999)); it is presumed that this association is regulated by binding to activated Cdc42.

A similar observation has been made for the Cdc42-binding Wiskott-Aldrich syndrome protein (WASP) (Alberts et al., supra). WASP is activated by the Rho-related small GTPase Cdc42 (Rohatgi, R. et al., *Cell* 97, 221-31 (1999); Ma, L. et al., *Proc Natl Acad Sci USA* 95, 15362-7 (1998); Kim, A. S. et al., *Nature* 404, 151-8 (2000)), the binding of which disrupts an intramolecular association between the GTPase binding domain (CRIB) (Burbelo, P. D. et al., *J Biol Chem* 270, 29071-4 (1995)) and the C-terminal WCA domain. Free WCA then binds actin monomers and activates Arp2/3 actin remodeling complex to induce filopodia, lamellipodia and rufile formation (Machesky, L. M. et al., *J Cell Biol* 146, 267-72 (1999); Mullins, R. D. et al., *Curr Opin Cell Biol* 12, 91-6 (2000)). The Arp2/3 complex is composed of p16, p20, p21, p34, p41, Arp2 and Arp3 (using the vertebrate nomenclature as per Mullins, R. D. et al., *Curr Opin Struct Biol* 9, 244-9 (1999)). Arp2/3 regulates the assembly of actin filaments at the leading edges of cells by both promoting the nucleation of new actin fibers as well as binding to pre-existing filaments and inducing branching. Actin branching is critical for the formation of lamellipodia (Pantaloni, D. et al., *Nat Cell Biol* 2, 385-91 (2000)) and p34 appears critical for this activity (Bailly, M. et al., *Curr Biol* 11, 620-5 (2001)). WASP and its relative, N-WASP, act with other proteins, such as the WASP-interacting protein (WIP) and the WASP-interacting SH3 protein (WISH), respectively, that modulate their activities in cells (Takenawa, T. et al., *J Cell Sci* 114, 1801-9 (2001); Martinez-Quiles, N. et al., *Nat Cell Biol* 3, 484-91 (2001); Fukuoka, M. et al., *J Cell Biol* 152, 471-82 (2001)).

SUMMARY OF THE INVENTION

The present invention is directed to a peptide or polypeptide of no more than about 130 amino acids comprising a peptide termed DAD having the amino acid sequence

[GA]-[VA]-M-D-x-L-L-E-x-L-[KRQ]-x-[GA]-[SGA]-[AP] (SEQ ID NO:1)

wherein amino acids within a set of brackets are interchangeable and x means any amino acid.

In one embodiment, a peptide consists essentially of the amino acid sequence

[GA]-[VA]-M-D-x-L-L-E-x-L-[KRQ]-x-[GA]-[SGA]-[AP] (SEQ ID NO:1)

wherein amino acids within a set of brackets are interchangeable and x means any amino acid.

The above peptide may further have at the C-terminus of SEQ ID NO:1, a basic motif of between about 5 and 12 amino acids.

In one embodiment, the above peptide or polypeptide includes an amino acid sequence selected from the group consisting of:

(a) GVMDSLLEALQSGAAFRRKRG [SEQ ID NO:2];
(b) GVMDSLLEALQSGAAFRDRRKRI [SEQ ID NO:3;]
(c) GVMDSLLEALQSGAAFRDRRKRT [SEQ ID NO:4];
(d) GVMDSLLEALQTGSAFGQRNRQARRQR [SEQ ID NO:5];
(e) AVMDKLLEQLKNAGPAKSDPSSARKRA [SEQ ID NO:6]; and
(f) GAMDSLLEKLRAAAPQAKDQRDRRRRA [SEQ ID NO:7];

Preferably, the above peptide or polypeptide is one in which its sequence is present in the mDia2 protein (SEQ ID NO:8).

In a preferred embodiment, the above peptide or polypeptide binds to the GTPase-binding domain (GBD) of Diaphanousrelated formin proteins.

Also provided is a fusion polypeptide comprising (a) a first peptide or polypeptide according to any of claims 1-6;
(b) optionally, a linker region; and
(c) a second polypeptide that is linked to the first peptide or polypeptide, or to the linker region, which second polypeptide is not natively linked to the first peptide or polypeptide.

In the above fusion polypeptide, the second polypeptide may be glutathione-S-transferase or a fluorescent protein such as GFP, YFP or BFP.

Another fusion polypeptide is a linear multimer of two or more repeats of monomers of the above peptide or polypeptide linked end to end, directly or with a linker present between the monomer repeats.

This polypeptide multimer may be of the formula $(P\text{-}X_m)_n\text{-}P$, wherein P is the peptide or polypeptide of any of claims 1-6, X is a spacer or linker selected form the group consisting of $C_1$-$C_{20}$ alkyl, $C_1$-$C_{20}$ alkenyl, $C_1$-$C_{20}$ alkynyl, $C_1$-$C_{20}$ polyether containing up to 9 oxygen atoms, and $Gly_z$, where z=1-10; m=0 or 1, and n=1-100.

The present invention is also directed to a nucleic acid molecule, preferably DNA which encodes any of the above peptides or polypeptides. In one embodiment, the nucleic acid has a sequence present in SEQ ID NO:9.

Also provided is a nucleic acid molecule that encodes the above fusion polypeptide.

The nucleic acid molecule, encoding a fusion polypeptide, may comprise:

(a) a first nucleic acid sequence encoding a first peptide or polypeptide as described above;
(b) optionally, fused in frame with the first nucleic acid sequence, a linker nucleic acid sequence encoding a linker peptide; and
(c) a second nucleic acid sequence that is linked in frame to the first nucleic acid sequence or to the linker nucleic acid sequence and that encodes a second polypeptide.

Also provided is a nucleic acid that hybridizes with any of the above nucleic acid molecules under standard stringent hybridization conditions. Preferred stringent conditions include incubation in 6× sodium chloride/sodium citrate (SSC) at about 45° C., followed by a wash in about 0.2×SSC at a temperature of about 50° C.

The invention is also directed to an expression vector comprising the above nucleic acid operatively linked to (a) a promoter and (b) optionally, additional regulatory sequences that regulate expression of the nucleic acid in a eukaryotic cell. Preferred expression vectors are plasmids or viral vectors.

Also provided is a cell transformed or transfected with a nucleic acid molecule as above, or with an expression vector as above, wherein the nucleic acid is expressed.

The present invention is also directed to a number of methods. A preferred method is for inhibiting cell growth or for killing a cell by apoptosis, comprising introducing into a cell in which actin polymerization and/or stabilization of actin fibers results in growth inhibition or cell death, the above peptide or polypeptide, such that the peptide or polypeptide causes the actin polymerization or the stabilization, thereby causing the growth inhibition of apoptosis.

The method for inhibiting cell growth or for killing a cell by apoptosis, may also comprise expressing in a cell in which actin polymerization and/or stabilization of actin fibers results in growth inhibition or cell death, the above nucleic acids, such that a peptide or polypeptide encoded by the nucleic acid is expressed and causes the actin polymerization or the stabilization, thereby causing the growth inhibition or apoptosis.

The above method may comprise expressing in a cell in which actin polymerization and/or stabilization of actin fibers results in growth inhibition or cell death, the above expression vector, such that a peptide or polypeptide encoded by the vector is expressed and causes the actin polymerization or the stabilization, thereby causing the growth inhibition or apoptosis.

The introducing or the expressing in these methods may be carried out in a live animal in vivo, preferably a human. Preferably, the cell being growth-inhibited or killed is a tumor cell.

In another embodiment, this invention provides a method to disrupt or inhibit the intramolecular binding of GBD to DAD in a cell, comprising introducing into the, or expressing in the cell, the above polypeptide or peptide, wherein the peptide or polypeptide disrupts or inhibits this GBD-DAD binding.

A preferred way to introduce the peptide is by microinjection. In other embodiments, nucleic acids may be introduced for expression by microinjection, transfection, transduction or infection of the cell with nucleic acid or vector.

Another method induces actin polymerization in a cell by providing to the cell an effective amount of the above peptide or polypeptide wherein the peptide or polypeptide induces actin polymerization. The providing may be achieved by microinjecting the peptide or polypeptide. A related method of inducing actin polymerization in a cell involves causing the expression in the cell of one of the above nucleic acids or expression vectors, wherein the peptide or polypeptide expressed from the nucleic acid induces actin polymerization.

Also provided is a method of stimulating Arp2/3 complex activation in a cell, comprising (1) providing to the cell an effective amount of the above peptide or polypeptide, for example, by microinjection, or (2) causing the expression in the cell of any of the above nucleic acids or expression vectors, such that the peptide or polypeptide expressed from the nucleic acid stimulates Arp2/3 complex activation.

BRIEF DESCRIPTION OF THE DRAWINGS

As shown in FIG. 1: DFNA1/mDia1 is SEQ ID NO:2; DIA156/mDia3 is SEQ ID NO:3; mDia2 is SEQ ID NO:4; Diaphonous is SEQ ID NO:5; Bni1 is SEQ ID NO:6; and SepA is SEQ ID NO:7.

FIG. 2A shows actin cytoskeletal changes following expression of EGFP-DAD fusion protein. Top panels display EGFP-fusion proteins and bottom panels the corresponding TRITC-phalloidin staining. Plasmids were injected at 10 ng/µl each; pEF$_m$EGFP-FH2 (mDia2 AA 801-910) and pEF$_m$EGFP-DAD (mDia2 AA 1031-1171) and fixed 3 h later. FIG. 2B shows that the FH1 domain targets EGFP to stress fibers. pEFmEGFP-FH1 (10 ng/µl, mDia2 AA 521-630) was injected into cells as described in FIG. 2A. 3 h after injection, cells were treated with 50 µM PLA. The top row shows a single LPA-treated cell with predominatly nuclear EGFP. The right panels show merged EGFP and TRITC-phalloidin. The bottom row shows imaged taken from the inset (white box) in the top row. FIG. 2C shows that DAD expression activates SRF-regulated gene expression. HA13 SRE-FosHA reporter cells were microinjected with the indicated expression plasmids. 3 h later they were fixed and stained for FosHA reporter by indirect immunofluorescence. Bars represent the mean percentage of EGFP-expressing cells staining positive for FosHA; error bars represent the standard deviation from 2-3 experiments where 40-100 EGPF positive cells were counted in each.

FIG. 3A shows results of a two-hybrid analysis. Yeast reporter strain HF7c was transformed with the indicated 'bait' (Trp$^-$) and 'prey' (Leu$^-$) plasmids before restreaking on selective plates (His) with increasing concentrations 3-aminotriazole (0, 2, 4, 8, 16, 32, and 64 mM) that selects for correlating expression of the HIS-reporter gene. The indicated numbers correspond to the highest concentration of 3-AT on which there was growth after 3 days. Both activated RhoA-V14S190 (GTPase deficient and CAAX mutation to prevent lipid modification) and DAD interacted with both mDia2 and the GBD but not other FH domains. FH1 binding to the SrcSH3 domain was used as a positive control for binding. The mDia2 plasmid encodes amino acids 47-800.

FIG. 3B shows that in vitro translated GBD and mDia2 bind GST-DAD. pT7-plink plasmids were used to generate $^{35}$S-methionine labeled GBD, FH1 and mDia2 by in vitro translation (IVT). IVT material was incubated with the GST-fusion proteins bound to agarose beads for 2 h at 4° C., warmed to 30° C. before addition of activated Rho. Beads were washed with cold binding buffer 3× before resuspension in SDS-sample buffer. Recombinant RhoA-V14 was introduced at 2-, 10- and 20-fold molar excess.

FIG. 3C presents a model describing an autoregulatory mechanism for the DRFs based on an intramolecular interaction between the GBD and DAD. Binding activated Rho-GTP disrupts the GBD-DAD interaction which allows either recruitment or activation of effector proteins to either FH1 or FH2 domains. Coexpression of the GBD would block the effects of DAD expression if DAD was an effector domain sufficient for actin remodeling and SRF activation. Interfering Src or anti-mDia1 would also not have an effect. If they did block, then DAD effects would be dependent upon endogenous DRFs and DAD would be springing the GBD from its intramolecular DAD interaction and would therefore activate the remaining molecule.

FIG. 4A shows that DAD induced actin rearrangements are blocked by GBD expression and interfering Src K298M/Y530F. pEF$_m$EGFP-DAD was injected with empty vector (pEF$_m$EGFP) or pEF$_m$-GBD, -FH2 or pSGT-Src K298M/Y530F, each 10 ng/µl, as indicated. Cells were fixed and stained with TRITC-phalloidin (bottom panels; EGFP-fusion shown in top panels). Both GBD and interfering Src block longitudinal induction of actin fibers.

FIG. 4B shows that GBD co-expression specifically blocks DAD activation of SRF. pEFmEGFP-DAD was coinjected with pEFm-GBD, FH1, FH2, PKN.N or C3 as indicated. Cells were fixed 3 h later for FosHA expression; bars represent the mean percentage of FosHA positive EGFP expressing cells. Error bars represent the standard deviation from 2-3 experiments.

FIG. 4C shows DAD inhibition by anti-mDia1, interfering Src and anti-Src. Anti-mDia1, Cst. 1 anti-Src or non-specific rabbit IgG (1 mg/ml each) were microinjected along with either pEFmEGFP-ΔGBD-mDia2 or pEFmEGFP-DAD. 3 h later cells were fixed and stained for FosHA expression. In these experiments (C), each cell was injected twice to ensure delivery of expression vector to the nucleus and antibody to the cytoplasm.

FIG. 4D shows representative fields of injected cells. SRE-FosHA reporter was detected by rabbit Y-11 anti-HA monitored by a secondary AMCA-coupled donkey anti-rabbit IgG antibody and green is EGFP.

FIG. 5A shows a mutational analysis of DAD-mDia2 interaction by two-hybrid assay. Alanine substitutions or stop codons were made for several of the conserved residues in the DAD core region and after the mDia2 basic stretch (RRKR). Mutations that affected binding are indicated by the closed black arrowheads, those that did not have an effect are indicated by the open arrowheads. In FIG. 5A, mDia2 is SEQ ID NO:10.

FIG. 5B shows expression of DAD mutants in cells. NIH 3T3 cells maintained on glass coverslips for 24 h in 0.1% FCS were microinjected with the indicated pEGFP-DAD or DAD variants (10 ng/µl). 3 h later, cells were fixed and stained with TRITC-phalloidin (shown in right hand panels). Mutation of conserved residues disrupted biological effects except for DAD-E1046A, which was still active.

FIG. 6a shows sequence comparisons. Dia-autoregulatory domain (DAD); black shading indicates identical residues and the conserved residues are highlighted with grey. FIG. 6b shows a comparison of WASP-WH2 and DAD sequences. ClustalW analysis was performed on the indicated peptide sequences from the WH2 domains: black boxes indicate identical residues, grey boxes with black lettering indicate conserved residues, and grey boxes with white letters indicate similar residues. Similar shading is used in the comparison of the basic regions. FIG. 6c is a series of photomicrographs showing that DAD induces de novo actin polymerization. Cells were injected with purified recombinant GST-DAD, -DAD M1041A, or GST alone, in addition to Alexa 568-labeled actin and fixed at the indicated times with formaldehyde. Coverslips were then mounted in gelvatol and visualized with a 100× objective and images acquired with a CCD camera as described in Example VI. In FIG. 6a, mDia1 is SEQ ID NO:2; mDia3 is SEQ ID NO:3; mDia2 is SEQ ID NO:4; Diaphanous is SEQ ID NO:11; Bni1p is SEQ ID NO:6; and SepA is SEQ ID NO:7. In FIG. 6b (section entitled "WASP (Wh2) homology"): WASP, N-WASP, WIP, Cofilin. Scarl, mDia2, mDia3, mDia1, Diaphanous, Bni1p, and SepA are SEQ ID NOS: 12-22, respectively. In FIG. 6b (section entitled "basic region"), WASP, ActA, Cofilin, and mDia2 are SEQ ID NOS:23-26, respectively.

FIG. 7a shows the Interaction of GST-tagged DAD with purified G-actin. Recombinant GST-tagged DAD and GST (20 µg) bound to glutathione-sepharose beads were incubated with 1 µg of G-actin. The resulting protein complexes were precipitated, washed, separated by SDS-PAGE, transferred to membranes prior to immunoblotting with anti-actin antibody. FIG. 7b shows the interaction of recombinant DAD protein with purified Arp2/3 complex. Recombinant GST-tagged DAD and GST (20 µg) were incubated with 1 µg of purified Arp2/3 complex. The resulting protein complexes were precipitated with glutathione-sepharose and immunoblotted with anti-Arp3 and anti-p34 antibodies. FIG. 7c shows the presence of DAD complexes with Arp2/3 from NIH 3T3 cell lysates. NIH 3T3 cells growing in 10% FCS were lysed in buffer containing 1% (v/v) Triton X-100 and the resulting extracts were incubated with the indicated GST-fusion proteins complexed to sepharose beads. Complexes were analyzed as in FIGS. 7a and b.

FIGS. 9a-9c show that the basic regions is required for thin fiber formation and association with Arp2/3. FIG. 9a shows a mutational analysis of mDia2 DAD basic region; open letters indicate amino-acid substitutions that inhibited DAD activity, except for DAD L1044A which induces the formation of actin ruffles (See Examples). The positions of the substitutions are shown on the right. Glutamate substitutions within the basic region disrupted DAD induction of thin fibers. FIG. 9b shows representative images of EGFP-DAD, -DAD R1057A, and -DAD R1057E/R1058E expressing cells 3 hrs after injection of their respective expression plasmids. FIG. 9c shows results of GST-'pull down' experiments from NIH 3T3 cell lysates. 15 µg of the indicated fusion protein was incubated with lysates as in FIG. 7a-7c. Bound material was detected after extensive washing and immunoblotting with anti-p34 Arc. In FIG. 9a, mDia2 DAD is SEQ ID NO. 27.

DESCRIPTION OF THE PREFERRED EMBODIMENTS

Figure 1:
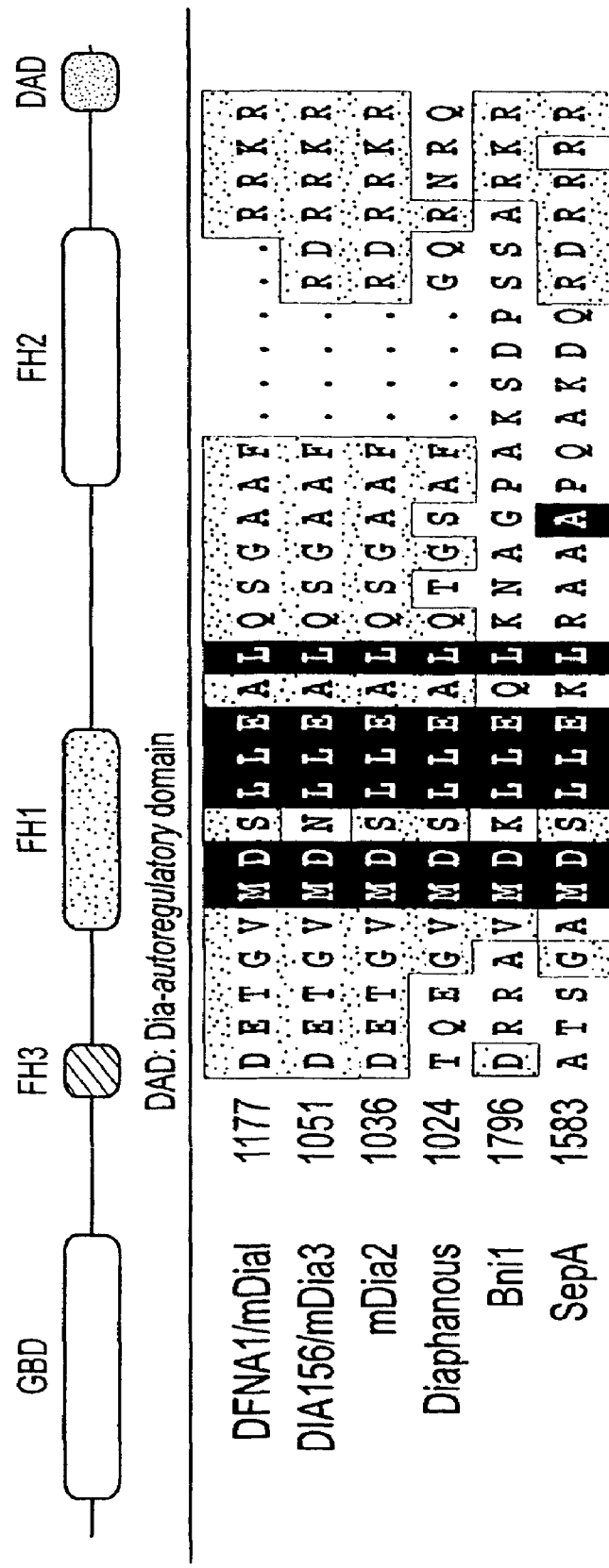
FIG. 1. A conserved C-terminal domain in the Diaphanous-related FH protein subfamily. Comparative alignments of mouse DRFs mDia1, mDia3, and mDia2 with *Drosophila melanogaster* Diaphanous, *Saccharomyces cerevisiae* Bni1p and *Aspergillus nidulans* SepA. Numbers in the second column correspond to the first residue shown from each respective sequence (Accession no. provided in Methods section). Identical residues are blue, similar amino acids are green; a consensus sequence can be describe by [GA]-[VA]-M-D-x-L-L-E-x-L-[KRQ]-x-[GA]-[SGA]-[AP] where x represents any residue; underline indicates a conserved region of basic residues.
Figures 1, 4A:
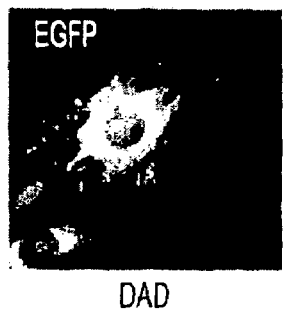
FIGS. 4A, 4B, 4C and 4D: Disruption of DAD effects by GBD squelching and by inhibition of endogenous DRF (mDia1).
Figures 2, 4A:
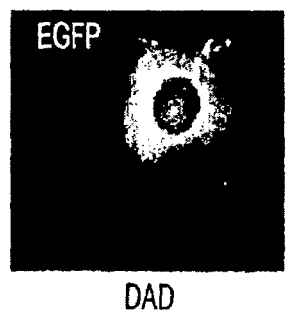
Figures 3, 4A:
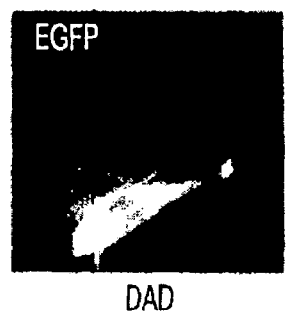
Figures 4, 4A:
Figures 4, 4A, 5:
Figures 4, 4A, 5, 6:

Amino acid sequence alignments of the complete FH protein superfamily delineate the proline-rich FH1 and FH2 regions of homology. Alignment of only the DRF subfamily, that binds Rho family small GTPases, yields a conserved domain in the C-termini that is shown in FIGS. 1 and 6 (and panels thereof given alphabetical labels).

DAD is described by the consensus sequence
[GA]-[VA]-M-D-x-L-L-E-x-L-[KRQ]-x-[GA]-[SGA]-[AP] (SEQ ID NO:1)

wherein amino acids (single letter code) within brackets are interchangeable and "X" means any amino acid.

The DAD domain is found in all the three mouse/human DRFs discovered thus far, in *Drosophila melanogaster* diaphanous (Dia), budding yeast *S. cerevisiae* Bni1 protein and *Emericella nidulans* SepA proteins. This is shown in the list below and in FIGS. 1 and 6. In the list below, identical amino acids are shaded.

```
DIA156/mDia3
1051    DETGVMDNLLEALQSGAAF....RDRRKRI    [SEQ ID NO:3]

mDia2
1036    DETGVMDSLLEALQSGAAF....RDRRKRT    [SEQ ID NO:4]

Dia
1024    TQEGVMDSLLEALQTGSAFGQRNRQARRQR    [SEQ ID NO:5]

Bni1
1796    DRRAVMDKLLEQLKNAGPAKSDPSSARKRA    [SEQ ID NO:6]

SepA
1583    ATSGAMDSLLEKLRAAAPQAKDQRDRRRRA    [SEQ ID NO:7]
```

The DAD peptide sequence begins at the fourth residue (G in most of the above). The number in the second column is the beginnin residue number of the indicated peptide in the full length protein. GenBank TM/EBI accession numbers for the gene products of the proteins listed above are: mDia1-

U96963; mDia2-AF094519; DIA156-NP006720; Diaphanous-AAA67715; Bni1, P41832; and SepA-AAB63335. The Swiss-Prot accession numbers are: mDia1—O08808; mDia2-Q9Z207

The complete amino acid sequence of mDia2 is shown below, with the sequence corresponding to DAD (shown above) underlined and the basic motif double underlined:

```
                                                              (SEQ ID NO:8)
   1 MERHRARALG RDSKSSRRKG LQSAPPAGPY EPGEKRPKLH LNIRTLTDDM LDKFASIRIP
  61 GSKKERPPLP HLKTVSGISD SSSLSSETME NNPKALPESE VLKLFEKMME DMNLNEDKKA
 121 PLREKDFGTK KEMVMQYINT ASKTGSLRSS RQISPQEFLH ELKMGYTDER LFTYLESLRV
 181 SLTSHPVSWV QSFGHEGLGL LLDILEKLIN GQIQEKVVKK TQHKVIQCLR ALMNTQYGLE
 241 RIMSDKRSLS LLAKAMDPRQ PAMMADVVKL LSAVCIVGEE SILEEVLEAL TSAGEERKID
 301 RFFSIVEGLR HNSVNLQVAC MQLINALVTS PDDLDFRLHL RNEFMRCGLK EILPNLKGIK
 361 NDGLDIQLKV FDEHKEEDLS EFFHRLEDIR AELDEASDVY SMLWDTVKET RAEGHFLSIL
 421 QHLLLIRNDR FIREQYFKLI DECVSQIVLH RDGTDPDFTY RKRLDLDLSQ FVDVCIDQAK
 481 LDEWEEKASE HCKKFEKECT DHQETQAQLQ KREAKINELQ AELQAFKSQF GALPPGTKIP
 541 LQPSVEGEAG PSALPPAPPA LSGGVPPPPP PPPPPPPPLP GMPMPFGGPV PPPPPLGFLG
 601 GQSSIPLNLP FGLKPKKEFK PEISMRRLNW LKIGPNEMSE NCFWIKVNEN KYENRDLLCK
 661 LENTFCCQEK EKRNTNDFDE KKVIKKRMKE LKFLDPKIAQ NLSIFLSSFR VPYEKIRTMI
 721 LEVDETQLSE SMIQNLIKLI PDEEQLKSLS QFRSDYNSLC EPEQFAVVMS NVKRLRPRLS
 781 AILFKLQFEE QVNNIKPDIM AVSTACEEIK KSKGFSKLLE LVLLMGNYMN AGSRNAQTFG
 841 FDLSSLCKLK DTKSADQKTT LLHFLVDVCE EKHADILHFV DDLAHLDKAS RVSVEMLEKN
 901 VKQMGRQLQQ LEKNLETFPP PEDLHDKFVI KMSSFVISAN EQYEKLSTLL GSMTQLYQSI
 961 MGYYAVDMKK VSVEEFFNDL NNFRTSFMLA LKENIKKREA AEKEKRARIA KERAEKERLE
1021 RQQEKKRLLE MKTEGDETGV MDSLLEALQS GAAFRDRRKR TPKLKDIRQS LSPMSQRPVL
1081 KVCNHENQKM QLTEGSRPHH SINCNSTRTP VAKELNYNLD THASTGRIKA VEKEACNAES
1141 NKKKEMELLG SVAKSESVPE VEALLARLRA L
```

The nucleic acid sequence of mDia2 that encodes SEQ ID NO:8 is shown below:

```
                                                               SEQ ID NO:9
   1 atggagaggc accgggcgcg cgctctcggc cgggacagca gtcgtcgcg gaggaagggc
  61 ttgcagtccg cgccgcccgc tggcccctac gagcccgggg agaagcgacc caagttgcat
 121 ttaaatatta gaacactgac agatgatatg ctggacaaat tgccagtat aagaattcca
 181 gggagcaaga aagagagacc tcccttccc cacctgaaga ctgtgtctgg gatcagtgac
 241 agctcatcac tgtcctcaga gacaatggaa aacaacccaa aggcgctgcc agagagtgaa
 301 gtcttgaagc tttttgagaa gatgatggaa gatatgaatt taaatgaaga taaaaaggca
 361 ccattgcggg aaaaagactt cggtatcaaa aagaaatgg tgatgcagta cattaatact
 421 gcttctaaga caggaagtct tagaagtagc cgacagatct cacctcagga atttctccat
 481 gagctgaaaa tgggttacac agacgagaga cttttcacgt atctggagtc actccgagta
 541 tcattgacca gtcatcctgt gagttgggtg caaagctttg gacacgaggg actcggatta
 601 ttgctggaca ttttggaaaa actaattaat gggcaaatcc aagaaaaagt tgtgaagaag
 661 actcagcaca aagtcatcca gtgtctgaga gccctgatga acacacagta tggcttagaa
 721 aggattatga gtgacaagag gagtctttcc ttgttggcaa aagccatgga tcccaggcag
```

-continued

```
 781 cccgctatga tggcagacgt ggtgaagctt ctgtctgcag tgtgcattgt cggcgaggaa
 841 agcatccttg aagaagtgtt agaagccttg acttcagctg gagaagaaag aaagattgac
 901 agatttttt ccattgtgga aggcctccgg cataactcag tgaacctgca agttgcttgt
 961 atgcagctca taaatgctct cgttacatct cctgatgatt tggacttcag gcttcacctc
1021 agaaatgaat ttatgcgttg tggattgaaa gagatattgc caaacttaaa gggcattaag
1081 aatgatggcc tggatataca acttaaagtc tttgatgagc acaaagaaga agatttgagt
1141 gagttttcc atcgccttga agacattaga gctgaacttg atgaagcatc tgatgtttac
1201 agcatgttat gggacacagt taaggaaact cgagcagagg gacattttct ttctattctt
1261 cagcatctcc tgctcattcg caatgatcgt tttataagag agcagtattt caaattaatt
1321 gatgagtgtg tgtcacagat tgtattacat agagatggaa cggaccctga cttcacatac
1381 agaaaaagac tagatttgga cttaagtcag tttgtagatg tttgcataga tcaggccaaa
1441 ctagatgagt gggaagagaa agcatccgaa cattgcaaga aatttgaaaa agagtgtact
1501 gaccaccaag aaacccaggc tcaattgcag aaaagagagg caaagattaa tgagcttcaa
1561 gcagagttac aagcttttaa atcccagttt ggtgccttgc cacctggtac aaaaattcct
1621 ttgcaacctt cagtagaagg tgaagctggc ccttcagccc ttcctcctgc cccaccagca
1681 ctcagtggag gagtgccgcc tcccccaccg ccccctcctc caccaccccc accactccca
1741 ggaatgccaa tgccatttgg tggccctgta ccaccaccac ctcctctggg attcctgggt
1801 gggcaaagct ctattccatt aaacctgcca tttggtttga aaccaaagaa agaatttaag
1861 cctgaaatca gcatgagaag attgaattgg ttaaagatcg gaccaaatga aatgtctgag
1921 aactgcttct ggatcaaagt aaatgaaaat aagtatgaaa atagggattt gctttgtaaa
1981 cttgagaaca ctttttgttg ccaagaaaaa gagaaaagga atacaaatga ctttgatgag
2041 aagaaagtta ttaagaagag aatgaaggaa cttaaatttc tagatcctaa aattgctcag
2101 aacctttcaa tcttcctgag ctccttccgg gtgccatatg agaaaatcag gacgatgata
2161 ttggaagtgg atgaaacaca gttgtcagag tccatgattc agaacttaat aaagcacctt
2221 cctgatgagg agcagttgaa gtcattgtcc cagtttagaa gtgactataa cagtttgtgt
2281 gagcctgagc agttcgctgt tgtgatgagc aatgtgaaga gactccggcc acggctcagt
2341 gctattctct ttaagcttca atttgaagag caggtgaaca acatcaaacc tgacatcatg
2401 gctgtcagta ctgcctgcga ggagatcaag aagagcaaag gctttagcaa gttgctggaa
2461 cttgtgttgc taatgggaaa ctacatgaat gctggctccc ggaatgctca aaccttcgga
2521 tttgacctta gctctctctg taaactgaag gatacaaaat ctgcagatca gaaaaccaca
2581 ctcctccatt tcctggtaga tgtatgtgaa gaaaagcatg ctgcatcct tcactttgtg
2641 gacgatttgg cacatttaga caaagctagc agagtctctg tagaaatgct ggaaaagaac
2701 gtgaagcaga tgggaaggca gcttcaacag cttgagaaga atttggaaac cttcccccct
2761 cctgaggact gcatgacaa gtttgtgata aagatgtcca gcttcgttat cagtgcgaac
2821 gagcagtatg aaaaactctc cacactactg ggcagcatga cacaattgta ccagagtata
2881 atgggctact atgctgtcga catgaagaag gtttccgtgg aagagttttt taatgatctg
2941 aacaacttca gaacttcatt tatgctagca ttaaaggaaa acatcaaaaa acgagaagca
3001 gcagaaaagg agaaacgtgc caggatagcg aaagagcgag cagagaaaga gcgacttgaa
3061 cgccagcaag agaaaaagcg cttactagaa atgaaaactg agggagatga dacaggagtg
3121 atggatagtc tgctggaggc cttgcagtca ggggctgcct tccgcgacag aagaaaaagg
```

-continued

```
3181  acaccaaagc  tgaaagatat  tcggcagagt  ctcagcccga  tgtctcagag  gcctgttctc 3241  aaagtttgta  accatgaaaa  tcagaaaatg  cagttgacag  aagggtcacg  tccacaccac 3301  agtatcaatt  gcaactccac  caggactcca  gtcgccaagg  agcttaatta  taatctagac 3361  actcatgcgt  ctacagggag  gatcaaggca  gttgagaagg  aagcctgtaa  tgcagaaagc 3421  aacaaaaaaa  aggaaatgga  acttcttggc  tctgttgcta  aaagcgaatc  agttcctgaa 3481  gttgaagccc  tgctggcaag  attacgagct  ttataa
```

Interestingly, the DFNA1 mutation occurs eight residues away from the DAD domain, where a frameshift introduces a stop codon that truncates DFNA1 protein at amino acid 1196 (Lynch et al. supra)

DAD expression in cells is sufficient to activate actin polymerization, stabilize microtubules and transcription regulated by the serum response factor.

The present inventor has defined a mechanism by which DAD peptide activates actin polymerization. DAD represents an intramolecular regulatory domain of the DRF proteins. In unstimulated cells, it binds to the GBD of the DRFs. Upon stimulation of cells with agonists that activate Rho proteins, Rho then binds to the GBD and disrupts the negative GBD-DAD intramolecular interaction. DRF proteins then either activate or recruit other cellular factors that trigger changes in the cytoskeleton.

The present invention defines a regulatory mechanism for the Diaphanous-related FH protein subfamily. The DRFs are regulated by intramolecular GBD-DAD binding. Rho-GTP activates the DRFs disrupting GBD-DAD interaction. DAD expression mimics Rho-GTP binding by interfering with normal autoregulation of cellular DRFs. The DAD structure is highly conserved and its characterization further explains the nature of several prior observations: truncation of Bni1, mDia1 and mDia2 GTPase binding domains resulted in their activation. DAD-GBD autoregulation is analogous to the interaction of the GBD of WASP (the CRIB domain) and the VCA domain. Unlike the VCA domain however, the DAD does not contain 'effector' activity. Instead, the potent effects of DAD expression are dependent upon the endogenous complement of mDia1 (e.g., in NIH 3T3 cells which weere studied).

Similar to the WASP autoinhibition mechanism, the GBD of the DRFs is a bi-functional domain that senses activated Rho GTPase and governs the activity of the scaffold protein through its association with DAD. Effector loop mutations of Rho have shown that The interaction of Rho with mDia2 is complex based on analysis of effector loop mutations of Rho (Hill, C. S. et al., Cell 81, 1159-1170 (1995)). Also, several of the Rho binding proteins, including PKN and kinectin, bear multiple binding sites for activated GTPases and cannot be restricted to a limited peptide domain.

Introduction of DAD peptide in cells (by microinjection or other means of transfection, transduction or infection), like activated Rho, disrupts the intramolecular GBD-DAD interaction in trans by preferentially displacing the GBD.

Deletion of the GBD 'activates' the DRFs. In budding yeast, ΔGBD-Bni1 expression causes the formation of actin cables. Depending on the cell growth conditions, and thereby, the levels of activated Rho and ROCK activity, activated ΔGBD-mDia1 or mDia2 expression in mammalian cells causes actin stress fiber formation. Once the GBD-DAD interaction was confirmed (Example II), a simple model was conceived to explain the effects of DAD domain expression in cells. The model is shown in FIG. 3C and expanded in FIG. 11: In cells with low levels of activated Rho-GTP, the DRFs assume an inactive state with the C-terminus interacting directly with the N-terminus. Upon the induction of cells in which guanine nucleotide exchange is activated and following loading of Rho with GTP, cells preferentially expose domains necessary for the recruitment or activation of downstream effectors through FH1 and FH2 domains. The model also accounts for the possibility that the C-terminal DAD domain also maintains effector activity in a manner similar to the VCA region of WASP Overexpression of the GBD will squelch the effects of DAD domain expression. To address this, plasmids encoding both GBD and DAD domains were microinjected into cells and stress fiber and SRF activity were monitored (see EXAMPLES).

The model also predicted that the effects of DAD expression were due to the inhibition of intramolecular DAD-GBD interaction. Therefore, DAD domain expression would activate endogenous DRF proteins. This possibility was tested by inhibiting endogenous mDia1, which is expressed in NIH3T3 cells (Tominaga et al., supra), by co-injection of anti-mDia1 antibody with the expression vector for EGFP-DAD. (EXAMPLE III)

DAD has Utility as a Research Tool

To date, there are no specific compounds that activate actin polymerization. DAD can be introduced into cells as art expressed mini-gene or as a peptide, it will provide investigators a unique tool to study both cell signaling, structure and physiology. DAD may be coupled to other peptides such as those derived from HIV tat, antennapedia, or the anthrax lethal factor complex, that promote its entry into cells.

DAD expression plasmids or DAD peptides produced using conventional methods and compositions, can be used as reagents that induce actin polymerization in multiple organism and cell types. DAD induced cells are used in a screening assay for compounds that disrupt actin polymerization and the cytoskeleton.

In general, then, the DAD peptide is a useful biological tool to study Rho signaling and cytoskeletal regulation pathways.

DAD-GBD Interaction as a Reporter for Intracellular Activation of Small GTPases

The DAD-GBD interaction is disrupted by binding to activated Rho. Therefore DAD and, independently, the GBD from the DRF mDia2 (or its human homologue), are fused to commercially available fluorescent proteins such as yellow and cyan mutants of Green fluorescent protein (GFP) (e.g., EYFP and EBFP) and expressed in cells or in mice as transgenes. Using fluorescence resonance energy transfer (FRET), the interactions of these polypeptides in unstimulated cells is measured. (See, for example: Tsien R Y, A. J. Physiol. 1992, 263(4 Pt 1): C723-8; Matyus L. J Photochem Photobiol B. 1992, 12:323-37; Mitra R D et al., Gene. 1996, 173:13-17; Lankiewicz L et al., Acta Biochim Pol. 1997, 44(3): 477-89; Tsien R Y, Annu Rev Biochem. 1998;67:509-44; Pollok B A et al., Trends Cell Biol. 1999, 9(2): 57-60; Bastiaens P I et al., Trends Cell Biol. 1999, (2): 48-52; Periasamy A et al., Methods Cell Biol. 1999; 58:293-314; Zacharias DA et al., Curr Opin Neurobiol. 2000, 10:416-21; Llopis J et al., Proc Natl Acad Sci USA 2000, 97:4363-8; Honda A et al., Proc Natl Acad Sci USA, 2001 98:2437-2442.

DAD-GBD FRET technology represents a novel in vivo model for testing the biochemical activity of small GTPases for their effects on the DAD-GBD interaction. This approach can be applied to other GTPase binding proteins as potential specific in vivo DAD Can Serve as an Inducer of Apoptosis and an Anti-Cancer Agent DRFs have a role in the formation of stable microtubules in mammalian cells. The present invention supports a role for the FH proteins in the regulation of microtubule dynamics. DAD or DAD-derived peptides might have another important use: extended DAD expression induces programmed cell death. Similar observations have been made with treatment of cells with Taxol (paclitaxel), a compound that also stabilizes microtubules (Maldonado, V. et al., *J Biochem Toxicol* 11, 183-188 (1996)). The ability of Taxol and DAD to trigger apoptosis is believed to be mediated through the disruption of normal cytoskeletal dynamics. Cytoskeletal disruption can lead indirectly to alterations in signaling and gene expression that trigger apoptosis. Like Taxol (Dumontet, C. et al., *J Clin Oncol* 17, 1061-1070 (1999), derivatives of the DAD are useful anti-tumor agents.

The compositions and methods described herein are useful for inhibiting the growth of, and for killing, by apoptosis, any type of cell in vitro and in vivo where actin polymerization and stabilization of actin fibers in cells would result in growth inhibition and/or cell death. Thus, the invention is particularly useful for the treatment of a tumor in an animal.

Administration of DNA or a vector or other vehicle containing the DNA, as in the gene therapy embodiments described herein, is performed using any of a number of routes, depending on the location of the cells being targeted. Thus, administration may be by any parenteral route, including but not limited to intramuscular, subcutaneous or transdermal, intravenous (including into the portal circulation), intrathecal, intraperitoneal, intragastric and by inhalation or instillation into the lungs. Oral administration of certain of the delivery vehicles disclosed herein is also known in the art.

An effective amount or dose of (a) DAD peptide or a functional derivative for inhibiting growth or inducing death of a cell s in the range of about 0.01 femtogram to about 1 picogram per cell. Effective doses may be determined, preferably by injecting cells in vitro, in order to identify the optimal dose range using various of the methods described herein. The dosage administered will in part be dependent upon the health and weight of the recipient, the existence of other concurrent treatment, if any, frequency of treatment, and the nature of the effect desired, for example, eradication of a tumor or treatment of autoimmunity.

Amino Acid Substitution and Addition Variants of DAD

Also included in this invention are DAD peptides in which at least one amino acid residue and preferably, only one, has been removed and a different residue inserted in its place. Preferably such substitution and addition results in improved biological activity or improved clinical properties without significantly diminishing the desired biological or biochemical effect. It is within the skill in the art to assess whether a proposed substitution or addition of one or more residues will have the desired impact on the peptide. For a detailed description of protein chemistry and structure, see Schulz, G. E. et al., *Principles of Protein Structure*, Springer-Verlag, New York, 1979, and Creighton, T. E., *Proteins: Structure and Molecular Principles*, W.H. Freeman & Co., San Francisco, 1984, which are hereby incorporated by reference. The types of substitutions which may be made in the peptide molecule of the present invention are conservative substitutions and are defined herein as exchanges within one of the following groups:

1. Small aliphatic, nonpolar or slightly polar residues: e.g., Ala, Ser, Thr, Gly;
2. Polar, negatively charged residues and their amides: e.g., Asp, Asn, Glu, Gln;
3. Polar, positively charged residues: e.g., His, Arg, Lys;

Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Most substitutions according to the present invention are those which do not produce radical changes in the characteristics of the peptide molecule. Even when it is difficult to predict the exact effect of a substitution in advance of doing so, one skilled in the art will appreciate that the effect can be evaluated by routine screening assays, preferably the biological and biochemical assays described herein. Modifications of peptide properties including redox or thermal stability, hydrophobicity, susceptibility to proteolytic degradation or the tendency to aggregate with carriers or into multimers are assayed by methods well known to the ordinarily skilled artisan.

Chemical Derivatives of DAD

"Chemical derivatives" of DAD contain additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Capped peptides discussed below are examples of preferred chemical derivatives of a "natural" uncapped peptide. Any of the present combination of substitution or addition variants may be capped with any of the capping groups disclosed herein.

Other examples of chemical derivatives of the peptide follow.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing □-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79-86), acetylation of the N-terminal amine, and amidation of the C-terminal carboxyl groups.

For every peptide sequence disclosed herein, this invention includes the corresponding retro-inverso sequence wherein the direction of the peptide chain has been inverted and wherein all the amino acids belong to the D-series. The complete range of N-terminal capping groups and the complete range C-terminal capping groups specified for the L-series peptides are also intended for the D-series peptides.

Also included are peptides wherein one or more D-amino acids has/have been substituted for one or more L-amino acids. Additionally, modified amino acids or chemical derivatives of amino acids may be provided such that the peptide contains additional chemical moieties or modified amino acids not normally a part of a natural protein. Such derivatized moieties may improve the solubility, absorption, biological half life, and the like. Moieties capable of mediating such effects are disclosed, for example, in *Remington's Pharmaceutical Sciences,* 16th ed., Mack Publishing Co., Easton, Pa. (1980).

Multimeric Peptides

The present invention also includes longer peptides in which the basic peptidic sequence of DAD is repeated from about two to about 100 times, with or without intervening spacers or linkers. A multimer of the peptide SEQ ID NO:1 (referred to symbolically in this section as DAD (where D, A and D do not represent single amino acids) is shown by the following formula (DAD-$X_m$)$_n$-DAD wherein m=0 or 1, n=1-100. X is a spacer group, preferably $C_1$-$C_{20}$ alkyl, $C_1$-$C_{20}$ alkenyl, $C_1$-$C_{20}$ alkynyl, $C_1$-$C_{20}$ polyether containing up to 9 oxygen atoms or Gly$_z$. (z=1-10).

It is understood that such multimers may be built from any of the peptide variants described herein. Moreover, a peptide multimer may comprise different combinations of peptide monomers and the disclosed substitu0tion variants thereof. Such oligomeric or multimeric peptides can be made by chemical synthesis or by recombinant DNA techniques as discussed herein. When produced chemically, the oligomers preferably have from 2-8 repeats of the basic peptide sequence. When produced recombinantly, the multimers may have as many repeats as the expression system permits, for example from two to about 100 repeats.

Peptidomimetics

Another class of compounds useful in this regard are low molecular weight peptidomimetic compounds (which term also includes peptidomimetic) which influence the interactions between DAD and GBD. Such peptidomimetics may be identified by structural studies which compare the co-crystallization of DAD and GBD in the presence or absence of a candidate peptidomimetic.

A peptidomimetic of DAD mimics the biological effect of

[GA]-[VA]-M-D-x-L-L-E-x-L-[KRQ]-x-[GA]-[SGA]-[AP]

A peptidomimetic agent may be an unnatural peptide or a non-peptide agent which has the stereochemical properties of

[GA]-[VA]-M-D-x-L-L-E-x-L-[KRQ]-x-[GA]-[SGA]-[AP]

such that it has the binding activity or biological activity of the peptide. Hence, this invention includes compounds wherein a peptidomimetic compound is coupled to another peptide.

A peptidomimetic agent may be an unnatural peptide or a non-peptide agent which recreates the stereospatial properties of the binding elements of DAD such that it has the binding activity or biological activity of DAD. Similar to the linear peptides corresponding to DAD, a peptidomimetic will have a binding face (which interacts with GBD) and a non-binding face. Again, similar to the linear peptides of DAD, the non-binding face of a peptidomimetic will contain functional groups which can be modified by various therapeutic moieties without modifying the binding face of the peptidomimetic. A preferred embodiment of a peptidomimetic would contain an aniline on the non-binding face of the molecule. The $NH_2$-group of an aniline has a pKa ~4.5 and could therefore be modified by any $NH_2$-selective reagent without modifying any $NH_2$ functional groups on the binding face of the peptidomimetic. Other peptidomimetics may not have any $NH_2$ functional groups on their binding face and therefore, any $NH_2$, without regard for $pK_a$ could be displayed on the non-binding face as a site for conjugation. In addition other modifiable functional groups, such as —SH and —COOH could be incorporated into the non-binding face of a peptidomimetic as a site of conjugation. A therapeutic moiety could also be directly incorporated during the synthesis of a peptidomimetic and preferentially be displayed on the non-binding face of the molecule.

This invention also includes compounds which retain partial peptide characteristics. For example, any proteolytically unstable bond within a peptide of the invention could be selectively replaced by a non-peptidic element such as an isostere (N-methylation; D-amino acid at the $S_1$ site) or a reduced peptide bond while the rest of the molecule retains its peptide nature.

Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Hruby, V. J., *Biopolymers* 33:1073-1082 (1993); Wiley, R. A. et al., *Med. Res. Rev.* 13:327-384 (1993); Moore et al., *Adv. in Pharmacol* 33:91-141 (1995); Giannis et al., *Adv. in Drug Res.* 29:1-78 (1997), which references are incorporated by reference in their entirety). These methods are used to make peptidomimetics that possess at least the binding capacity and specificity of the cyclic peptides and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the cystallographically-derived three-dimensional structure of a peptide of the invention either free or bound in complex with GBD. Alternatively, the structure of a peptide of the invention bound to GBD can be gained by using nuclear magnetic resonance spectroscopy. The better knowledge of the stereochemistry of the interaction of a peptide with its binding partner will permit the rational design of such peptidomimetic agents.

Peptoids

Peptoids are oligomers of N-substituted glycines (Simon R J et al., *Proc Natl Acad Sci USA,* 1992 89:9367-9371). The 'peptoid' approach to the design of non-peptide, small molecule agonists and antagonists are also described by Horwell D C, Trends Biotechnol, 1995, 13:132-134. A peptoid of DAD would include substitution with, or addition of one or more such N-substituted glycines. The substituting group may be 4-aminophenol, isobutylamine, butyldiamine ($NH_2$ $(CH_2)_3NH_2$), cyclohexanemethylamine, aminomethylcyclopropane, benzylamine, methylamine, isopropylamine, R(+)-(L-methylbenzylamine), 5-(-1-α-methylbenzylamine, N-3-guanidinopropyl, etc. Such substituents have previously been demonstrated to lead to increased bioactivity of SH3-binding peptides by Nguyen. J. T. et al., Science 1998, 282:2088-2092. However, the substituting group can be virtually any substituent that can be substituted at the N position in glycine as long as the N-glycine product can be further coupled in a peptoid.

Capped Peptides

The peptide [GA]-[VA]-M-D-x-L-L-E-x-L-[KRQ]-x-[GA]-[SGA]-[AP], or active fragment thereof may be blocked or capped at its amino and carboxyl termini, preferably with acetyl bound to the amino-terminal N ("Ac") and amido (—$NH_2$ bound to the C-terminal carboxyl group ("Am")), respectively. This peptide may be referred to in single letter code indicating the blocking groups as Ac and Am groups:

Ac-[GA]-[VA]-M-D-x-L-L-E-x-L-[KRQ]-x-[GA]-[SGA]-[AP]-Am

The N-terminal capping function is preferably linked to the terminal amino function and may be selected from the group consisting of:

formyl; alkanoyl, having from 1 to 10 carbon atoms, such as acetyl, propionyl, butyryl; alkenoyl, having from 1 to 10 carbon atoms, such as hex-3-enoyl; alkynoyl, having from 1 to 10 carbon atoms, such as hex-5-ynoyl; aroyl, such as benzoyl or 1-naphthoyl; heteroaroyl, such as 3-pyrroyl or 4-quinoloyl; alkylsulfonyl, such as methanesulfonyl; arylsulfonyl, such as benzenesulfonyl or sulfanilyl; heteroarylsulfonyl, such as pyridine-4-sulfonyl;

substituted alkanoyl, having from 1 to 10 carbon atoms, such as 4-aminobutyryl;

substituted alkenoyl, having from 1 to 10 carbon atoms, such as 6-hydroxy-hex-3-enoyl;

substituted alkynoyl, having from 1 to 10 carbon atoms, such as 3-hydroxy-hex-5-ynoyl;

substituted aroyl, such as 4-chlorobenzoyl or 8-hydroxynaphth-2-oyl;

substituted heteroaroyl, such as 2,4-dioxo-1,2,3,4-tetrahydro-3-methyl-quinazolin-6-oyl;

substituted alkylsulfonyl, such as 2-aminoethanesulfonyl;

substituted arylsulfonyl, such as 5-dimethylamino-1-naphthalenesulfonyl;

substituted heteroarylsulfonyl, such as 1-methoxy-6-isoquinolinesulfonyl; carbamoyl or thiocarbamoyl;

substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl;

substituted carbamoyl (R'—NH—CO) or substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined;

The C-terminal capping function can either be in an amide bond with the terminal carboxyl or in an ester bond with the terminal carboxyl. Capping functions that provide for an amide bond are designated as $NR^1R^2$ wherein $R^1$ and $R^2$ may be independently drawn from the following group:

hydrogen;

alkyl, preferably having from 1 to 10 carbon atoms, such as methyl, ethyl, isopropyl;

alkenyl, preferably having from 1 to 10 carbon atoms, such as prop-2-enyl;

alkynyl, preferably having from 1 to 10 carbon atoms, such as prop-2-ynyl;

substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl;

substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl;

substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl;

aroylalkyl having up to 10 carbon atoms, such as phenacyl or 2-benzoylethyl;

aryl, such as phenyl or 1-naphthyl;

heteroaryl, such as 4-quinolyl;

alkanoyl having from 1 to 10 carbon atoms, such as acetyl or butyryl;

aroyl, such as benzoyl;

heteroaroyl, such as 3-quinoloyl;

OR' or NR'R" where R' and R" are independently hydrogen, alkyl, aryl, heteroaryl, acyl, aroyl, sulfonyl, sulfinyl, or $SO_2$—R'" or SO—R'" where R'" is substituted or unsubstituted alkyl, aryl, heteroaryl, alkenyl, or alkynyl.

All the foregoing peptides, peptoids, variants and chemical derivatives including peptidomimetics and multimeric peptides and peptoids must have the biological or biochemical activity (e.g., binding, disruption of DAD-GBD interactions, etc.) of

[GA]-[VA]-M-D-x-L-L-E-x-L-[KRQ]-x-[GA]-[SGA]-[AP]

as follows: at least about 20% of the activity of this peptide in an in vitro assay of cell viability or apoptosis. Alternatively, or in addition, variant, chemical derivative or peptoid should compete with labeled [GA]-[VA]-M-D-x-L-L-E-x-L-[KRQ]-x-[GA]-[SGA]-[AP] for binding to a ligand or binding partner, preferably GBD, when tested in a binding assay with whole cells, cell fractions, an isolated GBD-containing protein or peptide, or any other binding molecule.

Production of Peptides and Derivatives

General Chemical Synthetic Procedures

The peptides of the invention may be prepared using recombinant DNA technology. However, given their length, they are preferably prepared using solid-phase synthesis, such as that generally described by Merrifield, *J. Amer. Chem. Soc.,* 85:2149-54 (1963), although other equivalent chemical syntheses known in the art are also useful. Solid-phase peptide synthesis may be initiated from the C-terminus of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA resin or MBHA resin.

The preparation of the hydroxymethyl resin is described by Bodansky et al., *Chem. Ind.*, 38:1597-98 (1966). Chloromethylated resins are commercially available from Bio-Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, 1-6. BHA and MBHA resin supports are commercially available and are generally used only when the desired polypeptide being synthesized has an unsubstituted amide at the C-terminus.

The amino acids can be coupled to the growing peptide chain using techniques well known in the art for the formation of peptide bonds. For example, one method involves converting the amino acid to a derivative that will render the carboxyl group of the amino acid more susceptible to reaction with the free N-terminal amino group of the growing peptide chain. Specifically, the C-terminal of the protected amino acid can be converted to a mixed anhydride by the reaction of the C-terminal with ethyl chloroformate, phenyl chloroformate, sec-butyl chloroformate, isobutyl chloroformate, or pivaloyl chloride or the like acid chlorides. Alternatively, the C-terminal of the amino acid can be converted to an active ester, such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole. Another coupling method involves the use of a suitable coupling agent, such as N,N'-dicyclohexylcarbodiimide or N,N'-diisopropylcarbodiimide. Other appropriate coupling agents, apparent to those skilled in the art, are disclosed in Gross et al., *The Peptides: Analysis, Structure, Biology, Vol. I*, "Major Methods of Peptide Bond Formation" (Academic Press 1979).

The α-amino group of each amino acid employed in the peptide synthesis must be protected during the coupling reaction to prevent side reactions involving their active α-amino function. Certain amino acids contain reactive side-chain functional groups (e.g., sulfhydryl, amino, carboxyl, and hydroxyl) and such functional groups must also be protected with suitable protecting groups to prevent a chemical reaction from occurring at either (1) the α-amino group site or (2) a reactive side chain site during both the initial and subsequent coupling steps.

In the selection of a particular protecting group to be used in synthesizing the peptides, the following general rules are typically followed. Specifically, an α-amino protecting group (1) should render the α-amino function inert under the conditions employed in the coupling reaction, (2) should be readily removable after the coupling reaction under conditions that will not remove side-chain protecting groups and will not alter the structure of the peptide fragment, and (3) should substantially reduce the possibility of racemization upon activation, immediately prior to coupling. On the other hand, a side-chain protecting group (1) should render the side chain functional group inert under the conditions employed in the coupling reaction, (2) should be stable under the conditions employed in removing the α-amino protecting group, and (3) should be readily removable from the desired fully-assembled peptide under reaction conditions that will not alter the structure of the peptide chain.

It will be apparent to those skilled in the art that the protecting groups known to be useful for peptide synthesis vary in reactivity with the agents employed for their removal. For example, certain protecting groups, such as triphenylmethyl and 2-(p-biphenyl)isopropyloxycarbonyl, are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids for their removal, such as trifluoroacetic, hydrochloric, or boron trifluoride in acetic acid. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require even stronger acids, such as hydrogen fluoride, hydrogen bromide, or boron trifluoroacetate in trifluoroacetic acid, for their removal. Suitable protecting groups, known in the art are described in Gross et al., *The Peptides: Analysis, Structure, Biology, Vol. 3*: "Protection of Functional Groups in Peptide Synthesis" (Academic Press 1981).

The preferred α-amino protecting groups are BOC and FMOC. For the side chain amino group present in Lys, protection may be by any of the groups mentioned above in (1) such as BOC, 2-chlorobenzyloxycarbonyl and the like. For the guanidino group of Arg, protection may be provided by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC groups. For the hydroxyl group of Ser or Thr, protection may be, for example, by t-butyl; benzyl (BZL); or substituted BZL, such as p-methoxybenzyl, p-nitrobenzyl, p-chlorobenzyl, o-chlorobenzyl, and 2,6-dichlorobenzyl. For the carboxyl group of Asp or Glu, protection may be, for example, by esterification using such groups as BZL, t-butyl, cyclohexyl, cyclopentyl, and the like. For the imidazole nitrogen of His, the benzyloxymethyl (BOM) or tosyi moiety is suitably employed as a protecting group. For the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is bromobenzyloxycarbonyl. For the side chain amino group of Asn or Gln, xanthyl (Xan) is preferably employed. For Met, the amino acid is preferably left unprotected. For the thio group of Cys, p-methoxybenzyl is typically employed.

Other standard α-amino group de-protecting reagents, such as HCl in dioxane, and conditions for the removal of specific α-amino protecting groups are within the skill of those working in the art, such as those described in Lübke et al., *Chemie und Biochemie der Aminosaüren, Peptide und Proteine I*, Chapter II-1, 102-117 (Georg Thieme Verlag Stuttgart 1975). Following the removal of the α-amino protecting group, the unprotected α-amino group, generally still side-chain protected, can be coupled in a stepwise manner in the intended sequence.

An alternative to the stepwise approach is the fragment condensation method in which pre-formed peptides of short length, each representing part of the desired sequence, are coupled to a growing chain of amino acids bound to a solid phase support. For this stepwise approach, a particularly suitable coupling reagent is N,N'-dicyclohexylcarbodiimide or diisopropylcarbodiimide. Also, for the fragment approach, the selection of the coupling reagent, as well as the choice of the fragmentation pattern needed to couple fragments of the desired nature and size are important for success and are known to those skilled in the art.

Each protected amino acid or amino acid sequence is usually introduced into the solid-phase reactor in amounts in excess of stoichiometric quantities, and the coupling is suitably carried out in an organic solvent, such as dimethylformamide (DMF), $CH_2Cl_2$ or mixtures thereof. If incomplete coupling occurs, the coupling procedure is customarily repeated before removal of the N-amino protecting group in preparation for coupling to the next amino acid. Following the removal of the α-amino protecting group, the remaining α-amino and side-chain-protected amino acids can be coupled in a stepwise manner in the intended sequence. The success of the coupling reaction at each stage of the synthesis may be monitored. A preferred method of monitoring the synthesis is by the ninhydrin reaction, as described by Kaiser et al., *Anal. Biochem.*, 34:595 (1970). The coupling reactions can also be performed automatically using well-known commercial methods and devices, for example, a Beckman 990 Peptide Synthesizer.

Upon completion of the desired peptide sequence, the protected peptide must be cleaved from the resin support, and all protecting groups must be removed. The cleavage reaction and removal of the protecting groups is suitably accomplished concomitantly or consecutively with de-protection reactions. When the bond anchoring the peptide to the resin is an ester bond, it can be cleaved by any reagent that is capable of breaking an ester linkage and of penetrating the resin matrix. One especially useful method is by treatment with liquid anhydrous hydrogen fluoride. This reagent will usually not only cleave the peptide from the resin, but will also remove all acid-labile protecting groups and, thus, will directly provide the fully de-protected peptide. When additional protecting groups that are not acid-labile are present, additional de-protection steps must be carried out. These steps can be performed either before or after the hydrogen fluoride treatment described above, according to specific needs and circumstances.

When it is desired to cleave the peptide without removing protecting groups, the protected peptide-resin can be subjected to methanolysis, thus yielding a protected peptide in which the C-terminal carboxyl group is methylated. This methyl ester can be subsequently hydrolyzed under mild alkaline conditions to give the free C-terminal carboxyl group. The protecting groups on the peptide chain can then be removed by treatment with a strong acid, such as liquid hydrogen fluoride. A particularly useful technique for methanolysis is that of Moore et al., *Peptides, Proc. Fifth Amer. Pept. Symp.*, 518-521 (Goodman et al., eds., 1977), in which the protected peptide-resin is treated with methanol and potassium cyanide in the presence of a crown ether.

Other methods for cleaving a protected peptide from the resin when a chloromethylated resin is employed include (1) ammoniolysis and (2) hydrazinolysis. If desired, the resulting C-terminal amide or hydrazide can be hydrolyzed to the free C-terminal carboxyl moiety, and the protecting groups can be removed conventionally. The protecting group present on the N-terminal α-amino group may be removed either before, or after, the protected peptide is cleaved from the support. Purification of the peptides of the invention is typically achieved using chromatographic techniques, such as preparative HPLC (including reverse phase HPLC), gel permeation, ion exchange, partition chromatography, affinity chromatography (including monoclonal antibody columns), and the like, or other conventional techniques such as countercurrent distribution or the like.

Gene "Therapy"

Because Dia proteins play a role in normal control of cell cycle progression, including completion of cytokinesis, their genes are considered to act as a tumor suppressor genes the mutation or deletion of which could lead to escape from growth control and tumorigenesis. Disruption of Dia function could lead to dysregulation of cell division. For example, a cell lacking or having a mutated, nonfunctional mDia2 gene (or a subject having such cells) can be treated and the dysfunction corrected by introduction of the functional gene or its product. According to the invention, DAD or a DAD-like peptide introduced into a cell exogenously, or expressed in the cell following genetic modification of the cell, is used to correct or treat such a condition. Similarly, mDia2 loss may occur as a part of "natural" tumor progression in certain types of tumors. Restoration of this function using DAD, or inducing apoptosis in such cells by expressing DAD, is therefore a preferred approach for treating subjects having a developing tumor in which loss of mDia2 function, or the function of another gene that encodes a DAD peptide is part of the pathogenic process. Introduction of DAD can be achieved by various methods known collectively as "gene transfer" or "gene therapy" (discussed below).

Another use of the present invention is to screen cells for expression of an mDia gene such as mDia2 or its human homologue. DAD stabilizes microtubules in a manner similar to taxol, and results in cell killing. Therefore, it would be useful to know whether a tumor has selective loss of expression of mDia, correctable by DAD expression as disclosed herein. Thus, in conjunction with the therapeutic embodiments described herein, a method is provided to screen cells for mDia gene expression either at the mRNA or proteins levels using convention methods to determine whether a tumor would be relatively susceptible or resistant to DAD-based therapy. Anti-mDia antibodies are useful in this regard. Moreover, it is possible to screen directly for the DAD peptide as a measure of expression of the mDia gene.

Gene therapy or transfer involves introduction of a "foreign" gene into a cell and ultimately, into a live animal. Several general strategies for gene therapy have been studied and have been reviewed extensively (Yang, N-S., *Crit. Rev. Biotechnol.* 12:335-356 (1992); Anderson, W. F., *Science* 256:808-813 (1992); Miller, A. S., *Nature* 357:455-460 (1992); Crystal, R. G., *Amer. J. Med.* 92(suppl 6A): 44S-52S (1992); Zwiebel, J. A. et al., *Ann. N.Y. Acad. Sci.* 618:394-404 (1991); McLachlin, J. R. et al., *Prog. Nucl. Acid Res. Molec. Biol.* 38:91-135 (1990); Kohn, D. B. et al., *Cancer Invest.* 7:179-192 (1989), which references are herein incorporated by reference in their entirety).

One approach comprises gene transfer into primary cells in culture followed by autologous transplantation of the ex vivo transformed cells into the host, either systemically or into a particular organ or tissue.

For accomplishing the objectives of the present invention, gene therapy would be accomplished by direct transfer of a the functionally active DNA into mammalian somatic tissue or organ in vivo, and more preferably, into cells the growth of which is to be arrested. DNA transfer can be achieved using a number of approaches described below. These systems can be first tested for successful expression in vitro by use of a selectable marker (e.g., G418 resistance) to select transfected clones expressing the DNA, followed by detection of the presence of the desired gene product after treatment with the inducer using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful transfer of genes known in the art include: (a) direct injection of plasmid DNA into mouse muscle tissues, which led to expression of marker genes for an indefinite period of time (Wolff, J. A. et al., *Science* 247:1465 (1990); Acsadi, G. et al., *The New Biologist* 3:71

(1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., *J. Biol. Chem.* 265:17285 (1990); Koleko, M. et al., *Human Gene Therapy* 2:27 (1991); Ferry, N. et al., *Proc. Natl. Acad. Sci. USA* 88:8387 (1991)); (d) intratracheal infusion of recombinant adenovirus into lung tissues was effective for in vivo transfer and prolonged expression of foreign genes in lung respiratory epithelium (Rosenfeld, M. A. et al., *Science* 252:431 (1991); (e) Herpes simplex virus vectors achieved in vivo gene transfer into brain tissue (Ahmad, F. et al., eds, *Miami Short Reports—Advances in Gene Technology: The Molecular Biology of Human Genetic Disease,* Vol 1, Boerringer Manneheim Biochemicals, USA, 1991).

Retroviral-mediated human gene therapy utilizes amphotrophic, replication-deficient retrovirus systems (Temin, H. M., *Human Gene Therapy* 1:111 (1990); Temin et al., U.S. Pat. No. 4,980,289; Temin et al., U.S. Pat. No. 4,650,764; Temin et al., U.S. Pat. No. 5,124,263; Wills, J. W. U.S. Pat. No. 5,175,099; Miller, A. D., U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D. G. et al., *Mol. Cell. Biol.* 10:4239 (1990). This condition is met by the preferred target cells for the present DNA molecules, i.e., actively growing tumor cells. Gene therapy of cystic fibrosis using transfection by plasmids using any of a number of methods and by retroviral vectors has been described by Collins et al., U.S. Pat. No. 5,240,846

The DNA molecules encoding the growth inhibitory DAD sequences may be packaged into retrovirus vectors using packaging cell lines that produce replication-defective retroviruses, as is well-known in the art (see, for example, Cone, R. D. et al., *Proc. Natl. Acad. Sci. USA* 81:6349-6353 (1984); Mann, R. F. et al., *Cell* 33:153-159 (1983); Miller, A. D. et al., *Molec. Cell. Biol.* 5:431-437 (1985); Sorge, J., et al., *Molec. Cell. Biol.* 4:1730-1737 (1984); Hock, R. A. et al., *Nature* 320:257 (1986); Miller, A. D. et al., *Molec. Cell. Biol.* 6:2895-2902 (1986). Newer packaging cell lines which are efficient an safe for gene transfer have been described more recently (Bank et al., U.S. Pat. No. 5,278,056;

The gene therapy approach can be utilized in a site specific manner to deliver the retroviral vector to the tissue or organ of choice. Thus, for example, a catheter delivery system can be used (Nabel, E. G. et al., *Science* 244:1342 (1989)). Such methods, using either a retroviral vector or a liposome vector, is particularly useful to deliver the gene to a blood vessel wall, or into the blood circulation of a tumor. Other virus vectors may also be used, including recombinant adenovirus vectors (Horowitz, M. S., In: *VIROLOGY,* Fields, B. N. et al., eds, Raven Press, New York, 1990, p. 1679; Berkner, K. L., *Biotechniques* 6:616 9191988), Strauss, S. E., In: *THE ADENOVIRUSES,* Ginsberg, H. S., ed., Plenum Press, New York, 1984, chapter 11), herpes simplex virus (HSV) for neuron-specific delivery and persistence. Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human gene therapy (Samulski, R. J. et al., *EMBO J.* 10:3941 (1991) according to the present invention.

Another vector which can express the DNA molecule of the present invention, and is useful in gene therapy, in particular in humans, is vaccinia virus, which can be rendered non-replicating (U.S. Pat. Nos. 5,225,336; 5,204,243; 5,155,020; 4,769,330; Sutter, G et al., *Proc. Natl. Acad. Sci. USA* (1992) 89:10847-10851; Fuerst, T. R. et al., *Proc. Natl. Acad. Sci. USA* (1989) 86:2549-2553; Falkner F. G. et al.; *Nucl. Acids Res* (1987) 15:7192; Chakrabarti, S et al., *Molec. Cell. Biol.* (1985) 5:3403-3409). Descriptions of recombinant vaccinia viruses and other viruses containing heterologous DNA and its uses in immunization and gene therapy are reviewed in: Moss, B., *Curr. Opin. Genet. Dev.* (1993) 3:86-90; Moss, B. *Biotechnology* (1992) 20: 345-362; Moss, B., *Curr Top Microbiol Immunol* (1992) 158: 25-38; Moss, B., *Science* (1991) 252:1662-1667; Piccini, A et al., *Adv. Virus Res.* (1988) 34:43-64; Moss, B. et al., *Gene Amplif Anal* (1983) 3:201-213.

In addition to virus-mediated gene transfer in vivo, physical means well-known in the art can be used for direct gene transfer, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R. S. et al., *Proc. Natl. Acad. Sci. USA* 88:2726 (1991); Zelenin, A. V. et al., *FEBS Lett.* 280:94 (1991); Zelenin, A. V. et al., *FEBS Lett.* 244:65 (1989); Johnston, S. A. et al., *In Vitro Cell. Dev. Biol.* 27:11 (1991)). Furthermore, electroporation, a well-known means to transfer genes into cell in vitro, can be used to transfer DNA molecules according to the present invention to tissues in vivo (Titomirov, A. V. et al., *Biochim. Biophys. Acta* 1088: 131 ((1991)).

Gene transfer can also be achieved using "carrier mediated gene transfer" (Wu, C. H. et al., *J Biol. Chem.* 264: 16985 (1989); Wu, G. Y. et al., *J. Biol. Chem.* 263:14621 (1988); Soriano, P. et al., *Proc. Natl. Acad. Sci. USA* 80:7128 (1983); Wang, C-Y. et al., *Proc. Natl. Acad. Sci. USA* 84:7851 (1982); Wilson, J. M. et al., *J. Biol. Chem.* 267:963 (1992)). Preferred carriers are targeted liposomes (Nicolau, C. et al., *Proc. Natl. Acad. Sci. USA* 80:1068 (1983); Soriano et al., supra) such as immunoliposomes, which can incorporate acylated monoclonal antibodies into the lipid bilayer (Wang et al., supra). Polyclonal antibodies and mAbs specific for various types of tumors are well-known in the art. Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

A plasmid vector may be microinjected into cells in vitro or in vivo for expression therein of the growth suppressing DAD peptide. Alternatively, the DNA molecule may be placed in a vector such as a retrovirus vector or adenovirus vector capable of infecting cells in vivo and thereby delivering the DNA molecule of the invention (see below). Plasmid DNA used for transfection or microinjection may be prepared using methods well-known in the art, for example using the Quiagen procedure (Quiagen), followed by DNA purification using known methods, such as the methods exemplified herein.

Similarly, a peptide or polypeptide including the DAD sequence may be microinjected into target cells After a sufficient interval, cells may be examined by immunofluorescence or other means for expression of the transfecting growth-inhibitory DNA. Growth inhibition may be examined by quantitating BrdU incorporated using a specific antibody.

The ability of the DNA molecule of the present invention, once transfected into a target cell, to inhibit cell growth may be tested using any cell proliferation or growth assay known in the art. A colony forming efficiency assay, may be used for certain classes of tumor cells. Measurement of incorporation of a radiolabeled precursor such as $^3$H-thymidine is also useful. Yet another assay involves uptake of a chromogenic dye, for example the tetrazolium salt MTT (3-(4,5-dimethylthiazol-2-yl)-2,5-diphenyl tetrazolium bromide) (Mosmann, T. (*J. Immunol. Meth.* 65:55-63 (1983)), which is modified by mitochondrial dehydrogenase enzymes to form a blue formazan product, the absorbance of which can be measured spectrophotometrically at 570 nm. Over a certain range of cell numbers, this substrate resulted in a linear relationship between cell number and color formed.

Plasmids

The DNA molecules and derivatives of the present invention may be expressed using any appropriate expression vector as is well-known in the art (Sambrook, J. et al., *Molecular Cloning: A Laboratory Manual*, 2nd Edition, Cold Spring Harbor Press, Cold Spring Harbor, N.Y., 1989). One useful expression vector is pGEX-KG.

Preferred expression plasmids are described in Example I below and in the description of the Figures.

More generally, a DNA molecule encoding the DAD or a derivative thereof may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, ligation with appropriate ligases, or the synthesis of fragments by the polymerase chain reaction (PCR). Techniques for such manipulations are disclosed by Sambrook, et al. (supra) and are well known in the art.

To target a particular type of cell, for example tumor cells growing in vivo, any of a number of alternate vectors which include the DAD-encoding DNA sequences of the present invention may be selected. First, control sequences with tissue specificity for the tissue type of the target cells may be used. Examples of promoters with such specific modes of action include the insulin gene promoter for selective expression in the pancreas or the MMTV or lactalbumin promoter for expression in breast tissue.

For expression of DAD or other functional derivative from the plasmids in the target cells, the endogenous translation stop codons may be utilized. If construct having a C-terminal truncation is used in which the endogenous stop codon is lacking, a stop codon is inserted in the vector just downstream of the cloning site.

For transfection of a cell in vitro according to the present invention, a selectable marker gene (such as G418-resistance) may be added, either on the same plasmid or by contransfection using a second plasmid such as pSV2neo (Southern, P. J. et al. *J Mol Appl Genet* (1982) 1:327-341) or the pIPB1 plasmid (Biamonti, G. et al. *Nucl Acid Res* (1985) 13:5547-5561). For transfection of a cell with DAD DNA in vivo, a selection marker useful in vivo may be preferred, for example, the tk gene of HSV.

Promoters and Enhancers

A promoter region of a DNA or RNA molecule binds RNA polymerase and promotes the transcription of an "operably linked" nucleic acid sequence. As used herein, a "promoter sequence" is the sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another.

The preferred promoter sequences of the present invention must be operable in mammalian cells, and may be either eukaryotic or viral promoters. Suitable promoters may be inducible, repressible or constitutive. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., *Cell* 41:521 (1985)) or in the RSV-LTR (from Rous sarcoma virus) (Gorman, C. M., *Proc. Natl. Acad. Sci. USA* 79:6777 (1982). Also useful are the promoter of the mouse metallothionein I gene (Hamer, D., et al., *J Mol. Appl. Gen.* 1:273-288 (1982)); the TK promoter of Herpes virus (McKnight, S., *Cell* 31:355-365 (1982)); the SV40 early promoter (Benoist, C., et al., *Nature* 290:304-310 (1981)); and the yeast gal4 gene promoter (Johnston, S. A., et al., *Proc. Natl. Acad. Sci. (USA)* 79:6971-6975 (1982); Silver, P. A., et al., *Proc. Natl. Acad. Sci. (USA)* 81:5951-5955 (1984)). Other illustrative descriptions of transcriptional factor association with promoter regions and the separate activation and DNA binding of transcription factors include: Keegan et al., *Nature* (1986) 231:699; Fields et al., *Nature* (1989) 340:245; Jones, *Cell* (1990) 61:9; Lewin, *Cell* (1990) 61:1161; Ptashne et al., *Nature* (1990) 346:329; Adams et al., *Cell* (1993) 72:306. All of the above-listed references are incorporated by reference herein.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112, 767). For a general discussion of enhancers and their actions in transcription, see, Lewin, B. M., *Genes IV,* Oxford University Press, Oxford, (1990), pp. 552-576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency on the DAD-encoding DNA molecule of the present invention.

Pharmaceutical and Therapeutic Compositions and their Administration

The compounds that may be employed in the pharmaceutical compositions of the invention include all of those compounds described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

As stated above, the compounds of the invention possess the ability to inhibit cell growth or to induce apoptosis, properties that are exploited in the treatment of cancer, in particular metastatic cancer. A composition of this invention may be active per se, or may act as a "pro-drug" that is converted in vivo to the active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Preferably, the compounds of the invention are administered systemically, e.g., by injection. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the diagnosis or treatment of any of a number of animal genera and species, and are equally applicable in the practice of human or veterinary medicine. Thus, the pharmaceutical compositions can be used to treat domestic and commercial animals, including birds and more preferably mammals, as well as humans.

Though the preferred routes of administration are systemic the pharmaceutical composition may be administered topically or transdermally, e.g., as an ointment, cream or gel; orally; rectally (e.g., as a suppository), parenterally, by injection or continuously by infusion; intravaginally; intrapenilely; intranasally; intrabronchially; intracranially, intraaurally; or intraocularly.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topic application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to an infected area, e.g., skin surface, mucous membrane, eyes, etc. This amount will generally range from about 0.001 mg to about 1 g per application, depending upon the area to be treated, the severity of the symptoms, and the nature of the topical vehicle employed.

Therapeutic compositions of the invention may comprise, in addition to the DAD peptide, one or more additional anti-tumor agents, such as mitotic inhibitors, e.g., vinblastine; alkylating agents, e.g., cyclophosphamide; folate inhibitors, e.g., methotrexate, piritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase, topoisomerse inhibitors such as etoposide; or biological response modifiers, e.g., interferons or interleukins. In fact, pharmaceutical compositions comprising any known cancer therapeutic in combination with the peptides disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents.

Having now generally described the invention, the same will be more readily understood through reference to the following examples which are provided by way of illustration, and are not intended to be limiting of the present invention, unless specified.

EXAMPLE I

Methods for Examples II-V see, also Albert, A S., *J. Biol. Chem.* 276:2824-2830 (2001)

Cell Culture, Microinjection and Fluorescence Microscopy

NIH 3T3 cells grown on glass coverslips were maintained in Dulbecco's modified essential medium (Gibco; BRL) containing 10% (v/v) fetal calf serum (FCS; Gibco) until 24 h prior to microinjection when cells were changed to medium containing 0.1% (v/v) FCS. The NIH 3T3 SRE-FosHA reporter cell line HA13 was used in all SRE gene expression studies Sahai, E. et al., *Embo J* 17, 1350-1361 (1998)). Cells were microinjected with pulled-glass capillaries using an Eppendorf 5171 semi-automated injection system as previously described (Kikyo et al., supra). Purified plasmid DNA expression vectors were microinjected at concentration of 10 µg/ml each in a buffer of PBS:dH$_2$O (1:1), unless indicated otherwise; empty vector (pEF$_m$) was included in experiments normalize injected DNA concentrations when necessary. For fluorescent detection experiments, cells were fixed 2 h after microinjection with 3.7% formaldehyde in PBS and permeabilized with 0.3% Triton X-100 (Sigma) prior to staining. SRE-regulated FosHA staining was detected by indirect immunofluorescence using primary rabbit anti-HA anti-sera (Y-11; Santa Cruz Biotechnology) followed by AMCA coupled anti-rabbit (Jackson). Filamentous actin was monitored in cells by staining with TRITC-labeled phalloidin (Sigma). After staining, coverslips were mounted in gelvatol. Fluorescent images were captured with a digital camera (SPOT R100; Diagnostics) mounted on a Nikon E400 epifluorescence microscope using fixed exposure times with either 40× or 100× (1.4NA) where indicated. Images were saved as TIFF files and assembled into figures using ClarisDraw.

Plasmids and Genbank™ Accession Numbers mDia1, mDia2 and various domain expression constructs were made in pEF$_m$ (courtesy of R. Marais), pEF$_{HA}$, pEF$_m$EGFP, pT7-plink, pGEX-KG and pGAD 10 from PCR products using standard methods and confirmed by direct sequencing; complete details are available upon request. In vitro translation plasmids were made using pT7-plink (Akada, R. et al., *Mol Gen Genet* 254, 267-274 (1997)). Accession numbers for the gene products discussed: mDia1, U96963; mDia2, AF094519; DIA156, NP_006720; Diaphanous, AAA67715; Bni1, P41832; SepA, AAB63335. For most of the experiments, plasmids encoded the following amino acids for mDia2: GBD, 101-216; FH1, 521-630; FH2, 801-910; DAD, 1031-1171 unless otherwise indicated.

In Vitro GST-'Pull Downs' and Two-Hybrid Assays

Two-hybrid assays and in vitro translation/GST-pull downs were conducted as previously described (Kikyo et al., supra; Hill, C. S. et al., supra). In short, the indicated 'bait' proteins were generated by subcloning the indicated cDNAs into pGBT9 Gal4 DNA binding domain plasmid; 'prey' were Gal4 activation domain fusion proteins generated in either pGAD 10 or pSE1107. HF7c (Clontech) reporter yeast strain were co-transformed with the indicated plasmids and selected on appropriate plates for bait and prey auxotrophic markers, then restreaked onto His-plate to select for Gal4 regulated HIS reporter expression. Levels of reporter activity were monitored by replicate streaking onto Trp/Leu/His-plates with increasing concentrations (0-64 mM) of 3-aminotriazole.

For in vitro translation and pull-downs, plasmids were constructed using pT7-plink or pCAN (Akada et al., supra) containing the indicated coding sequences for mDia2 (Kikyo et al., supra), GBD or FH1 were in vitro translated using the TNT kit (Promega) using $^{35}$S-labeled methionine. 4 µl of labeled IVT product were incubated with 100 µg of GST, GST-DAD or GST-SrcSH3, bound to glutathione beads as indicated. Beads were incubated at 4° C. with rocking for 2 h in 25 mM Tris pH 7.2, 100 mM NaCl and 10 mM MgCl$_2$. Binding reactions were warmed to 30° C. before addition of recombinant RhoA-V14 (Sahai et al., supra). Beads were collected by centrifugation; after washing beads 3× in 5 volumes of bed volume in binding buffer, beads were suspended in SDS-sample buffer, electrophoresed, then stained with Coommassie blue R250 and dried prior to autoradiography.

EXAMPLE II

Identification of DAD

Amino acid sequence alignments of the growing FH protein superfamily delineate the proline-rich FH1 and FH2 regions of homology (Wasserman, supra; Castrillon et al., supra). Comparative alignment of only the DRF sub-family yielded a conserved domain in the C-termini that is shown in FIG. 1. The consensus sequence

[GA]-[VA]-M-D-x-L-L-E-x-L-[KRQ]-x-[GA]-[SGA]-[AP]

was designated the DRF-autoregulatory domain or DAD. There was also a conserved region of basic residues several residues towards the C-terminal are indicated by underline. The DAD domain was found in all the three mouse/human DRFs (Bione et al., supra; Peterson et al., supra; Tominaga et al., supra, *Drosophila* Diaphanous (Castrillon et al., supra), budding yeast *Saccharomyces cerevisiae* Bni1p (Roche, S. et al., *Science* 269, 1567-1569 (1995)), and *Emericella nidulans* SepA proteins (Harris et al., supra); the exception appeared to be Bnr1p.

EXAMPLE III

DAD Expression Activates Actin Remodeling and SRF

Figure 2C:
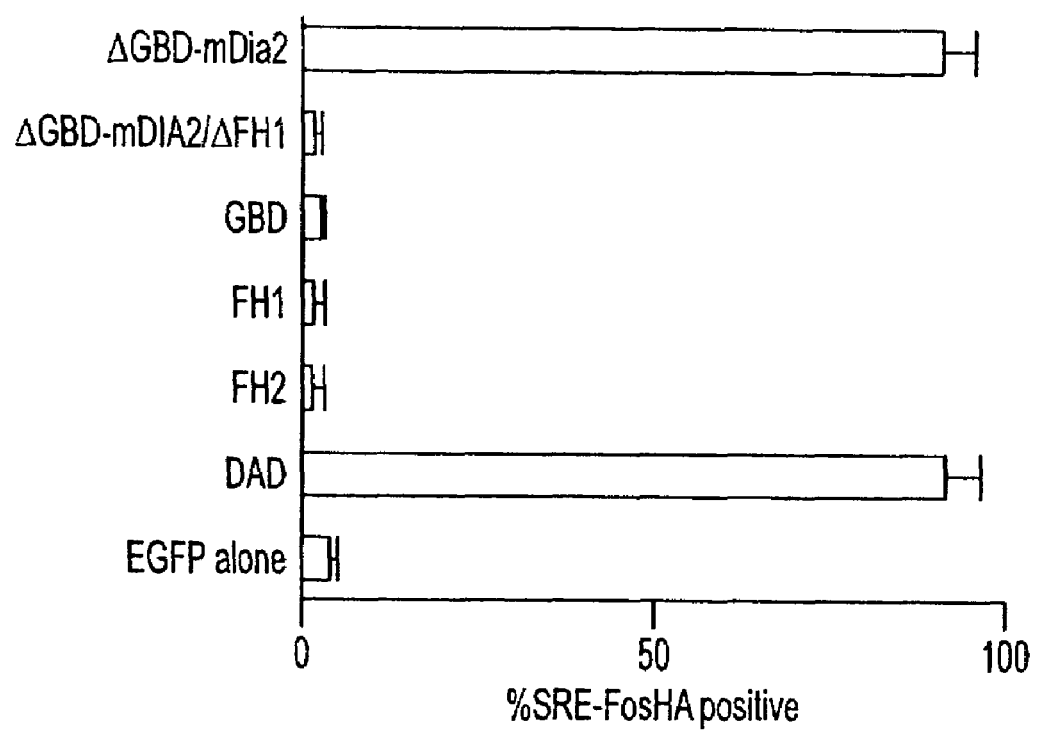
FIGS. 2A, 2B and 2C. Expression of the isolated DAD activates actin remodeling and SRF.

To examine the role of the DAD domain in DRF function, the mDia2 DAD domain was fused to EGFP in a mammalian expression plasmid (pEF$_m$EGFP-DAD) that was microinjected into NIH 3T3 cells maintained in low serum (0.1% FCS) for 24 h. 3 h after injection, the effects on actin reorganization and activation of SRF were assayed. Actin polymerization was observed by staining cells with fluorescent TRITC-phalloidin and SRF-regulated gene expression was monitored by staining HA13 cells for the induction of a stably transformed SRE-controlled Fos-reporter gene that contained an HA-tag by indirect immunofluorescence (Sahai et al., supra). The effects of EGFP-DAD were compared to similar EGFP-fusion proteins containing other mDia2 domains, including the GBD, FH1 and FH2 sequences. While none of the other homology domains had an effect on actin or SRF activity, EGFP-DAD expression strongly induced the formation of actin filaments in cells as shown in FIG. 2A. Actin remodeling was not dependent upon EGFP as expression of non-EGFP fusion proteins had similar effects. In addition to the increased formation of actin fibers, the cells also became elongated and increased the number of focal adhesions. The localization of the fusion proteins deffered greatly. The EGFP-FH1 fusion was predominantly nuclear with some diffuse cytoplasmic localization. However, upon stimulation with LPA, the EGFP-FH1 fusion began to decorate actin stress fibers as shown in the example in FIG. 2B. The inset shows a region from the EGFP-FH1-expressing cell in top row; merged images clearly show overlapping EGFP-FH1/stress fibers. EGFP-FH2 localization was consistently diffuse throughout the cell, whereas EGFP-DAD was excluded from the nucleus. DAD did appear to concentrate at the ends of a subset of actin fibers in cells expressing higher levels of DAD but not the extent seen with EGFP-FH1. EGFP-DAD strongly induced SRF as summarized in FIG. 2C where bars represent the number of FosHA positive GFP-fusion expressing cells.

The formation of actin fibers and activation of SRF have been previously observed after expression of GBD truncated or 'activated' mDia1 and mDia2. Organized stress fiber formation is dependent upon cooperative DRF and Rho-kinase (ROCK) activity because stress fiber formation is blocked by treatment of cells with the ROCK inhibitor Y-27632 (Watanbe et al., 1999, supra; Kikyo et al., supra; Zhao et al., supra). Similar to the activated DRFs, DAD induction of organized actin filaments was inhibited by Y-27632 treatment prior to injection of expression plasmids. ROCK inhibition did not have any effect on DAD activation of SRF however, similar to results previously obtained with activated mDia1 and mDia2.

EXAMPLE IV

Self-Association: DAD Interaction with the GBD

Watanabe and colleagues (1999, supra) previously reported that the N-terminus of mDia1 could bind to its C-terminus. A similar intramolecular interaction was also reported for the Cdc42-binding WASP (Alberts et al., 1998, supra).

To test if a similar interaction could occur with mDia2, the DAD domain was tested for binding to the GBD in both two hybrid and GST-'pull down' assays as shown in FIGS. 3A and B, respectively. In vitro both mDia2 and the isolated GBD bound specifically to the DAD domain. The DAD-GBD or DAD-mDia2 interaction was tested for regulation by activated Rho Both in vitro translated $^{35}$S-methionine labeled GBD and mDia2 were incubated with increasing concentrations of activated recombinant RhoA-V14 produced as GST-fusion proteins in bacteria. Activated Rho disrupted the association of both the GBD and mDia2 as shown in FIG. 3B, but did not have any effect on FH1-SrcSH3 binding.

A model based on these observations is shown in FIG. 3C. In cells with low levels of activated Rho-GTP, the DRFs assume an inactive state with the C-terminal DAD directly interacting with the N-terminal GBD. Rho activation and GBD binding induces release of the DAD then effectors are recruited through the FH1 and FH2 domains. The C-terminal DAD, like the VCA domain of WASP, may be a bi-functional regulator. In this event, the DAD not only associates with the GBD but also recruits 'effectors' such as the ARP2/3 complex in a manner analogous to the WASP-VCA domain (Alberts et al., supra).

EXAMPLE V

Testing the Autoregulatory Model in Cells

Figure 4B:
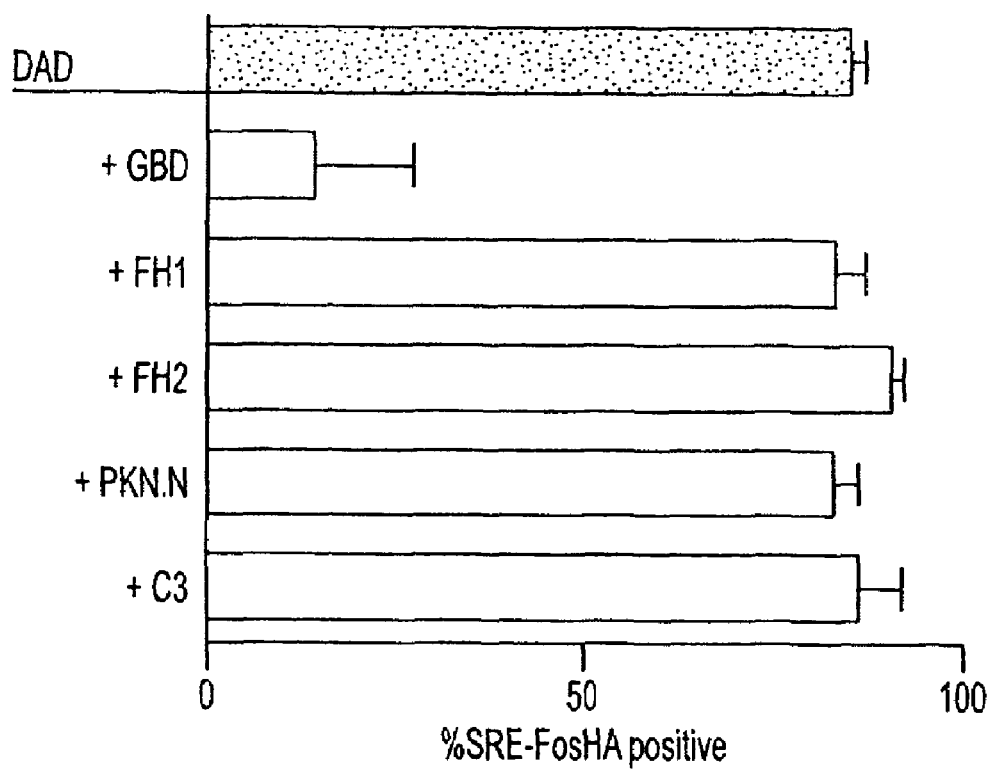

The autoregulatory model predicts that overexpression of the GBD would neutralize the effects of DAD domain expression through direct binding. To test this, plasmids encoding both GBD (pEF$_m$-GBD) and DAD (pEF$_m$EGFP-DAD) were microinjected into cells; actin and SRF activity were monitored as before. As shown in FIG. 4A, GBD expression blocked DAD-induced actin remodeling. Co-injection of either FH1 or FH2 domains were without effect. Similar results were obtained when SRF activity was assayed (FIG. 4B). These results showed that the GBD expression inhibited the DAD domain in trans and was, in effect, squelching the DAD domain.

The GBD could also block SRF and actin remodeling if DAD was activating Rho. Expression of other Rho GTPase binding domains have been shown to block Rho signaling (Sahai et al., supra). DAD activation of Rho was tested despite the presumption that the DRFs were downstream effectors of Rho signaling. DAD was co-expressed with either the N-terminus of PKN (PKN.N) or C3 transferase which also inhibits Rho-signaling but not the activated DRFs (Sahai et al., supra; Maesaki, R. et al Mol Cell 4, 793-803 (1999)). Neither C3 or PKN.N inhibited DAD activation of SRF (FIG. 4B) though each blocked serum activation of SRF as previously reported. Because of this specific blockade of DAD, it was concluded that DAD was triggering signals downstream of the Rho GTPases.

Figures 1, 4C:
Figures 2, 4C:
Figures 3, 4C:
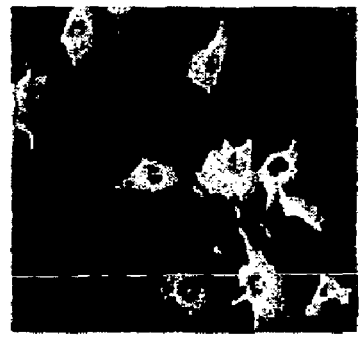
Figures 4, 4C:
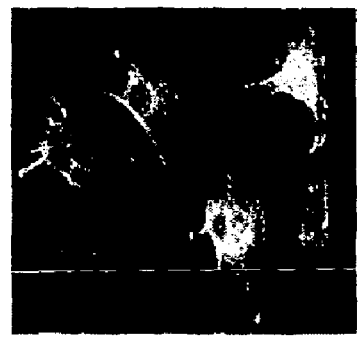
Figure 4D:
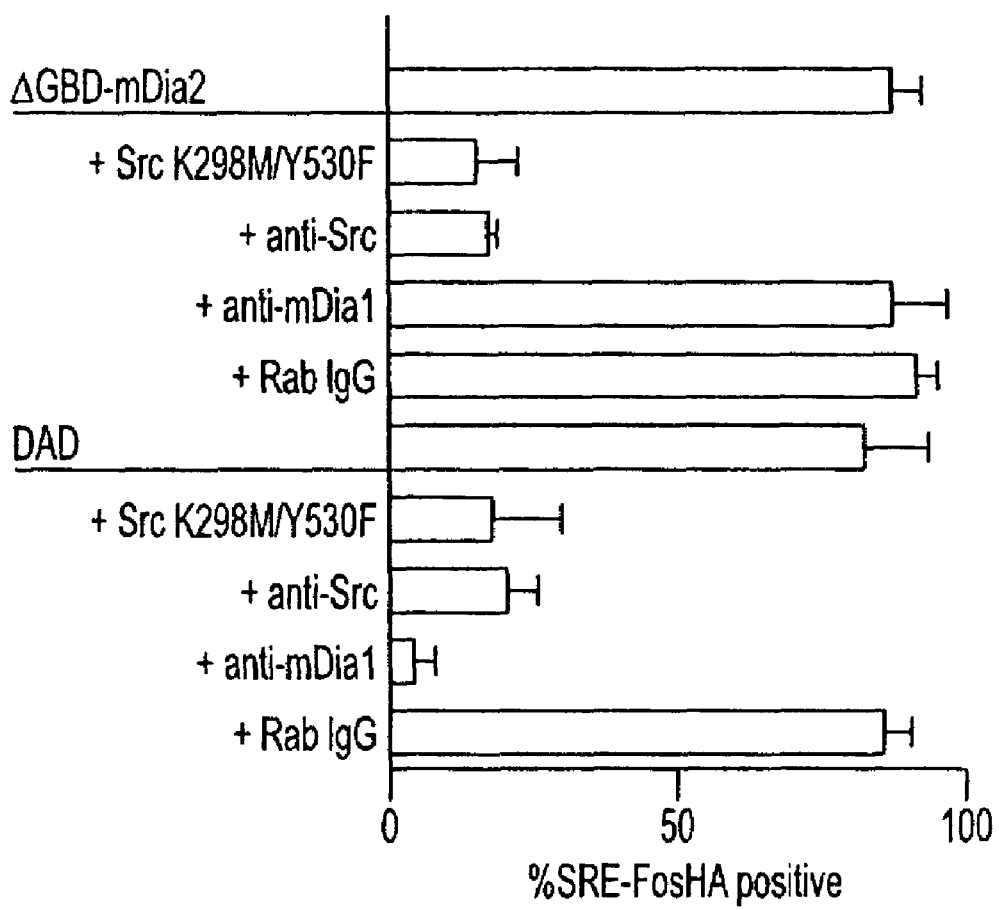

If DAD was an effector domain analogous to the WASP-VCA domain, GBD neutralization of DAD activity would be predicted. An alternative explanation for DAD activity is as follows: DAD inhibits a negative intramolecular DAD-GBD association. In this case, DAD domain expression would be activating endogenous DRF proteins by unlatching the GBD-DAD autoregulatory mechanism. This possibility was tested by expressing DAD and simultaneously inhibiting endogenous mDia1 by co-injection of affinity purified anti-peptide antibodies with the EGFP-DAD expression vector (Kikyo et al.). This antibody recognizes amino acids mDia1 amino acids 66-77 (YGDDPTAQSLQD) of the amino-terminus. Anti-mDia1 effectively blocked DAD activity as it influenced actin remodeling and SRF (FIGS. 4C and D). Anti-mDia1 did not inhibit SRF inductionby the deletion variants ΔGBD-mDia2 (FIG. 4D) or ΔGBD-mDia1 as they lack the peptide sequence recognized by the anti-mDia1 antibodies. Interfering Src (FIG. 4A, right panels) and anti-Src (Alberts, A. S. et al., J Biol Chem 273, 8616-8622 (1998)) also blocked DAD induced stress fiber formation and SRF (FIGS. 4C and D). Thus, DAD domain effects depend on endogenous DRFs. For NIH 3T3 cells, the DRF is mDia1. These inhibitors would not have an effect if the DAD domain had 'effector' activity that recruited downstream targets of the DRFs in Rho signaling.

Figure 5A:
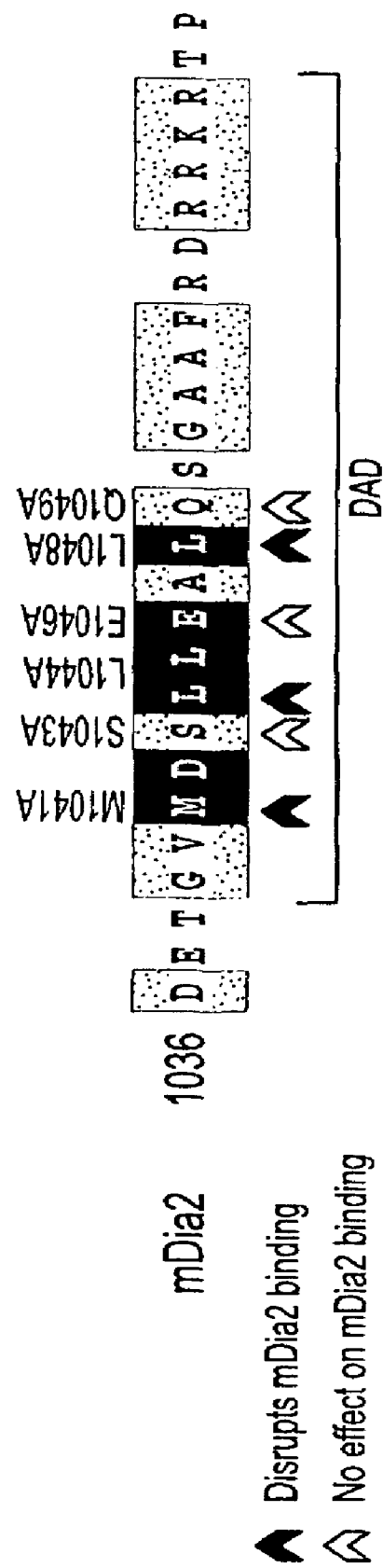
FIGS. 5A and 5B. Mutations of DAD that disrupt DRF binding inhibit biological activity.

To correlate DAD-DRF binding with DAD biological activity, alanine-scanning mutagenesis was performed along the DAD consensus region. The mutants were tested for binding by two-hybrid analysis and were then expressed in cells. Results of the binding experiments are shown in FIG. 5A. Mutations that disrupted the mDia2-DAD interaction are indicated by the filled arrowheads; mutations that had no effect on mDia2 interaction are shown by the open arrowheads. M1041A, L1044A, L1048A (amino acid positions are from the mDia2 peptide sequence; variable residues in gray boxes, identical/conserved residues in in black boxes) substitutions of conserved DAD residues disrupted binding and leading to lack of activity in both SRF and actin fiber formation as shown in FIG. 5B. The localization of the L1044A mutant was also significantly altered. Instead of diffuse membrane localization of the wild type DAD, L1044A had punctate localization in the membrane and cell edge, giving the cell a 'moth-eaten' appearance. It also allowed the fusion protein to appear in the nucleus. L1044A expression also caused the formation of extensions reminiscent of those resulting from HIV-1 Nef expression, which complexes with several protein kinases (Vav, PAK1 and Src). However, the DAD mutants lacked the filamentous actin seen in the Nef-induced trichopodia. Alanine substitutions of the non-conserved residues S1043A and Q1049A had no effect on binding and both could induce fiber formation and SRF. Interestingly, the E1046A substitution of the conserved glutamate residue was also without effect, suggesting that binding DAD-mDia2 is largely mediated through hydrophobic interactions. The interaction is also strongly dependent upon the stretch of basic residues adjacent to the 'core' DAD sequence. Introduction of a stop codon at position 1050 weakened but did not eliminate the interaction as determined by two-hybrid assay and also reduced the number and density of apparent fibers in cells (FIG. 5B, lower right-hand panels).

The present inventor is examining the importance of these residues and the variable distance from the DAD core in its biological activity. Taken together, the results of these DAD mutational experiments show that DAD activity is dependent upon its ability to bind to a full-length DRF.

EXAMPLE VI

Materials and Method for Examples VI-VIII

Cell culture, microinjection and fluorescence microscopy. NIH 3T3 cells were maintained in Dulbecco's modified essential medium (Gibco; BRL) containing 10% (v/v) fetal calf serum (FCS; Gibco) and plated on glass coverslips; 24 h prior to microinjection, cells were changed to medium containing 0.1% (v/v) FCS. Cells were microinjected as previously described (Tominaga et al., supra). Purified plasmid DNA expression vectors were microinjected at concentration of 110 μg/ml each in a buffer of PBS:dH$_2$O (1:1) unless indicated otherwise; empty vector (pEF$_m$) was included in experiments to normalize injected DNA concentrations when necessary. For fluorescent detection of filamentous actin, cells were fixed 3 h after microinjection with 3.7% formaldehyde in PBS and permeabilized with 0.3% Triton X-100 (Sigma) prior to staining with TRITC-labeled phalloidin (Molecular Probes) for 60 mins at ambient room temperature. For detection of p34Arc and Arp3, after formaldehyde fixation, cells were extracted with −20° C. methanol for 20 min. Following extensive rehydration in PBS for 2 hrs, coverslips were incubated with the indicated rabbit polyclonal antisera diluted in PBS/5% donkey serum (Jackson) overnight at 4° C. in a humidified chamber. The primary antisera was detected with Texas red-labeled donkey anti-rabbit following washes in PBS. Coverslips were then mounted in gelvatol. Fluorescent images were captured with a digital camera (SPOT R100; Diagnostics) mounted on a Nikon E400 epifluorescence microscope using fixed exposure times with a 100× (1.4NA) objective. Images were assembled into figures using ClarisDraw.

Plasmids and Genbank™ accession numbers. mDia2 and various domain expression contructs were made in pEF$_m$ (courtesy of R. Marais), pEF$_m$EGFP and pGEX-KG from PCR products using standard methods and confirmed by direct sequencing; complete details are available upon request. Accession numbers for mDia2, AF094519. For most of the experiments, plasmids encoded the following amino acids for mDia2 DAD, 1031-1171 with indicated amino-acid substitutions unless otherwise indicated; all plasmids were sequenced to confirm the mutagenesis.

Recombinant protein purification, in vitro GST-'pull downs' and two-hybrid assays. Two-hybrid assays and in vitro translation/GST-pull downs were conducted as previously described (Tominaga et al., supra; Sahai, E. et al., Embo J 17, 1350-61 (1998)). GST-DAD fusion proteins were produced using standard methods and protein concentrations determined by comparison to known standards on coomassie R250 stained gels or by BioRad kit dye-binding assay. For Arp2/3 and actin binding experiments, GST or GST-tagged DAD (20 μg), immobilized on glutathione beads saturated with 1 μg/μl BSA, were mixed either with 1 μg of purified Arp2/3 complex or 1 μg of G-actin in PBS 1× supplemented with 0.1 μg/μl of BSA and incubated for 1 h at 4° C. on a rotating wheel. Beads were rinsed three times with PBS 1× supplemented with 0.1 μg/μl of BSA and were analyzed by SDS-PAGE and immunoblotted with purified antibodies recognising either Arp3, p34, or actin. For pull-downs from cell extracts, NIH 3T3 cells were lysed and extracted as per (Machesky, L. M. et al., Curr Biol 8, 1347-56 (1998)), and incubated with purified GST-fusion proteins bound to glutathione beads before extensive washing, separation by SDS-PAGE, transfer, and immunoblotting.

Pyrene-actin polymerization assay. Rabbit skeletal muscle actin (Spudich, J. A. et al., J Biol Chem 246, 4866-71 (1971)), pyrene-labeled actin (Kouyama, T. et al., Eur J Biochem 114, 33-8 (1981); Cooper, J. A. et al., J Muscle Res Cell Motil 4, 253-62 (1983)) and WASP-PWCA (Yarar, D. et al., Curr Biol 9, 555-8 (1999)) were prepared as described elsewhere. Pyrene-actin polymerization assays were performed as described previously Welch, M. D. et al., Trends Cell Biol 9, 423-7 (1999) with the following modifications. Pyrene-actin and unlabeled actin were mixed in G-buffer (5 mM Tris pH 8, 0.2 mM CaCl$_2$, 0.2 mM ATP, 0.2 mM DTT) to generate a 2.5 μM G-actin solution with less than 20% pyrene-actin. 6 μl of Arp2/3 complex with WASP-PWCA or with GST-DAD or with GST was mixed with 6 μl 10× initiation buffer (20 mM MgCl$_2$, 10 mM EGTA, 5 mM ATP). This 12 μl solution was mixed with 48 μl of G-actin solution to initiate polymerization. Assembly kinetics were monitored using a Fluorolog 3 fluorometer (Instruments S.A.; excitation wavelength 365 nm, emission wavelength 407 nm) maintained at a temperature of 25° C.

Antibodies. Affinity purified antibodies that recognize Arp3 and p34 were described previously (Welch, M. D. et al., Nature 385, 265-9 (1997)). A mouse monoclonal anti-actin (Clone/C4) antibody was used according to protocols provided by the manufacturer (ICN biochemicals).

EXAMPLE VII

DAD is Similar to the WASP WCA Domain

DAD was previously identified during a comparison of the amino acid sequences of fungal, insect and mammalian DRFs (Alberts et al., 2001, supra) and shown in FIG. 6a. We then hypothesized that the DRFs were autoregulated by small GTPase-modulated intramolecular binding in a manner directly analogous to WASP. For DAD to behave similarly to WASP, we investigated whether it had intrinsic action on actin, which had not previously been shown. We first examined sequence similarities between WASP and DAD for clues about DAD function.

Shown in FIG. 6b are alignments of known actin- and Arp2/3 binding proteins and cofilin. It was readily apparent that the DRFs do not have acidic C-termini that are known to be involved in WASP activation of Arp2/3 (Takenawa et al., supra). Closer inspection of the alignment revealed that the most significant similarity was between the WH2 domain and the conserved leucine-rich 'core' of DAD, though there are some significant differences between the WH2 and DAD: WH2 contains an Arg 3 positions N-terminal to the Leu-Leu motif at the critical Met residue in DAD (see above; Alberts et al., 2001, supra), and the Ile (of WH2) and Leu (of DAD) thats are 3 residues from the Leu-Leu motif. The WH2 domains also have a conserved Leu flanked by basic residues, whereas DADs have the 3-4 basic residues similar to those found in other regions of WASP, ActA, and cofilin (right side of FIG. 6b). The basic regions from ActA have been studied in detail (Pistor, S. et al., J Cell Sci 113, 3277-87 (2000); Skoble, J. et al., J Cell Biol 150, 527-38 (2000)), and clearly have a role in Arp2/3 targeting in bacteria.

EXAMPLE VIII

DAD Interactions with the Arp2/3 Complex and G-Actin

1. DAD Binds Directly to the Arp2/3 Complex and G-Actin.

Figure 7C:
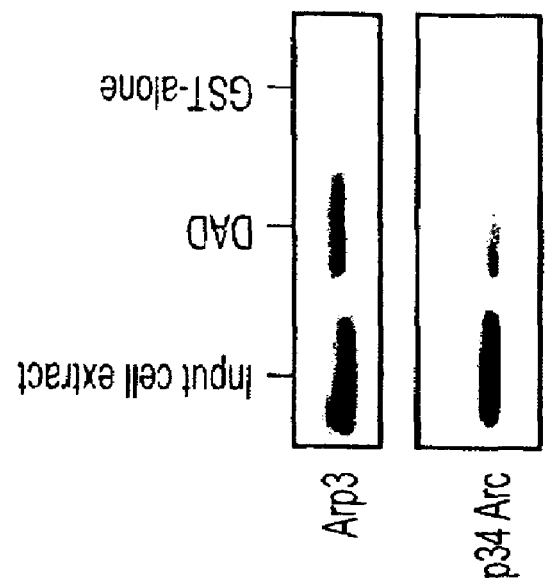
FIGS. 7a-7c show that DAD binds to G-actin and to Arp2/3.
Figure 7B:
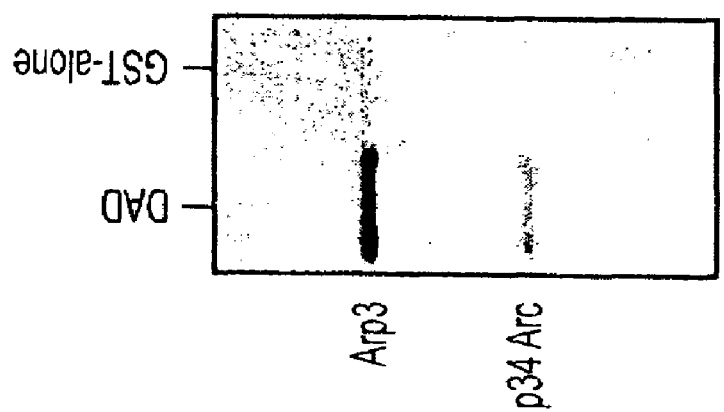
Figure 7A:
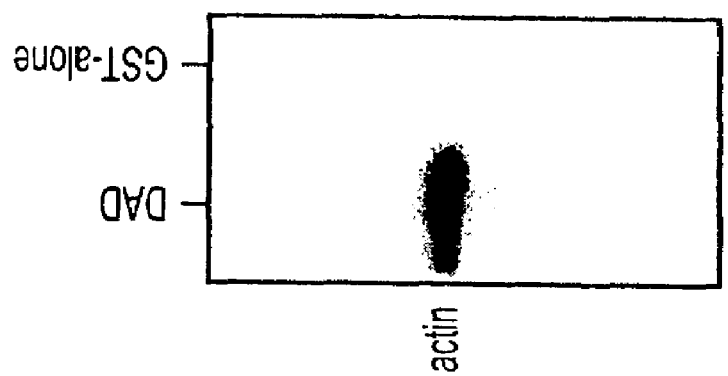
Figure 8:
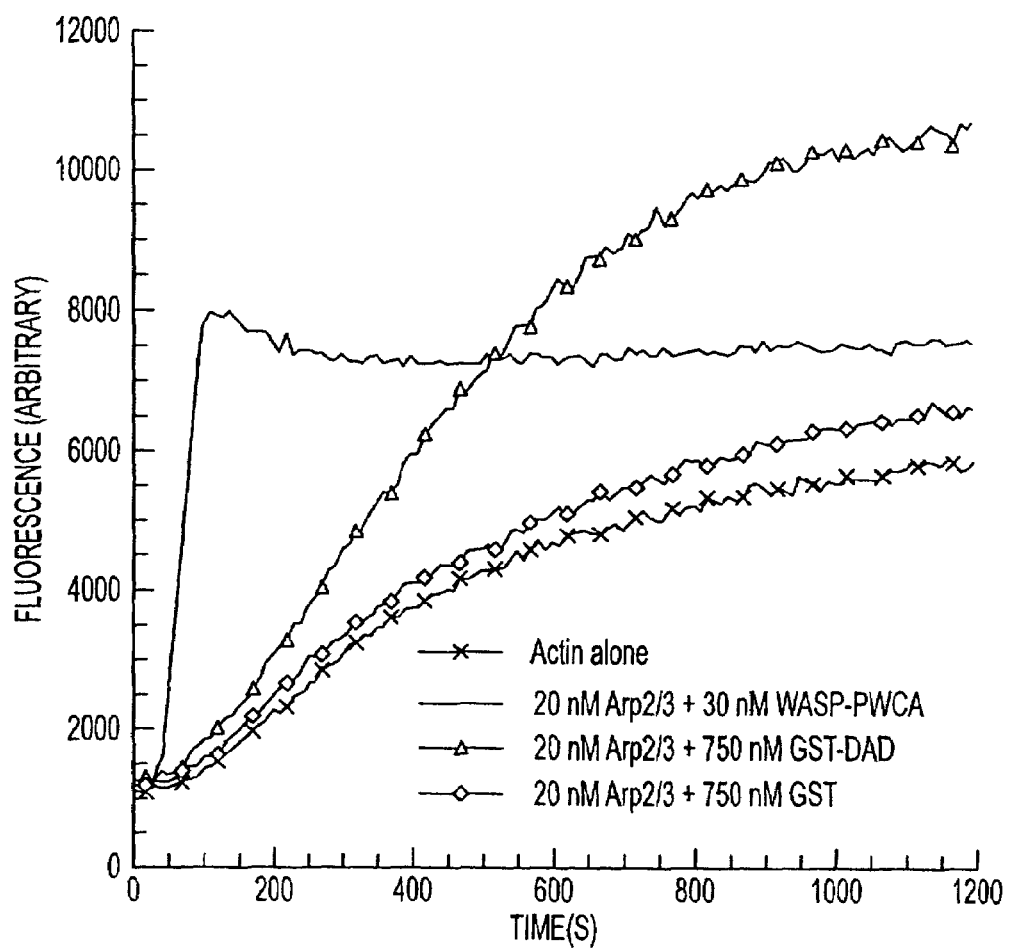

Because of the similarity with the WASP-WCA domain, in particular the homology with the WH2 region, we predicted that DAD would interact with Arp2/3 and G-actin. To test this hypothesis, purified GST-DAD bound to glutathione-Sepharose beads were incubated with purified G-actin or Arp2/3 purified from platelets (Welch, M. D. et al., Methods Enzymol 298, 52-61 (1998)). After incubation, the complexes were washed extensively and the resulting protein complexes were separated by SDS-PAGE, transferred to membranes, and analyzed by Western blots using antibodies directed to actin, Arp3 and p34 Arc (Welch, M. D. et al., Nature 385, 265-9 (1997)). As shown in FIGS. 7a and 7b, DAD binds to G-actin and the purified Arp2/3 complex, respectively. GST-DAD was tested for binding to Arp2/3 from cell lysates made from NIH 3T3 cells (FIG. 7c). As with the purified complex, we could detect binding to Arp2/3. Arp2/3 binding from cell extracts was also assayed using other domains from mDia2, including the GBD, FH1 and FH2 (see above; Alberts et al., 2001, supra). None of these other GST-fusion proteins associated with Arp2/3. DAD-Arp2/3 association was also tested by two-hybrid analysis (Alberts et al., 1998, supra). Only interaction with p21 was observed.

2. DAD Activates Arp2/3 In Vitro.

Figures 1, 6C:
FIG. 6a-6c. DAD activates actin polymerization and is homologous to WASP-WH2.
Figures 2, 6C:
Figures 3, 6C:
Figures 4, 6C:
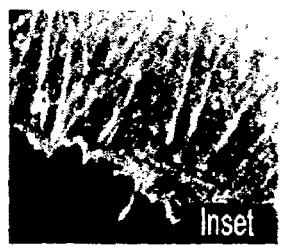
Figures 5, 6C:
Figures 6, 6C:
Figures 6, 6C, 7:
Figures 6, 6C, 7, 8:
FIG. 8 shows the effect of GST-DAD on actin nucleation with the Arp2/3 complex. Shown is a graph of fluorescence intensity versus time after initiating the polymerization of 2.5 µM actin in the pyrene-actin polymerization assay as described in Example VI. 20 nM Arp2/3 complex was activated with either 30 nM WASP-PWA or 750 nM GST-DAD. 750 nM GST was used as a control.

Because DAD binds to the Arp2/3 complex and G-actin and activates the assembly of actin fibers in cells, we sought to determine whether DAD could activate the actin-nucleating activity of the Arp2/3 complex using the pyrene-actin polymerization assay. While GST-DAD alone had no effect on the kinetics of actin polymerization at the concentrations tested, it exhibited significant Arp2/3 stimulating activity (FIG. 8). However, the activity of GST-DAD was weak compared to that of the PWCA fragment of WASP (consisting of the Proline rich, WH2, Connector and Acidic regions) which is a potent stimulator of the Arp2/3 complex (FIG. 8). These results demonstrate that DAD couples G-actin with Arp2/3 and activates actin polymerization.

3. The Basic Region of the DAD Activity and Binding to Arp2/3

Figures 6, 6C, 7, 8, 9:

ActA, SCAR and WASP proteins have basic or 'cofilin' homology domains that participate or contribute to Arp2/3 activation (Pistor et al., supra; Skoble et al., supra; Bi, E. et al., Curr Biol 9, R160-3 (1999)). In order to test the importance of the conserved basic residues in DAD (see FIG. 6b), we extended the previous mutational analysis (supra) by analysing the role of the DAD basic region. FIG. 9a shows a summary of the amino acid substitutions made in the mDia2 DAD region. These were expressed as EGFP fusion proteins and representative images are shown in FIG. 9b. Single Ala substitutions of each respective basic residue between amino acid 1057 and 1060 were without effect as were double substitutions at positions 1055 and 1056. We then double-substituted Glu at positions 1057 and 1058, 1059 and 1060, or 1063 and 1065. Both sets of DAD double mutants, DAD R1057E/R1058E and DAD K1059E/R1060E, lost the ability to induce thin fibers; DAD mutant R1057E/R1058E also appeared to be disrupted in the pre-existing actin network. We then purified GST-fusion proteins of these DAD variants and tested them for their ability to complex with Arp2/3 as in FIG. 7a-7c. As shown in FIG. 9c, we found that the double Glu subsitutions disrupted the ability of DAD to associate with Arp2/3. As with the basic region of ActA, DAD requires an intact basic region for both Arp2/3 binding and induction of thin fibers in cells.

4 DAD and Full-Length mDia2 Co-Localize with Arp2/3 Components in Discrete Regions of the Cell.

Figures 3, 10B:
FIGS. 3A, 3B and 3C. Interaction of DAD with the N-terminal GBD.
FIG. 10 is a series of photomicrographs showing the co-localization of Arp3 and p34 Arc with DAD and mDia2 following stimulation of cells with lysophosphatidic acid (LPA).
In FIG. 10a, EGFP-DAD was expressed in NIH 3T3 cells for 3 hrs then fixed with formaldehyde before extraction with methanol as described in Example VI. Cells were then stained with rabbit anti-Arp3 (FIG. 10a) or anti-p34 Arc (FIG. 10b). EGFP-DAD was found in striations corresponding to the actin filament networks. Both Arp3 and p34 Arc were also found in the same pattern as shown by the stippled rectangles in the insets of the merged images. Both Arp2/3 components were also found in discrete patches at the cell edge. Arp3 co-localization with EGFP-DAD is indicated by the arrowhead.
FIGS. 10c and 10d: Co-localization of full-length mDia2 with Arp3 and p34 Arc, respectively, in LPA (10 µM) treated cells; cells were injected with an expression vector for full-length mDia2 (pEFmDia2). 2 hrs later, cells were stimulated with LPA for 10 mins. Cells were then fixed and stained with the 9E10 antibody as well as rabbit anti-Arp3 (FIG. 10c) or p34 Arc (FIG. 10d). Both co-localized in striations at the cell periphery and were also concentrated in the termini of cell extensions with mDia2.
Figures 6, 10B:
Figures 2, 10B:
Figures 5, 10B:
Figures 1, 10B:
Figures 4, 10B:
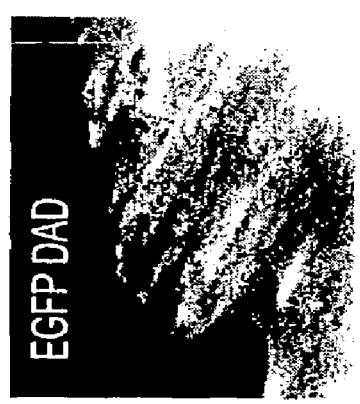
Figures 2, 10C:
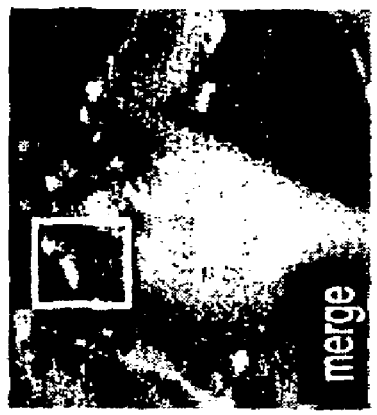
Figures 3, 10C:
Figures 5, 10C:
Figures 6, 10C:
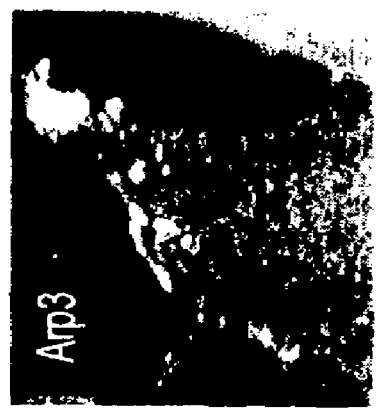
Figures 1, 10C:
Figures 4, 10C:
Figures 3, 10D:
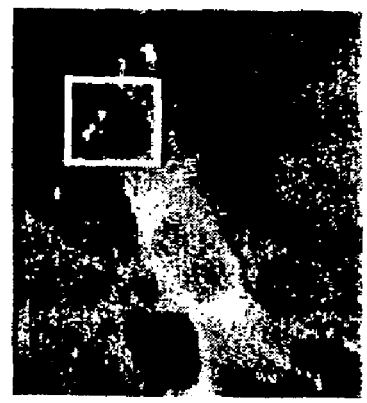
Figures 6, 10D:
Figures 2, 10D:
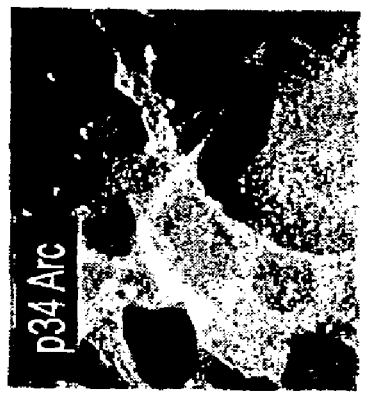
Figures 5, 10D:
Figures 1, 10D:
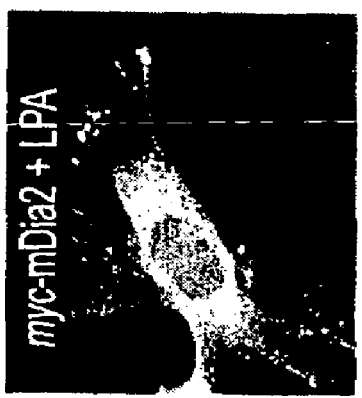
Figures 4, 10D:

We analyzed the localization of Arp3 and p34 Arc by indirect immunofluorescence using rabbit polyclonal antibodies. Cells were tested 3 hrs after injection of the EGFP-DAD expression plasmid. As shown in FIG. 10a and inset, EGFP-DAD assumed a striated pattern that was presumed to be stress fibers. (We could not co-stain with labelled phalloidin due to the fixation conditions used in these experiments.) We also found discrete patches of the fusion protein near the cell periphery as indicated by arrows. Co-staining with rabbit anti-Arp3 revealed that EGFP-DAD and Arp3 were both targeted to these regions. Both Arp3 (FIG. 10a) and p34 Arc (FIG. 10b) aligned along the DAD striations as indicated by the stippled boxes. We also found p34 Arc at the cell edge along with EGFP-DAD. These results show that DAD co-localizes with Arp2/3 in regions of the cell associated with new actin polymerization as shown in FIG. 6a-6c.

Figure 11:
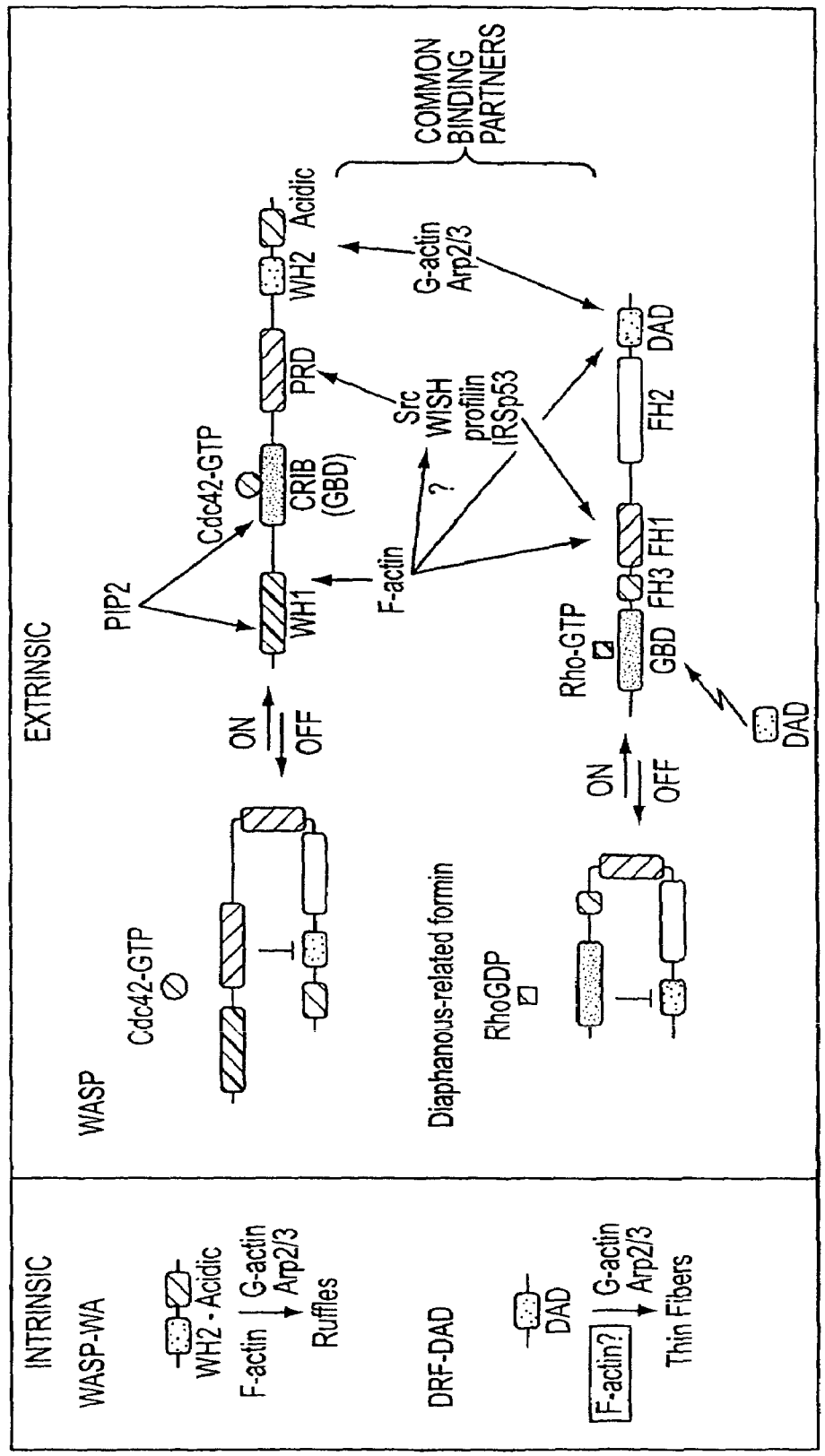
FIG. 11 is a schematic drawing showing intrinsic versus extrinsic activation of actin remodeling. The intrinsic model suggests that the DAD and WCA peptides contain sufficient information to activate Arp2/3 to generate either ruffles (WCA) or thin fibers (DAD). The Extrinsic model indicates that multiple cellular signals are required for these effects in cells. These factors, such as Src and $PIP_2$, contribute to the recruitment or modulation of the DRFs or WASP in cells.

We then examined whether Arp2/3 could be found with full-length mDia2 in cells stimulated with a known activator of Rho small GTPases, in this case lysophosphatidic acid (LPA). Cells were injected with pEFmyc-mDia2 and 2 hrs after injection were treated with 10 µM LPA. The location of myc-mDia2 was detected by indirect immunofluorescence using the 9E10 (myc) mAb in addition to the anti-Arp2/3 antibodies. In unstimulated cells, myc-mDia2 was found in endosomes and other small vesicles as previously described (Tominaga et al., supra). LPA treatment induces the targeting of myc-mDia2 into structures with phosphotyrosine and other focal adhesion components (FIG. 11). Some cells also produced extensions containing mDia2 at their tips. As seen in the insets, both Arp3 and p34 Arc are also concentrated in these extensions. Combined with our actin co-injection experiments in FIG. 6c, these results suggest that the DRFs target Arp2/3 to the cell periphery prior to, or during, the production of actin fibers.

5. Discussion

The results show that the Dia-autoregulatory domain, DAD, a conserved region found in the Diaphanous-related formins, binds to and activates the Arp2/3 complex. These observations are important, not only because they link Rho directly to cellular components that control actin polymerization, but because DAD represents a novel protein interface that signals to Arp2/3. DAD, like the WCA domain, binds to actin monomers and Arp2/3 directly. DAD nucleates actin in vitro and triggers actin polymerization in cells although the rates of actin nucleation differ greatly from WASP-PWCA in vitro. In cells, DAD does not induce ruffles or lamellipodia but induces thin fibers. Our observations lead to two models for how Rho small GTPase effectors communicate with Arp2/3 and activate the formation of their idiosyncratic actin-based structures. The models incorporate previously published data in addition to our own, in an attempt to highlight important similarities and differences between DAD and WASP in Rho GTPase directed actin remodeling. These models are illustrated in FIG. 6 as either the 'intrinsic' or the 'extrinsic' model, shown on the left and right, respectively.

a. Intrinsic Versus Extrinsic.

The Intrinsic model suggests that domains of WASP and the DRFs that contact Arp2/3 or actin monomers convey sufficient information to dictate the type of structure that the complex will generate. The initial biochemical evidence shown here using purified reagents indicates that WASP and DAD are intrinsically different: WASP triggers actin polymerization with a minimal lag phase whereas DAD slowly induces polymerization. Currently under study in the lab is the mDia2 L1044A substituted DAD variant which we have previously shown to disrupt the actin fiber network and induce cellular protusions and ruffles (Alberts et al., 2001, supra). This suggests that a specific alteration in DAD is sufficient to alter its intrinsic activity and cause it to bind to either actin or Arp2/3 and cause ruffles, instead of thin fibers. However, this is complicated by the inability of DAD L1044A to bind to the GBD of mDia2 and therefore disrupt autoinhibition and activate the cellular DRFs by mimicking active Rho (Alberts et al., 2001, supra). We postulate that DAD L1044A still activates Arp2/3, whose default activity is to cause ruffles and not cause fibers because it does not specifically trigger other DRF controlled events that occur upon binding of either Rho or DAD to the GBD.

These multiple signaling events are found in the Extrinsic model which includes the combination of signals that, in concert, leads to the formation of specific actin structures. These signals would be delivered by proteins or small molecules that interact with other DRF or WASP domains, such as Src (Tominaga et al., supra; Banin, S. et al., *Curr Biol* 6, 981-8 (1996); Uetz, P. et al., *J Biol Chem* 271, 33525-30 (1996) and IRSp53 (Fujiwara, T. et al., *Biochem. Biophys. Res. Comm.* 271, 626-629 (2000); Takenawa et al, supra; Miki, H. et al, *Nature* 408, 732-5 (2000)). The interactions would target or modulate the active Arp2/3 remodeling machinery bound to either WA or DAD within the cell. DAD was shown here to be targeted to specific regions of the cell associated with actin fiber production, whereas, following LPA treatment, full-length mDia2 was predominantly located at the cell periphery at the tips of extensions. LPA does not alter the subcellular localization of DAD. These results suggest that the other domains of the DRFs contribute to its targeting within cells. The net effect of these interactions would dictate the type of actin remodeling occurring in response to activation of a given small GTPase.

It is difficult to reconcile this extrinsic model at this stage, as the DRFs and WASP share many common binding partners (indicated on the right side of FIG. 11). All of the WASP binding factors, except for WIP and PIP2, are known to interact with DRFs. This includes WISH, which we have identified as an mDia1- and mDia2-binding protein by two-hybrid screening. PIP2 does appear to have an important role in the formation of actin fibers, and expression of PIP5 kinase has been shown to induce the formation of stress fibers in cells (Yamamoto, M. et al., *J Cell Biol* 152:867-876 (2001)).

The explanation for specificity may be due to the activating GTPase. Thus, the type of structure that is generated in cells is controlled by the number and types of effectors targeted by the respective GTPase. For example, activated RhoA induces the formation of stress fibers following the activation of Rho-effectors ROCK, phospholipase (D Kam, Y. et al., *Mol Cell Biol* 21, 4055-66 (2001)) and DRFs. This GTPase-specific explanation would require that the GTPases discriminate between effectors. However, it is not clear that the DRFs are that selective. Bni1p, for example, binds both Rho1 and Cdc42p; the latter has an important role in targeting Bni1p to bud tips (Ozaki-Kuroda et al., supra; Evangelista et al., supra). Cdc42Hs also binds to the mammalian DRF mDia2 (Alberts et al., 1998, supra), but it has not yet been demonstrated whether this actually occurs in cells.

DRFs not only bind to RhoA and Cdc42, but also to RhoB, RhoC and the constitutively GTP-bound Rho family members Rnd1-3. We hypothesize that specificity might hinge upon regional activation of small GTPases. For example, the bonefide activator of the DRFs may indeed be RhoB which is also targeted to endosomes (Mellor, H. et al., *J Biol Chem* 273, 4811-4 (1998) along with mammalian DRFs Tominaga et al., supra).

b. Old Versus New

The above results suggest that DAD induces de novo actin polymerization in cells. Machesky, L. M. et al., *J Cell Biol* 138, 913-26 (1997), using the same method of co-injecting labelled actin, concluded that activated RhoA did not stimulate de novo actin polymerization within the short time period used here, but suggested instead the reorganization of existing fibers. If RhoA does not activate actin polymerization, then a model that incorporates RhoA in the activation of the DRFs and the recruitment of Arp2/3 to DAD would be incorrect. There are multiple explanations for this, the most likely being that, in the prior study, RhoA Q63L was produced in bacteria as a recombinant protein with no post-translational modification (geranyl-geranylation of the CaaX motif) (Adamson, P. et al., *J Biol Chem* 267, 20033-8 (1992)). Thus, the activated GTPase was not correctly targeted to the cellular pool of effectors, accounting for a lag period period following injection. The idea that the DRFs utilize pre-existing fibers cannot be discounted as DAD, along with Arp2/3, decorates fibers in cells. Further, using various biochemical approaches to analyze cell lines with inducible forms of DAD, we found that both DAD and Arp2/3 translocate to the actin fiber network when DAD is activated. The mechanism that accounts for this effect is currently under investigation but together, the results suggest that DAD may connect or use pre-existing filaments during fiber production.

Finally, the results presented herein demonstrate that DAD has the ability to stimulate Arp2/3. This finding resolves several years of speculation about how Rho communicates with the actin remodeling machinery. While several actin-binding proteins have been shown to interact with Bni1p and the mammalian DRFs, including profilin and Bud6p/Aip3 (Ozaki-Kuroda et al., supra; Evangelista et al., supra; Watahabe et al., supra; Sheu, Y. J. et al., *Mol Cell Biol* 18, 4053-69 (1998)), their specific roles in Rho-DRF controlled actin remodeling has not been identified. We predict that they participate in modulating the initial actin nucleation events triggered by DAD interaction with Arp2/3. Alternatively, they are also small GTPase or DRF directed factors that regulate actin polymerization. Such a role has been suggested for profilin in WASP activation of Arp2/3 (Yang, C. et al., *J Cell Biol* 150, 1001-12 (2000)).

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

SEQUENCE LISTING

```
<160> NUMBER OF SEQ ID NOS: 9

<210> SEQ ID NO 1
<211> LENGTH: 15
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa can be Gly or Ala
<220> FEATURE:
<221> NAME/KEY: MISC_FEATURE
<222> LOCATION: (2)..(2)
<223> OTHER INFORMATION: Xaa can be Val or  Ala
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be Lys, Arg or Gln
<220> FEATURE:
<221> NAME/KEY: MISC_FEATURE
<222> LOCATION: (12)..(12)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be Glu or Ala
<220> FEATURE:
<221> NAME/KEY: MISC_FEATURE
<222> LOCATION: (14)..(14)
<223> OTHER INFORMATION: Xaa can be Ser, Glu or Ala
<220> FEATURE:
<221> NAME/KEY: MISC_FEATURE
<222> LOCATION: (15)..(15)
<223> OTHER INFORMATION: Xaa can be  Ala or Pro

<400> SEQUENCE: 1

Xaa Xaa Met Asp Xaa Leu Leu Glu Xaa Leu Xaa Xaa Xaa Xaa Xaa
1               5                   10                  15

<210> SEQ ID NO 2
<211> LENGTH: 21
<212> TYPE: PRT
<213> ORGANISM: Mus musculus

<400> SEQUENCE: 2

Gly Val Met Asp Ser Leu Leu Glu Ala Leu Gln Ser Gly Ala Ala Phe
1               5                   10                  15

Arg Arg Lys Arg Gly
            20
```

```
<210> SEQ ID NO 3
<211> LENGTH: 23
<212> TYPE: PRT
<213> ORGANISM: Mus musculus

<400> SEQUENCE: 3

Gly Val Met Asp Ser Leu Leu Glu Ala Leu Gln Ser Gly Ala Ala Phe
1               5                   10                  15

Arg Asp Arg Arg Lys Arg Ile
            20

<210> SEQ ID NO 4
<211> LENGTH: 23
<212> TYPE: PRT
<213> ORGANISM: Mus musculus

<400> SEQUENCE: 4

Gly Val Met Asp Ser Leu Leu Glu Ala Leu Gln Ser Gly Ala Ala Phe
1               5                   10                  15

Arg Asp Arg Arg Lys Arg Thr
            20

<210> SEQ ID NO 5
<211> LENGTH: 27
<212> TYPE: PRT
<213> ORGANISM: Mus musculus

<400> SEQUENCE: 5

Gly Val Met Asp Ser Leu Leu Glu Ala Leu Gln Thr Gly Ser Ala Phe
1               5                   10                  15

Gly Gln Arg Asn Arg Gln Ala Arg Arg Gln Arg
            20                  25

<210> SEQ ID NO 6
<211> LENGTH: 27
<212> TYPE: PRT
<213> ORGANISM: Mus musculus

<400> SEQUENCE: 6

Ala Val Met Asp Lys Leu Leu Glu Gln Leu Lys Asn Ala Gly Pro Ala
1               5                   10                  15

Lys Ser Asp Pro Ser Ser Ala Arg Lys Arg Ala
            20                  25

<210> SEQ ID NO 7
<211> LENGTH: 27
<212> TYPE: PRT
<213> ORGANISM: Mus musculus

<400> SEQUENCE: 7

Gly Ala Met Asp Ser Leu Leu Glu Lys Leu Arg Ala Ala Ala Pro Gln
1               5                   10                  15

Ala Lys Asp Gln Arg Asp Arg Arg Arg Ala
            20                  25

<210> SEQ ID NO 8
<211> LENGTH: 1171
<212> TYPE: PRT
<213> ORGANISM: Mus musculus

<400> SEQUENCE: 8

Met Glu Arg His Arg Ala Arg Ala Leu Gly Arg Asp Ser Lys Ser Ser
```

-continued

```
1               5                   10                  15

Arg Arg Lys Gly Leu Gln Ser Ala Pro Ala Gly Pro Tyr Glu Pro
            20                  25                  30

Gly Glu Lys Arg Pro Lys Leu His Leu Asn Ile Arg Thr Leu Thr Asp
            35                  40                  45

Asp Met Leu Asp Lys Phe Ala Ser Ile Arg Ile Pro Gly Ser Lys Lys
            50                  55                  60

Glu Arg Pro Pro Leu Pro His Leu Lys Thr Val Ser Gly Ile Ser Asp
65                  70                  75                  80

Ser Ser Ser Leu Ser Ser Glu Thr Met Glu Asn Asn Pro Lys Ala Leu
                85                  90                  95

Pro Glu Ser Glu Val Leu Lys Leu Phe Glu Lys Met Met Glu Asp Met
                100                 105                 110

Asn Leu Asn Glu Asp Lys Lys Ala Pro Leu Arg Glu Lys Asp Phe Gly
            115                 120                 125

Ile Lys Lys Glu Met Val Met Gln Tyr Ile Asn Thr Ala Ser Lys Thr
            130                 135                 140

Gly Ser Leu Arg Ser Ser Arg Gln Ile Ser Pro Gln Glu Phe Leu His
145                 150                 155                 160

Glu Leu Lys Met Gly Tyr Thr Asp Glu Arg Leu Phe Thr Tyr Leu Glu
                165                 170                 175

Ser Leu Arg Val Ser Leu Thr Ser His Pro Val Ser Trp Val Gln Ser
                180                 185                 190

Phe Gly His Glu Gly Leu Gly Leu Leu Leu Asp Ile Leu Glu Lys Leu
            195                 200                 205

Ile Asn Gly Gln Ile Gln Glu Lys Val Val Lys Thr Gln His Lys
            210                 215                 220

Val Ile Gln Cys Leu Arg Ala Leu Met Asn Thr Gln Tyr Gly Leu Glu
225                 230                 235                 240

Arg Ile Met Ser Asp Lys Arg Ser Leu Ser Leu Leu Ala Lys Ala Met
                245                 250                 255

Asp Pro Arg Gln Pro Ala Met Met Ala Asp Val Val Lys Leu Leu Ser
                260                 265                 270

Ala Val Cys Ile Val Gly Glu Glu Ser Ile Leu Glu Glu Val Leu Glu
            275                 280                 285

Ala Leu Thr Ser Ala Gly Glu Glu Arg Lys Ile Asp Arg Phe Phe Ser
            290                 295                 300

Ile Val Glu Gly Leu Arg His Asn Ser Val Asn Leu Gln Val Ala Cys
305                 310                 315                 320

Met Gln Leu Ile Asn Ala Leu Val Thr Ser Pro Asp Asp Leu Asp Phe
                325                 330                 335

Arg Leu His Leu Arg Asn Glu Phe Met Arg Cys Gly Leu Lys Glu Ile
            340                 345                 350

Leu Pro Asn Leu Lys Gly Ile Lys Asn Asp Gly Leu Asp Ile Gln Leu
            355                 360                 365

Lys Val Phe Asp Glu His Lys Glu Glu Asp Leu Ser Glu Phe Phe His
            370                 375                 380

Arg Leu Glu Asp Ile Arg Ala Glu Leu Asp Glu Ala Ser Asp Val Tyr
385                 390                 395                 400

Ser Met Leu Trp Asp Thr Val Lys Glu Thr Arg Ala Glu Gly His Phe
                405                 410                 415

Leu Ser Ile Leu Gln His Leu Leu Leu Ile Arg Asn Asp Arg Phe Ile
            420                 425                 430
```

```
Arg Glu Gln Tyr Phe Lys Leu Ile Asp Glu Cys Val Ser Gln Ile Val
                435                 440                 445

Leu His Arg Asp Gly Thr Asp Pro Asp Phe Thr Tyr Arg Lys Arg Leu
        450                 455                 460

Asp Leu Asp Leu Ser Gln Phe Val Asp Val Cys Ile Asp Gln Ala Lys
465                 470                 475                 480

Leu Asp Glu Trp Glu Lys Ala Ser Glu His Cys Lys Lys Phe Glu
                485                 490                 495

Lys Glu Cys Thr Asp His Gln Glu Thr Gln Ala Gln Leu Gln Lys Arg
                500                 505                 510

Glu Ala Lys Ile Asn Glu Leu Gln Ala Glu Leu Gln Ala Phe Lys Ser
            515                 520                 525

Gln Phe Gly Ala Leu Pro Pro Gly Thr Lys Ile Pro Leu Gln Pro Ser
        530                 535                 540

Val Glu Gly Glu Ala Gly Pro Ser Ala Leu Pro Pro Ala Pro Pro Ala
545                 550                 555                 560

Leu Ser Gly Gly Val Pro Pro Pro Pro Pro Pro Pro Pro Pro Pro Pro
                565                 570                 575

Pro Pro Leu Pro Gly Met Pro Met Pro Phe Gly Gly Pro Val Pro Pro
            580                 585                 590

Pro Pro Pro Leu Gly Phe Leu Gly Gly Gln Ser Ser Ile Pro Leu Asn
        595                 600                 605

Leu Pro Phe Gly Leu Lys Pro Lys Lys Glu Phe Lys Pro Glu Ile Ser
        610                 615                 620

Met Arg Arg Leu Asn Trp Leu Lys Ile Gly Pro Asn Glu Met Ser Glu
625                 630                 635                 640

Asn Cys Phe Trp Ile Lys Val Asn Glu Asn Lys Tyr Glu Asn Arg Asp
                645                 650                 655

Leu Leu Cys Lys Leu Glu Asn Thr Phe Cys Cys Gln Glu Lys Glu Lys
                660                 665                 670

Arg Asn Thr Asn Asp Phe Asp Glu Lys Lys Val Ile Lys Lys Arg Met
        675                 680                 685

Lys Glu Leu Lys Phe Leu Asp Pro Lys Ile Ala Gln Asn Leu Ser Ile
        690                 695                 700

Phe Leu Ser Ser Phe Arg Val Pro Tyr Glu Lys Ile Arg Thr Met Ile
705                 710                 715                 720

Leu Glu Val Asp Glu Thr Gln Leu Ser Glu Ser Met Ile Gln Asn Leu
                725                 730                 735

Ile Lys His Leu Pro Asp Glu Glu Gln Leu Lys Ser Leu Ser Gln Phe
                740                 745                 750

Arg Ser Asp Tyr Asn Ser Leu Cys Glu Pro Glu Gln Phe Ala Val Val
        755                 760                 765

Met Ser Asn Val Lys Arg Leu Arg Pro Arg Leu Ser Ala Ile Leu Phe
770                 775                 780

Lys Leu Gln Phe Glu Glu Gln Val Asn Asn Ile Lys Pro Asp Ile Met
785                 790                 795                 800

Ala Val Ser Thr Ala Cys Glu Glu Ile Lys Lys Ser Lys Gly Phe Ser
                805                 810                 815

Lys Leu Leu Glu Leu Val Leu Leu Met Gly Asn Tyr Met Asn Ala Gly
            820                 825                 830

Ser Arg Asn Ala Gln Thr Phe Gly Phe Asp Leu Ser Ser Leu Cys Lys
        835                 840                 845
```

```
Leu Lys Asp Thr Lys Ser Ala Asp Gln Lys Thr Thr Leu His Phe
    850                 855                 860
Leu Val Asp Val Cys Glu Glu Lys His Ala Asp Ile Leu His Phe Val
865                 870                 875                 880
Asp Asp Leu Ala His Leu Asp Lys Ala Ser Arg Val Ser Val Glu Met
                885                 890                 895
Leu Glu Lys Asn Val Lys Gln Met Gly Arg Gln Leu Gln Gln Leu Glu
            900                 905                 910
Lys Asn Leu Glu Thr Phe Pro Pro Glu Asp Leu His Asp Lys Phe
        915                 920                 925
Val Ile Lys Met Ser Ser Phe Val Ile Ser Ala Asn Glu Gln Tyr Glu
    930                 935                 940
Lys Leu Ser Thr Leu Leu Gly Ser Met Thr Gln Leu Tyr Gln Ser Ile
945                 950                 955                 960
Met Gly Tyr Tyr Ala Val Asp Met Lys Lys Val Ser Val Glu Phe
                965                 970                 975
Phe Asn Asp Leu Asn Asn Phe Arg Thr Ser Phe Met Leu Ala Leu Lys
            980                 985                 990
Glu Asn Ile Lys Lys Arg Glu Ala  Ala Glu Lys Glu Lys  Arg Ala Arg
        995                 1000                1005
Ile Ala  Lys Glu Arg Ala Glu  Lys Glu Arg Leu Glu  Arg Gln Gln
    1010                1015                1020
Glu Lys  Lys Arg Leu Leu Glu  Met Lys Thr Glu Gly  Asp Glu Thr
    1025                1030                1035
Gly Val  Met Asp Ser Leu Leu  Glu Ala Leu Gln Ser  Gly Ala Ala
    1040                1045                1050
Phe Arg  Asp Arg Arg Lys Arg  Thr Pro Lys Leu Lys  Asp Ile Arg
    1055                1060                1065
Gln Ser  Leu Ser Pro Met Ser  Gln Arg Pro Val Leu  Lys Val Cys
    1070                1075                1080
Asn His  Glu Asn Gln Lys Met  Gln Leu Thr Glu Gly  Ser Arg Pro
    1085                1090                1095
His His  Ser Ile Asn Cys Asn  Ser Thr Arg Thr Pro  Val Ala Lys
    1100                1105                1110
Glu Leu  Asn Tyr Asn Leu Asp  Thr His Ala Ser Thr  Gly Arg Ile
    1115                1120                1125
Lys Ala  Val Glu Lys Glu Ala  Cys Asn Ala Glu Ser  Asn Lys Lys
    1130                1135                1140
Lys Glu  Met Glu Leu Leu Gly  Ser Val Ala Lys Ser  Glu Ser Val
    1145                1150                1155
Pro Glu  Val Glu Ala Leu Leu  Ala Arg Leu Arg Ala  Leu
    1160                1165                1170

<210> SEQ ID NO 9
<211> LENGTH: 3516
<212> TYPE: DNA
<213> ORGANISM: Mus musculus

<400> SEQUENCE: 9
atggagaggc accgggcgcg cgctctcggc cgggacagca gtcgtcgcg gaggaagggc      60 ttgcagtccg cgccgcccgc tggcccctac gagcccgggg agaagcgacc caagttgcat    120
ttaaatatta gaacactgac agatgatatg ctggacaaat tgccagtat aagaattcca    180 gggagcaaga aagagagacc tccccttccc cacctgaaga ctgtgtctgg gatcagtgac    240
```

```
agctcatcac tgtcctcaga gacaatggaa acaacccaa aggcgctgcc agagagtgaa      300
gtcttgaagc tttttgagaa gatgatggaa gatatgaatt taaatgaaga taaaaaggca      360
ccattgcggg aaaaagactt cggtatcaaa aagaaatgg tgatgcagta cattaatact      420
gcttctaaga caggaagtct tagaagtagc cgacagatct cacctcagga atttctccat      480
gagctgaaaa tgggttacac agacgagaga cttttcacgt atctggagtc actccgagta      540
tcattgacca gtcatcctgt gagttgggtg caaagctttg gacacgaggg actcggatta      600
ttgctggaca ttttggaaaa actaattaat gggcaaatcc aagaaaaagt tgtgaagaag      660
actcagcaca aagtcatcca gtgtctgaga gccctgatga acacacagta tggcttagaa      720
aggattatga gtgacaagag gagtcttttcc ttgttggcaa agccatgga tcccaggcag      780 cccgctatga tggcagacgt ggtgaagctt ctgtctgcag tgtgcattgt cggcgaggaa      840
agcatccttg aagaagtgtt agaagccttg acttcagctg gagaagaaag aaagattgac      900 agatttttt ccattgtgga aggcctccgg cataactcag tgaacctgca agttgcttgt      960
atgcagctca taaatgctct cgttacatct cctgatgatt tggacttcag gcttcacctc     1020
agaaatgaat ttatgcgttg tggattgaaa gagatattgc caaacttaaa gggcattaag     1080
aatgatggcc tggatataca acttaaagtc tttgatgagc acaaagaaga gatttgagt      1140 gagttttttcc atcgccttga agacattaga gctgaacttg atgaagcatc tgatgtttac     1200
agcatgttat gggacacagt taaggaaact cgagcagagg acattttct ttctattctt      1260 cagcatctcc tgctcattcg caatgatcgt tttataagag agcagtattt caaattaatt     1320
gatgagtgtg tgtcacagat tgtattacat agagatggaa cggaccctga cttcacatac     1380
agaaaaagac tagatttgga cttaagtcag tttgtagatg tttgcataga tcaggccaaa     1440
ctagatgagt gggaagagaa agcatccgaa cattgcaaga aatttgaaaa agagtgtact     1500
gaccaccaag aaacccaggc tcaattgcag aaaagagagg caagattaa tgagcttcaa      1560 gcagagttac aagcttttaa atcccagttt ggtgccttgc cacctggtac aaaaaattcct     1620 ttgcaacctt cagtagaagg tgaagctggc ccttcagccc ttcctcctgc cccaccagca     1680
ctcagtggag gagtgccgcc tcccccaccg ccccctcctc caccacccccc accactccca     1740 ggaatgccaa tgccatttgg tggccctgta ccaccaccac ctcctctggg attcctgggt     1800
gggcaaagct ctattccatt aaacctgcca tttggtttga accaaagaa agaatttaag      1860 cctgaaatca gcatgagaag attgaattgg ttaaagatcg gaccaaatga atgtctgag      1920 aactgcttct ggatcaaagt aaatgaaaat aagtatgaaa atagggatttt gctttgtaaa     1980 cttgagaaca cttttttgttg ccaagaaaaa gagaaagga atacaatga ctttgatgag      2040 aagaaagtta ttaagaagag aatgaaggaa cttaaatttc tagatcctaa aattgctcag     2100
aacctttcaa tcttcctgag ctccttccgg gtgccatatg agaaaatcag gacgatgata     2160
ttggaagtgg atgaaacaca gttgtcagag tccatgattc agaacttaat aaagcaccttt     2220 cctgatgagg agcagttgaa gtcattgtcc cagtttagaa gtgactataa cagtttgtgt     2280
gagcctgagc agttcgctgt tgtgatgagc aatgtgaaga gactccggcc acggctcagt     2340
gctattctct ttaagcttca atttgaagag caggtgaaca acatcaaacc tgacatcatg     2400
gctgtcagta ctgcctgcga ggagatcaag aagagcaaag ctttagcaa gttgctggaa     2460 cttgtgttgc taatgggaaa ctacatgaat gctggctccc ggaatgctca aaccttcgga     2520
tttgacctta gctctctctg taactgaag gatacaaaat ctgcagatca gaaaaccaca     2580
ctcctccatt tcctggtaga tgtatgtgaa gaaaagcatg ctgacatcct tcactttgtg     2640
```

```
                                                    -continued gacgatttgg cacatttaga caaagctagc agagtctctg tagaaatgct ggaaaagaac    2700
gtgaagcaga tgggaaggca gcttcaacag cttgagaaga atttggaaac ctttccccct    2760
cctgaggact tgcatgacaa gtttgtgata aagatgtcca gcttcgttat cagtgcgaac    2820
gagcagtatg aaaaactctc cacactactg ggcagcatga cacaattgta ccagagtata    2880
atgggctact atgctgtcga catgaagaag gtttccgtgg aagagttttt taatgatctg    2940
aacaacttca gaacttcatt tatgctagca ttaaaggaaa acatcaaaaa acgagaagca    3000
gcagaaaagg agaaacgtgc caggatagcg aaagagcgag cagagaaaga gcgacttgaa    3060
cgccagcaag agaaaaagcg cttactagaa atgaaaactg agggagatga gacaggagtg    3120
atggatagtc tgctggaggc cttgcagtca ggggctgcct tccgcgacag aagaaaaagg    3180
acaccaaagc tgaaagatat tcggcagagt ctcagcccga tgtctcagag gcctgttctc    3240
aaagtttgta accatgaaaa tcagaaaatg cagttgacag aagggtcacg tccacaccac    3300
agtatcaatt gcaactccac caggactcca gtcgccaagg agcttaatta taatctagac    3360
actcatgcgt ctacagggag gatcaaggca gttgagaagg aagcctgtaa tgcagaaagc    3420
aacaaaaaaa aggaaatgga acttcttggc tctgttgcta aaagcgaatc agttcctgaa    3480
gttgaagccc tgctggcaag attacgagct ttataa                             3516
```

The invention claimed is:

1. A peptide or polypeptide consisting of the amino acid sequence
{GA}-{VA}-M-D-x-L-L-E-x-L-{KRQ}-x-{GA}-{SGA}-{AP} (SEQ ID NO:1)
wherein amino acids within a set of braces are interchangeable and x means any amino acid,
which sequence is extended at its C-terminus by a segment that is a basic motif of between about 5 and about 12 amino acids.

2. The peptide or polypeptide of claim 1 the sequence of which is selected from the group consisting of:
(a) GVMDSLLEALQSGAAFRRKRG {SEQ ID NO:2};
(b) GVMDNLLEALQSGAAFRDRRKRI {SEQ ID NO:3};
(c) GVMDSLLEALQSGAAFRDRRKRT {SEQ ID NO:4};
(d) GVMDSLLEALQTGSAFGQRNRQARRQR {SEQ ID NO:5};
(e) AVMDKLLEQLKNAGPAKSDPSSARKRA {SEQ ID NO:6}; and
(f) GAMDSLLEKLRAAAPQAKDQRDRRRRA {SEQ ID NO:7}.

3. The peptide or polypeptide of claim 1, the sequence of which is present in the mDia2 protein (SEQ ID NO:8).

4. A fusion polypeptide comprising
(a) a first peptide or polypeptide according to claim 1;
(b) optionally, a linker region; and
(c) a second polypeptide that is linked to said first peptide or polypeptide, or to said linker region, which second polypeptide is not natively linked to said first peptide or polypeptide.

5. The fusion polypeptide of claim 4 wherein said second polypeptide is glutathione-S-transferase or a fluorescent protein.

6. A fusion polypeptide comprising a linear multimer of two or more repeats of monomers of the peptide or polypeptide of claim 1 linked end to end, directly or with a linker present between said monomer repeats.

7. The polypeptide multimer of claim 6 having the formula $(P-X_m)_n-P$, wherein P is the peptide or polypeptide the amino acid sequence of which is
{GA}-{VA}-M-D-x-L-L-E-x-L-{KRQ}-x-{GA}-{SGA}-{AP} (SEQ ID NO: 1)
wherein amino acids within a set of braces are interchangeable and x means any amino acid;

X is a spacer or linker selected from the group consisting of $C_1$-$C_{20}$ alkyl, $C_1$-$C_{20}$ alkenyl, $C_1$-$C_{20}$ alkynyl, $C_1C_{20}$ polyether containing up to 9 oxygen atoms, and $Gly_z$, where z=1-10;

m=0 or 1, and n=1-100.

8. The peptide or polypeptide of claim 1 to the C-terminus of which is linked an additional peptide that promotes entry into cells.

9. The peptide or polypeptide of claim 8 wherein the additional peptide promoting entry into cells is a transduction domain of HIV Tat protein or of Antennapedia protein.

10. A method for inhibiting cell growth or for killing a cell by apoptosis, comprising introducing into a cell the peptide or polypeptide of claim 1, such that said peptide or polypeptide causes actin polymerization, stabilization of actin, stabilization of microtubules, or disruption of cytoskeletal dynamics, thereby causing said growth inhibition or apoptosis.

11. The method of claim 10, wherein said introducing is carried out in a live animal.

12. The method of claim 10, wherein said cell being inhibited or killed is a tumor cell.

13. The method of claim 10, wherein said introducing is by microinjection.

14. A method to disrupt or inhibit the intramolecular binding of a GTPase-binding domain to a Diaphanous-related formin autoregulatory domain in a cell, comprising introducing into and/or expressing in said cell the polypeptide or peptide of claim 1, wherein said peptide or polypeptide disrupts or inhibits said binding.

15. A method of inducing actin polymerization in a cell, comprising providing to said cell an effective amount of the peptide or polypeptide of claim 1, wherein said peptide or polypeptide induces actin polymerization.

* * * * *

UNITED STATES PATENT AND TRADEMARK OFFICE
CERTIFICATE OF CORRECTION

| | | |
|---|---|---|
| PATENT NO. | : 7,358,230 B2 | Page 1 of 23 |
| APPLICATION NO. | : 10/312042 | |
| DATED | : April 15, 2008 | |
| INVENTOR(S) | : Arthur S. Alberts | |

It is certified that error appears in the above-identified patent and that said Letters Patent is hereby corrected as shown below:

Column 2
Line 57 replace "are" with --is--.

Column 3
Line 39 replace "GBD's" with --GBDs--.
Line 41 replace "[" with --(--.
Line 42 replace "Watanabe." with --Watanabe,--.

Column 4
Line 9 replace "((" with --(--.
Line 18 replace "))" with --)--.
Line 36 replace "rufile" with --ruffle--.

Column 5
Line 12 replace ";]" with --];--.
Line 20 replace ";" with --.--.
Line 44 replace "form" with --from--.

Column 7
Line 30 replace "PLA" with --LPA--.
Line 33 replace "imaged" with --images--.
Line 41 replace "EGPF positive" with --EGFP-positive--.

Column 8
Line 26 replace "pEFmEGFP-DAD" with --pEF$_m$EGFP-DAD--.
Line 27 replace "pEFm-GBD" with --pEF$_m$-GBD--.
Lines 35 and 36 replace "pEFmEGFP" with --pEF$_m$EGFP-- both instances.

Signed and Sealed this
Tenth Day of May, 2011

David J. Kappos
*Director of the United States Patent and Trademark Office*

CERTIFICATE OF CORRECTION (continued)

U.S. Pat. No. 7,358,230 B2

Column 9
Line 27 replace "immunobloting" with --immunoblotting--.
Line 47 replace "is" with --are--.

Column 10
Lines 50-61 replace

DIA156/mDia3
1051      DETGVMDSLLEALQSGAAF....RDRRKRI [SEQ ID NO:3]

mDia2
1036      DETGVMDSLLEALQSGAAF....RDRRKRT [SEQ ID NO:4]

Dia
1024      TQEGVMDSLLEALQTGSAFGQRNRQARRQR [SEQ ID NO:5]

Bni1
1796      DRRAVMDKLLEQLKNAGPAKSDPSSARKRA [SEQ ID NO:6]

SepA
1583      ATSGAMDSLLEKLRAAAPQAKDQRDRRRRA [SEQ ID NO:7]

"                                                                      "

with

| DFNA1/mDia1 | 1177 | DETGVMDSLLEALQSGAAF......RRKRG [SEQ ID NO:2] |
| DIA156/mDia3 | 1051 | DETGVMDNLLEALQSGAAF....RDRRKRI [SEQ ID NO:3] |
| mDia2 | 1036 | DETGVMDSLLEALQSGAAF....RDRRKRT [SEQ ID NO:4] |
| Dia | 1024 | TQEGVMDSLLEALQTGSAFGQRNRQARRQR [SEQ ID NO:5] |
| Bni1 | 1796 | DRRAVMDKLLEQLKNAGPAKSDPSSARKRA [SEQ ID NO:6] |
| SepA | 1583 | ATSGAMDSLLEKLRAAAPQAKDQRDRRRRA [SEQ ID NO:7] |

--.

Column 10
Line 65 replace "beginnin" with --beginning--.

Column 11
Line 3 replace "008808; mDia2 - Q9Z207" with --O08808; mDia2 - Q9Z207.--.

Column 12
Line 18 replace "SMIQNLIKLI" with --SMIQNLIKHL--.

Column 15
Line 17 after "supra)" insert --.--.
Line 44 replace "weere" with --were--.
Line 51 replace "The" with --the--.

Column 16
Line 25 after "WASP" insert --.--.

Line 29 replace "were" with --was--.
Line 43 replace "art" with --an--.

Column 17
Line 18 after "in vivo" insert --.--.
Line 56 replace "cell s" with --cell is--.

Column 19
Line 37 replace "DAD" with --*DAD*--.
Line 38 replace "not" with --<u>not</u>--.
Line 39 after "formula" insert --.--.
Line 41 replace "(DAD-$X_m$)$_n$ –DAD" with --*(DAD-$X_m$)$_n$-DAD*--.
Line 48 replace "substitu0tion" with --substitution--.

Column 26
Line 47 after "of" delete --a--.

Column 27
Line 45 replace "an" with --and--.
Line 46 replace "5,278,056;" with --5,278,056).--.
Line 66 replace "organisms" with --organism--.

Column 28
Line 33 replace "((" with --(--.
Line 66 replace "cells After" with --cells. After--.

Column 29
Line 8 replace "assay, may" with --assay may--.

Column 31
Line 54 replace "Easton Pennsylvania" with --Easton, Pennsylvania-- .

Column 32
Line 29 replace "topic" with --topical--.

Column 33
Line 16 before "Sahai" insert --(--.
Line 23 before "normalize" insert --to--.

Column 34
Line 32 replace "basic residues several residues" with --basic residues. Several residues--.
Line 40 replace "Bnr1p" with --Bni1p--.

Column 35
Line 2 replace "deffered" with --differed--.

Column 35
Line 7 after "in" insert --the--.
Line 49 after "Rho" insert --.--.

Column 36
Line 25 replace "et al" (second occurrence) with --et al.,--.
Line 45 replace "inductionby" with --induction by--.
Line 66 replace "in in" with --in--.

Column 37
Line 33 replace "VI-VIII" with --VII-VIII--.
Line 65 replace "contructs" with --constructs--.

Column 38
Line 23 replace "recognising" with --recognizing--.
Line 37 after "previously" insert --in--.

Column 39
Line 5 after "known" insert --to--.
Line 11 replace "contains an Arg 3" with --contains Arg 3--.
Line 14 replace "thats" with --that--.

Column 40
Line 10 replace "analysing" with --analyzing--.

Column 41
Line 33 replace "disrup" with --disrupt--.
Line 34 replace "protusions" with --protrusions--.

Column 42
Line 32 replace "bonefide" with --bona fide--.

CERTIFICATE OF CORRECTION (continued)
U.S. Pat. No. 7,358,230 B2

Col. 44. Sequence Listing

Replace "

```
    <160>  NUMBER OF SEQ ID NOS: 9
    <210>  SEQ ID NO 1
    <211>  LENGTH: 15
    <212>  TYPE: PRT
    <213>  ORGANISM: Mus musculus
    <220>  FEATURE:
    <221>  NAME/KEY: MISC_FEATURE
    <222>  LOCATION: (1)..(1)
    <223>  OTHER INFORMATION: Xaa can be Gly or Ala
    <220>  FEATURE:
    <221>  NAME/KEY: MISC_FEATURE
    <222>  LOCATION:(2)..(2)
    <223>  OTHER INFORMATION: Xaa can be Val or  Ala
    <220>  FEATURE:
    <221>  NAME/KEY: MISC_FEATURE
    <222>  LOCATION: (5)..(5)
    <223>  OTHER INFORMATION: Xaa can be any amino acid
    <220>  FEATURE:
    <221>  NAME/KEY: MISC_FEATURE
    <222>  LOCATION:(9)..(9)
    <223>  OTHER INFORMATION: Xaa can be any amino acid
    <220>  FEATURE:
    <221>  NAME/KEY: MISC_FEATURE
    <222>  LOCATION: (11)..(11)
    <223>  OTHER INFORMATION: Xaa can be Lys, Arg or Gln
    <220>  FEATURE:
    <221>  NAME/KEY: MISC_FEATURE
    <222>  LOCATION: (12)..(12)
    <223>  OTHER INFORMATION: Xaa can be any amino acid
    <220>  FEATURE:
    <221>  NAME/KEY: MISC_FEATURE
    <222>  LOCATION: (13)..(13)

<223>  OTHER INFORMATION: Xaa can be Glu or Ala
    <220>  FEATURE:
    <221>  NAME/KEY: MISC_FEATURE
    <222>  LOCATION: (14)..(14)
    <223>  OTHER INFORMATION: Xaa can be Ser, Glu or Ala
    <220>  FEATURE:
    <221>  NAME/KEY: MISC_FEATURE
    <222>  LOCATION:(15)..(15)
    <223>  OTHER INFORMATION: Xaa can be  Ala or Pro

<400>  SEQUENCE: 1

Xaa Xaa Met Asp Xaa Leu Leu Glu Xaa Leu Xaa Xaa Xaa Xaa Xaa
    1               5                   10                  15

<210>  SEQ ID NO 2
    <211>  LENGTH: 21
    <212>  TYPE: PRT
    <213>  ORGANISM: Mus musculus

<400>  SEQUENCE: 2

Gly Val Met Asp Ser Leu Leu Glu Ala Leu Gln Ser Gly Ala Ala Phe
    1               5                   10                  15

Arg Arg Lys Arg Gly
                    20

<210>  SEQ ID NO 3
    <211>  LENGTH: 23
    <212>  TYPE: PRT
    <213>  ORGANISM: Mus musculus
```

```
<400>   SEQUENCE: 3

Gly Val Met Asp Ser Leu Leu Glu Ala Leu Gln Ser Gly Ala Ala Phe
1               5                   10                  15

Arg Asp Arg Arg Lys Arg Ile
            20

<210>   SEQ ID NO 4
<211>   LENGTH: 23
<212>   TYPE: PRT
<213>   ORGANISM: Mus musculus

<400>   SEQUENCE: 4

Gly Val Met Asp Ser Leu Leu Glu Ala Leu Gln Ser Gly Ala Ala Phe
1               5                   10                  15

Arg Asp Arg Arg Lys Arg Thr
            20

<210>   SEQUENCE: 5
<211>   LENGTH: 27
<212>   TYPE: PRT
<213>   ORGANISM: Mus musculus

<400>   SEQUENCE: 5

Gly Val Met Asp Ser Leu Leu Glu Ala Leu Gln Thr Gly Ser Ala Phe
1               5                   10                  15

Gly Gln Arg Asn Arg Gln Ala Arg Arg Gln Arg
            20                  25

<210>   SEQ ID NO 6
<211>   LENGTH: 27
<212>   TYPE: PRT
<213>   ORGANISM: Mus musculus

<400>   SEQUENCE: 6

Ala Val Met Asp Lys Leu Leu Glu Gln Leu Lys Asn Ala Gly Pro Ala
1               5                   10                  15

Lys Ser Asp Pro Ser Ser Ala Arg Lys Arg Ala
            20                  25

<210>   SEQ ID NO 7
<211>   LENGTH: 27
<212>   TYPE: PRT
<213>   ORGANISM: Mus musculus

<400>   SEQUENCE: 7

Gly Ala Met Asp Ser Leu Leu Glu Lys Leu Arg Ala Ala Ala Pro Gln
1               5                   10                  15

Ala Lys Asp Gln Arg Asp Arg Arg Arg Arg Ala
            20                  25

<210>   SEQ ID NO 8
<211>   LENGTH: 1171
<212>   TYPE: PRT
<213>   ORGANISM: Mus musculus

<400>   SEQUENCE: 8
```

```
Met Glu Arg His Arg Ala Arg Ala Leu Gly Arg Asp Ser Lys Ser Ser
1               5                   10                  15
Arg Arg Lys Gly Leu Gln Ser Ala Pro Pro Ala Gly Pro Tyr Glu Pro
            20                  25                  30
Gly Glu Lys Arg Pro Lys Leu His Leu Asn Ile Arg Thr Leu Thr Asp
            35                  40                  45
Asp Met Leu Asp Lys Phe Ala Ser Ile Arg Ile Pro Gly Ser Lys Lys
    50                  55                  60
Glu Arg Pro Pro Leu Pro His Leu Lys Thr Val Ser Gly Ile Ser Asp
65                  70                  75                      80
Ser Ser Ser Leu Ser Ser Glu Thr Met Glu Asn Asn Pro Lys Ala Leu
                85                  90                  95
Pro Glu Ser Glu Val Leu Lys Leu Phe Glu Lys Met Met Glu Asp Met
            100                 105                 110
Asn Leu Asn Glu Asp Lys Lys Ala Pro Leu Arg Glu Lys Asp Phe Gly
        115                 120                 125
Ile Lys Lys Glu Met Val Met Gln Tyr Ile Asn Thr Ala Ser Lys Thr
    130                 135                 140
Gly Ser Leu Arg Ser Ser Arg Gln Ile Ser Pro Gln Glu Phe Leu His
145                 150                 155                 160
Glu Leu Lys Met Gly Tyr Thr Asp Glu Arg Leu Phe Thr Tyr Leu Glu
                165                 170                 175
Ser Leu Arg Val Ser Leu Thr Ser His Pro Val Ser Trp Val Gln Ser
            180                 185                 190
Phe Gly His Glu Gly Leu Gly Leu Leu Leu Asp Ile Leu Glu Lys Leu
        195                 200                 205
Ile Asn Gly Gln Ile Gln Glu Lys Val Val Lys Thr Gln His Lys
    210                 215                 220
Val Ile Gln Cys Leu Arg Ala Leu Met Asn Thr Gln Tyr Gly Leu Glu
225                 230                 235                 240
Arg Ile Met Ser Asp Lys Arg Ser Leu Ser Leu Leu Ala Lys Ala Met
            245                 250                 255
Asp Pro Arg Gln Pro Ala Met Met Ala Asp Val Val Lys Leu Leu Ser
            260                 265                 270
Ala Val Cys Ile Val Gly Glu Glu Ser Ile Leu Glu Glu Val Leu Glu
        275                 280                 285
Ala Leu Thr Ser Ala Gly Glu Glu Arg Lys Ile Asp Arg Phe Phe Ser
        290                 295                 300
Ile Val Glu Gly Leu Arg His Asn Ser Val Asn Leu Gln Val Ala Cys
305                 310                 315                 320
Met Gln Leu Ile Asn Ala Leu Val Thr Ser Pro Asp Asp Leu Asp Phe
            325                 330                 335
Arg Leu His Leu Arg Asn Glu Phe Met Arg Cys Gly Leu Lys Glu Ile
            340                 345                 350
Leu Pro Asn Leu Lys Gly Ile Lys Asn Asp Gly Leu Asp Ile Gln Leu
        355                 360                 365
Lys Val Phe Asp Glu His Lys Glu Glu Asp Leu Ser Glu Phe Phe His
    370                 375                 380
```

```
Arg Leu Glu Asp Ile Arg Ala Glu Leu Asp Glu Ala Ser Asp Val Tyr
385                 390                 395                 400

Ser Met Leu Trp Asp Thr Val Lys Glu Thr Arg Ala Glu Gly His Phe
                405                 410                 415

Leu Ser Ile Leu Gln His Leu Leu Leu Ile Arg Asn Asp Arg Phe Ile
            420                 425                 430

Arg Glu Gln Tyr Phe Lys Leu Ile Asp Glu Cys Val Ser Gln Ile Val
        435                 440                 445

Leu His Arg Asp Gly Thr Asp Pro Asp Phe Thr Tyr Arg Lys Arg Leu
    450                 455                 460

Asp Leu Asp Leu Ser Gln Phe Val Asp Val Cys Ile Asp Gln Ala Lys
465                 470                 475                 480

Leu Asp Glu Trp Glu Lys Ala Ser Glu His Cys Lys Lys Phe Glu
                485                 490                 495

Lys Glu Cys Thr Asp His Gln Glu Thr Gln Ala Gln Leu Gln Lys Arg
            500                 505                 510

Glu Ala Lys Ile Asn Glu Leu Gln Ala Glu Leu Gln Ala Phe Lys Ser
        515                 520                 525

Gln Phe Gly Ala Leu Pro Pro Gly Thr Lys Ile Pro Leu Gln Pro Ser
    530                 535                 540

Val Glu Gly Glu Ala Gly Pro Ser Ala Leu Pro Pro Ala Pro Pro Ala
545                 550                 555                 560

Leu Ser Gly Gly Val Pro Pro Pro Pro Pro Pro Pro Pro Pro Pro Pro
                565                 570                 575

Pro Pro Leu Pro Gly Met Pro Met Pro Phe Gly Gly Pro Val Pro Pro
            580                 585                 590

Pro Pro Pro Leu Gly Phe Leu Gly Gly Gln Ser Ser Ile Pro Leu Asn
        595                 600                 605

Leu Pro Phe Gly Leu Lys Pro Lys Lys Glu Phe Lys Pro Glu Ile Ser
    610                 615                 620

Met Arg Arg Leu Asn Trp Leu Lys Ile Gly Pro Asn Glu Met Ser Glu
625                 630                 635                 640

Asn Cys Phe Trp Ile Lys Val Asn Glu Asn Lys Tyr Glu Asn Arg Asp
                645                 650                 655

Leu Leu Cys Lys Leu Glu Asn Thr Phe Cys Cys Gln Glu Lys Glu Lys
            660                 665                 670

Arg Asn Thr Asn Asp Phe Asp Glu Lys Lys Val Ile Lys Lys Arg Met
        675                 680                 685

Lys Glu Leu Lys Phe Leu Asp Pro Lys Ile Ala Gln Asn Leu Ser Ile
    690                 695                 700

Phe Leu Ser Ser Phe Arg Val Pro Tyr Glu Lys Ile Arg Thr Met Ile
705                 710                 715                 720

Leu Glu Val Asp Glu Thr Gln Leu Ser Glu Ser Met Ile Gln Asn Leu
                725                 730                 735

Ile Lys His Leu Pro Asp Glu Glu Gln Leu Lys Ser Leu Ser Gln Phe
            740                 745                 750

Arg Ser Asp Tyr Asn Ser Leu Cys Glu Pro Glu Gln Phe Ala Val Val
        755                 760                 765
```

```
Met Ser Asn Val Lys Arg Leu Arg Pro Arg Leu Ser Ala Ile Leu Phe
    770             775             780
Lys Leu Gln Phe Glu Glu Gln Val Asn Asn Ile Lys Pro Asp Ile Met
785             790             795                         800
Ala Val Ser Thr Ala Cys Glu Glu Ile Lys Lys Ser Lys Gly Phe Ser
                805             810                 815
Lys Leu Leu Glu Leu Val Leu Leu Met Gly Asn Tyr Met Asn Ala Gly
            820             825                 830
Ser Arg Asn Ala Gln Thr Phe Gly Phe Asp Leu Ser Ser Leu Cys Lys
        835             840             845
Leu Lys Asp Thr Lys Ser Ala Asp Gln Lys Thr Thr Leu Leu His Phe
    850             855             860
Leu Val Asp Val Cys Glu Glu Lys His Ala Asp Ile Leu His Phe Val
865             870             875                         880
Asp Asp Leu Ala His Leu Asp Lys Ala Ser Arg Val Ser Val Glu Met
                885             890                 895
Leu Glu Lys Asn Val Lys Gln Met Gly Arg Gln Leu Gln Gln Leu Glu
            900             905                 910
Lys Asn Leu Glu Thr Phe Pro Pro Pro Glu Asp Leu His Asp Lys Phe
    915             920             925
Val Ile Lys Met Ser Ser Phe Val Ile Ser Ala Asn Glu Gln Tyr Glu
930             935             940
Lys Leu Ser Thr Leu Leu Gly Ser Met Thr Gln Leu Tyr Gln Ser Ile
945             950             955                     960
 Met Gly Tyr Tyr Ala Val Asp Met Lys Lys Val Ser Val Glu Glu Phe
                965             970                 975
 Phe Asn Asp Leu Asn Asn Phe Arg Thr Ser Phe Met Leu Ala Leu Lys
                980             985             990
 Glu Asn Ile Lys Lys Arg Glu Ala  Ala Glu Lys Glu Lys  Arg Ala Arg
            995             1000            1005
 Ile Ala  Lys Glu Arg Ala Glu  Lys Glu Arg Leu Glu  Arg Gln Gln
    1010            1015           1020
 Glu Lys  Lys Arg Leu Leu Glu  Met Lys Thr Glu Gly  Asp Glu Thr
    1025            1030           1035
 Gly Val  Met Asp Ser Leu Leu  Glu Ala Leu Gln Ser  Gly Ala Ala
    1040            1045           1050
 Phe Arg  Asp Arg Arg Lys Arg  Thr Pro Lys Leu Lys  Asp Ile Arg
    1055            1060           1065
 Gln Ser  Leu Ser Pro Met Ser  Gln Arg Pro Val Leu  Lys Val Cys
    1070            1075           1080
 Asn His  Glu Asn Gln Lys Met  Gln Leu Thr Glu Gly  Ser Arg Pro
    1085            1090           1095
 His His  Ser Ile Asn Cys Asn  Ser Thr Arg Thr Pro  Val Ala Lys
    1100            1105           1110
 Glu Leu  Asn Tyr Asn Leu Asp  Thr His Ala Ser Thr  Gly Arg Ile
    1115            1120           1125
 Lys Ala  Val Glu Lys Glu Ala  Cys Asn Ala Glu Ser  Asn Lys Lys
    1130            1135           1140
```

```
Lys Glu  Met Glu Leu Leu  Gly Ser Val Ala Lys  Ser Glu Ser Val
    1145             1150                1155

Pro Glu  Val Glu Ala Leu  Leu Ala Arg Leu Arg  Ala Leu
    1160             1165                1170
```

<210> SEQ ID NO 9
<211> LENGTH: 3516
<212> TYPE: DNA
<213> ORGANISM: Mus musculus

<400> SEQUENCE: 9

```
atggagaggc accgggcgcg cgctctcggc cgggacagca agtcgtcgcg gaggaagggc      60
ttgcagtccg cgccgcccgc tggcccctac gagcccgggg agaagcgacc caagttgcat     120
ttaaatatta gaacactgac agatgatatg ctggacaaat ttgccagtat aagaattcca     180
gggagcaaga aagagagacc tccccttccc cacctgaaga ctgtgtctgg gatcagtgac     240
agctcatcac tgtcctcaga gacaatggaa acaacccaa aggcgctgcc agagagtgaa      300
gtcttgaagc tttttgagaa gatgatggaa gatatgaatt taaatgaaga taaaaaggca     360
ccattgcggg aaaaagactt cggtatcaaa aagaaatgg tgatgcagta cattaatact      420
gcttctaaga caggaagtct tagaagtagc cgacagatct caccctcagga atttctccat    480
gagctgaaaa tgggttacac agacgagaga cttttcacgt atctggagtc actccgagta    540
tcattgacca gtcatcctgt gagttgggtg caaagctttg gacacgaggg actcggatta    600
ttgctggaca ttttggaaaa actaattaat gggcaaatcc aagaaaaagt tgtgaagaag    660
actcagcaca aagtcatcca gtgtctgaga gccctgatga cacacagta tggcttagaa     720
aggattatga gtgacaagag gagtctttcc ttgttggcaa aagccatgga tcccaggcag    780
cccgctatga tggcagacgt ggtgaagctt ctgtctgcag tgtgcattgt cggcgaggaa    840
agcatccttg aagaagtgtt agaagccttg acttcagctg agaagaaag aaagattgac     900
agatttttt ccattgtgga aggcctccgg cataactcag tgaacctgca agttgcttgt     960
atgcagctca taatgctct cgttacatct cctgatgatt tggacttcag gcttcacctc    1020
agaaatgaat ttatgcgttg tggattgaaa gagatattgc caaacttaaa gggcattaag    1080
aatgatggcc tggatataca acttaaagtc tttgatgagc acaagaaga agatttgagt    1140
gagtttttcc atcgccttga agacattaga gctgaacttg atgaagcatc tgatgtttac    1200
agcatgttat gggacacagt taaggaaact cgagcagagg gacattttct ttctattctt    1260
cagcatctcc tgctcattcg caatgatcgt tttataagag agcagtattt caaattaatt    1320
gatgagtgtg tgtcacagat tgtattacat agagatggaa cggaccctga cttcacatac    1380
agaaaaagac tagatttgga cttaagtcag tttgtagatg tttgcataga tcaggccaaa    1440
ctagatgagt gggaagagaa agcatccgaa cattgcaaga aatttgaaaa agagtgtact    1500
gaccaccaag aaacccaggc tcaattgcag aaaagagagg caaagattaa tgagcttcaa    1560
gcagagttac aagcttttaa atcccagttt ggtgccttgc acctggtac aaaaattcct    1620
ttgcaacctt cagtagaagg tgaagctggc ccttcagccc ttcctcctgc cccaccagca    1680
ctcagtggag gagtgccgcc tcccccaccg ccccctcctc caccacccc accactccca    1740
ggaatgccaa tgccatttgg tggccctgta ccaccaccac ctcctctggg attcctgggt    1800
```

```
gggcaaagct ctattccatt aaacctgcca tttggtttga aaccaaagaa agaatttaag    1860
cctgaaatca gcatgagaag attgaattgg ttaaagatcg gaccaaatga atgtctgag    1920 aactgcttct ggatcaaagt aaatgaaaat aagtatgaaa atagggattt gctttgtaaa   1980
cttgagaaca cttttgttg ccaagaaaaa gagaaaagga atacaaatga ctttgatgag    2040
aagaaagtta ttaagaagag aatgaaggaa cttaaatttc tagatcctaa aattgctcag   2100
aacctttcaa tcttcctgag ctccttccgg gtgccatatg agaaaatcag gacgatgata   2160
ttggaagtgg atgaaacaca gttgtcagag tccatgattc agaacttaat aaagcacctt   2220
cctgatgagg agcagttgaa gtcattgtcc cagtttagaa gtgactataa cagtttgtgt   2280
gagcctgagc agttcgctgt tgtgatgagc aatgtgaaga gactccggcc acggctcagt   2340
gctattctct ttaagcttca atttgaagag caggtgaaca acatcaaacc tgacatcatg   2400
gctgtcagta ctgcctgcga ggagatcaag aagagcaaag ctttagcaa gttgctggaa   2460 cttgtgttgc taatgggaaa ctacatgaat gctggctccc ggaatgctca accttcgga    2520 tttgaccta gctctctctg taaactgaag gatacaaaat ctgcagatca gaaaaccaca    2580
ctcctccatt tcctggtaga tgtatgtgaa gaaaagcatg ctgacatcct tcactttgtg   2640
gacgatttgg cacatttaga caaagctagc agagtctctg tagaaatgct ggaaaagaac   2700
gtgaagcaga tgggaaggca gcttcaacag cttgagaaga atttggaaac ctttcccccct  2760 cctgaggact tgcatgacaa gtttgtgata aagatgtcca gcttcgttat cagtgcgaac   2820
gagcagtatg aaaaactctc cacactactg ggcagcatga cacaattgta ccagagtata   2880
  atgggctact atgctgtcga catgaagaag gtttccgtgg aagagttttt taatgatctg    2940
  aacaacttca gaacttcatt tatgctagca ttaaaggaaa acatcaaaaa acgagaagca    3000
  gcagaaaagg agaaacgtgc caggatagcg aaagagcgag cagagaaaga gcgacttgaa   3060
  cgccagcaag agaaaaagcg cttactagaa atgaaaactg agggagatga gacaggagtg   3120
  atggatagtc tgctggaggc cttgcagtca ggggctgcct tccgcgacag aagaaaaagg   3180
  acaccaaagc tgaaagatat tcggcagagt ctcagcccga tgtctcagag gcctgttctc    3240
  aaagtttgta accatgaaaa tcagaaaatg cagttgacag aagggtcacg tccacaccac   3300
  agtatcaatt gcaactccac caggactcca gtcgccaagg agcttaatta taatctagac   3360
  actcatgcgt ctacagggag gatcaaggca gttgagaagg aagcctgtaa tgcagaaagc   3420
  aacaaaaaaa aggaaatgga acttcttggc tctgttgcta aaagcgaatc agttcctgaa   3480
    gttgaagccc tgctggcaag attacgagct ttataa                              3516
```
"

with--

```
                           SEQUENCE LISTING

<110>  ALBERTS, Arthur

<120>  CONSERVED DIAPHANOUS-RELATED FORMIN AUTOREGULATORY DOMAIN (DAD)

<130>  VAN67 P320

<140>  10/312,042

<141>  2002-12-23

<150>  PCT/US01/17347

<151>  2001-06-22

<150>  US 60/213,275

<151>  2000-06-22

<160>  27

<170>  PatentIn version 3.1

<210>  1
      <211>  15
      <212>  PRT
      <213>  Mus musculus
      <220>
      <221>  MISC_FEATURE
      <222>  (1)..(1)
      <223>  Xaa can be Gly or Ala
      <220>
      <221>  MISC_FEATURE
      <222>  (2)..(2)
      <223>  Xaa can be Val or  Ala
      <220>
      <221>  MISC_FEATURE
      <222>  (5)..(5)
      <223>  Xaa can be any amino acid
      <220>
      <221>  MISC_FEATURE
      <222>  (9)..(9)
      <223>  Xaa can be any amino acid
```

```
<220>
<221>  MISC_FEATURE
<222>  (11)..(11)
<223>  Xaa can be Lys, Arg or Gln
<220>
<221>  MISC_FEATURE
<222>  (12)..(12)
<223>  Xaa can be any amino acid
<220>
<221>  MISC_FEATURE
<222>  (13)..(13)
<223>  Xaa can be Glu or Ala <220>
<221>  MISC_FEATURE
<222>  (14)..(14)
<223>  Xaa can be Ser, Glu or Ala
<220>
<221>  MISC_FEATURE
<222>  (15)..(15)
<223>  Xaa can be  Ala or Pro

<400>  1

Xaa Xaa Met Asp Xaa Leu Leu Glu Xaa Leu Xaa Xaa Xaa Xaa Xaa
1               5                   10                  15

<210>  2
<211>  21
<212>  PRT

<213>  Mus musculus

<400>  2

Gly Val Met Asp Ser Leu Leu Glu Ala Leu Gln Ser Gly Ala Ala Phe
1               5                   10                  15

Arg Arg Lys Arg Gly
                20
<210>  3
<211>  23
<212>  PRT
<213>  Mus musculus

<400>  3

Gly Val Met Asp Asn Leu Leu Glu Ala Leu Gln Ser Gly Ala Ala Phe
1               5                   10                  15

Arg Asp Arg Arg Lys Arg Ile
                20

<210>  4
<211>  23
<212>  PRT
<213>  Mus musculus

<400>  4

Gly Val Met Asp Ser Leu Leu Glu Ala Leu Gln Ser Gly Ala Ala Phe
1               5                   10                  15

Arg Asp Arg Arg Lys Arg Thr
                20
```

<210> 5
<211> 27
<212> PRT
<213> Mus musculus

<400> 5

Gly Val Met Asp Ser Leu Leu Glu Ala Leu Gln Thr Gly Ser Ala Phe
1               5                   10                  15

Gly Gln Arg Asn Arg Gln Ala Arg Arg Gln Arg
            20                  25

<210> 6
<211> 27
<212> PRT
<213> Mus musculus

<400> 6

Ala Val Met Asp Lys Leu Leu Glu Gln Leu Lys Asn Ala Gly Pro Ala
1               5                   10                  15

Lys Ser Asp Pro Ser Ser Ala Arg Lys Arg Ala
            20                  25

<210> 7
<211> 27
<212> PRT
<213> Mus musculus

<400> 7

Gly Ala Met Asp Ser Leu Leu Glu Lys Leu Arg Ala Ala Ala Pro Gln
1               5                   10                  15

Ala Lys Asp Gln Arg Asp Arg Arg Arg Arg Ala
            20                  25

<210> 8
<211> 1171
<212> PRT
<213> Mus musculus

<400> 8

Met Glu Arg His Arg Ala Arg Ala Leu Gly Arg Asp Ser Lys Ser Ser
1               5                   10                  15

Arg Arg Lys Gly Leu Gln Ser Ala Pro Pro Ala Gly Pro Tyr Glu Pro
            20                  25                  30

Gly Glu Lys Arg Pro Lys Leu His Leu Asn Ile Arg Thr Leu Thr Asp
        35                  40                  45

Asp Met Leu Asp Lys Phe Ala Ser Ile Arg Ile Pro Gly Ser Lys Lys
    50                  55                  60

Glu Arg Pro Pro Leu Pro His Leu Lys Thr Val Ser Gly Ile Ser Asp
65                  70                  75                  80

Ser Ser Ser Leu Ser Ser Glu Thr Met Glu Asn Asn Pro Lys Ala Leu
                85                  90                  95

Pro Glu Ser Glu Val Leu Lys Leu Phe Glu Lys Met Met Glu Asp Met
            100                 105                 110

Asn Leu Asn Glu Asp Lys Lys Ala Pro Leu Arg Glu Lys Asp Phe Gly
        115                 120                 125

Ile Lys Lys Glu Met Val Met Gln Tyr Ile Asn Thr Ala Ser Lys Thr

```
                130                      135                      140
    Gly Ser Leu Arg Ser Ser Arg Gln Ile Ser Pro Gln Glu Phe Leu His
    145                 150                 155                 160

Glu Leu Lys Met Gly Tyr Thr Asp Glu Arg Leu Phe Thr Tyr Leu Glu
                    165                 170                 175

Ser Leu Arg Val Ser Leu Thr Ser His Pro Val Ser Trp Val Gln Ser
                    180                 185                 190

Phe Gly His Glu Gly Leu Gly Leu Leu Leu Asp Ile Leu Glu Lys Leu
                195                 200                 205

Ile Asn Gly Gln Ile Gln Glu Lys Val Val Lys Thr Gln His Lys
        210                 215                 220

Val Ile Gln Cys Leu Arg Ala Leu Met Asn Thr Gln Tyr Gly Leu Glu
    225                 230                 235                 240

Arg Ile Met Ser Asp Lys Arg Ser Leu Ser Leu Leu Ala Lys Ala Met
                    245                 250                 255

Asp Pro Arg Gln Pro Ala Met Met Ala Asp Val Val Lys Leu Leu Ser
                260                 265                 270

Ala Val Cys Ile Val Gly Glu Glu Ser Ile Leu Glu Glu Val Leu Glu
                275                 280                 285

Ala Leu Thr Ser Ala Gly Glu Glu Arg Lys Ile Asp Arg Phe Phe Ser
                290                 295                 300

Ile Val Glu Gly Leu Arg His Asn Ser Val Asn Leu Gln Val Ala Cys
    305                 310                 315                 320

Met Gln Leu Ile Asn Ala Leu Val Thr Ser Pro Asp Asp Leu Asp Phe
                    325                 330                 335

Arg Leu His Leu Arg Asn Glu Phe Met Arg Cys Gly Leu Lys Glu Ile
                    340                 345                 350

Leu Pro Asn Leu Lys Gly Ile Lys Asn Asp Gly Leu Asp Ile Gln Leu
                355                 360                 365

Lys Val Phe Asp Glu His Lys Glu Glu Asp Leu Ser Glu Phe Phe His
        370                 375                 380

Arg Leu Glu Asp Ile Arg Ala Glu Leu Asp Glu Ala Ser Asp Val Tyr
    385                 390                 395                 400

Ser Met Leu Trp Asp Thr Val Lys Glu Thr Arg Ala Glu Gly His Phe
                    405                 410                 415

Leu Ser Ile Leu Gln His Leu Leu Leu Ile Arg Asn Asp Arg Phe Ile
                420                 425                 430

Arg Glu Gln Tyr Phe Lys Leu Ile Asp Glu Cys Val Ser Gln Ile Val
                435                 440                 445

Leu His Arg Asp Gly Thr Asp Pro Asp Phe Thr Tyr Arg Lys Arg Leu
        450                 455                 460

Asp Leu Asp Leu Ser Gln Phe Val Asp Val Cys Ile Asp Gln Ala Lys
    465                 470                 475                 480

Leu Asp Glu Trp Glu Glu Lys Ala Ser Glu His Cys Lys Lys Phe Glu
                    485                 490                 495

Lys Glu Cys Thr Asp His Gln Glu Thr Gln Ala Gln Leu Gln Lys Arg
                500                 505                 510
```

```
Glu Ala Lys Ile Asn Glu Leu Gln Ala Glu Leu Gln Ala Phe Lys Ser
        515                 520                 525

Gln Phe Gly Ala Leu Pro Pro Gly Thr Lys Ile Pro Leu Gln Pro Ser
    530                 535                 540

Val Glu Gly Glu Ala Gly Pro Ser Ala Leu Pro Pro Ala Pro Pro Ala
545                 550                 555                 560

Leu Ser Gly Gly Val Pro Pro Pro Pro Pro Pro Pro Pro Pro Pro Pro
                565                 570                 575

Pro Pro Leu Pro Gly Met Pro Met Pro Phe Gly Gly Pro Val Pro Pro
            580                 585                 590

Pro Pro Pro Leu Gly Phe Leu Gly Gly Ser Ser Ile Pro Leu Asn
            595                 600                 605

Leu Pro Phe Gly Leu Lys Pro Lys Lys Glu Phe Lys Pro Glu Ile Ser
        610                 615                 620

Met Arg Arg Leu Asn Trp Leu Lys Ile Gly Pro Asn Glu Met Ser Glu
625                 630                 635                 640

Asn Cys Phe Trp Ile Lys Val Asn Glu Asn Lys Tyr Glu Asn Arg Asp
                645                 650                 655

Leu Leu Cys Lys Leu Glu Asn Thr Phe Cys Cys Gln Glu Lys Glu Lys
            660                 665                 670

Arg Asn Thr Asn Asp Phe Asp Glu Lys Lys Val Ile Lys Lys Arg Met
        675                 680                 685

Lys Glu Leu Lys Phe Leu Asp Pro Lys Ile Ala Gln Asn Leu Ser Ile
    690                 695                 700

Phe Leu Ser Ser Phe Arg Val Pro Tyr Glu Lys Ile Arg Thr Met Ile
705                 710                 715                 720

Leu Glu Val Asp Glu Thr Gln Leu Ser Glu Ser Met Ile Gln Asn Leu
                725                 730                 735

Ile Lys His Leu Pro Asp Glu Glu Gln Leu Lys Ser Leu Ser Gln Phe
            740                 745                 750

Arg Ser Asp Tyr Asn Ser Leu Cys Glu Pro Glu Gln Phe Ala Val Val
        755                 760                 765

Met Ser Asn Val Lys Arg Leu Arg Pro Arg Leu Ser Ala Ile Leu Phe
    770                 775                 780

Lys Leu Gln Phe Glu Glu Gln Val Asn Asn Ile Lys Pro Asp Ile Met
785                 790                 795                 800

Ala Val Ser Thr Ala Cys Glu Glu Ile Lys Lys Ser Lys Gly Phe Ser
                805                 810                 815

Lys Leu Leu Glu Leu Val Leu Leu Met Gly Asn Tyr Met Asn Ala Gly
            820                 825                 830

Ser Arg Asn Ala Gln Thr Phe Gly Phe Asp Leu Ser Ser Leu Cys Lys
        835                 840                 845

Leu Lys Asp Thr Lys Ser Ala Asp Gln Lys Thr Thr Leu Leu His Phe
    850                 855                 860

Leu Val Asp Val Cys Glu Glu Lys His Ala Asp Ile Leu His Phe Val
865                 870                 875                 880

Asp Asp Leu Ala His Leu Asp Lys Ala Ser Arg Val Ser Val Glu Met
                885                 890                 895
```

```
    Leu Glu Lys Asn Val Lys Gln Met Gly Arg Gln Leu Gln Gln Leu Glu
                    900                 905                 910

Lys Asn Leu Glu Thr Phe Pro Pro Pro Glu Asp Leu His Asp Lys Phe
                915                 920                 925

Val Ile Lys Met Ser Ser Phe Val Ile Ser Ala Asn Glu Gln Tyr Glu
            930                 935                 940

Lys Leu Ser Thr Leu Leu Gly Ser Met Thr Gln Leu Tyr Gln Ser Ile
    945                 950                 955                 960

Met Gly Tyr Tyr Ala Val Asp Met Lys Lys Val Ser Val Glu Glu Phe
                    965                 970                 975

Phe Asn Asp Leu Asn Asn Phe Arg Thr Ser Phe Met Leu Ala Leu Lys
                980                 985                 990

Glu Asn Ile Lys Lys Arg Glu Ala  Ala Glu Lys Glu Lys Arg Ala Arg
                995                 1000                1005

Ile Ala  Lys Glu Arg Ala Glu  Lys Glu Arg Leu Glu  Arg Gln Gln
        1010                1015                1020

Glu Lys  Lys Arg Leu Leu Glu  Met Lys Thr Glu Gly  Asp Glu Thr
        1025                1030                1035

Gly Val  Met Asp Ser Leu Leu  Glu Ala Leu Gln Ser  Gly Ala Ala
        1040                1045                1050

Phe Arg  Asp Arg Arg Lys Arg  Thr Pro Lys Leu Lys  Asp Ile Arg
        1055                1060                1065

Gln Ser  Leu Ser Pro Met Ser  Gln Arg Pro Val Leu  Lys Val Cys
        1070                1075                1080

Asn His  Glu Asn Gln Lys Met  Gln Leu Thr Glu Gly  Ser Arg Pro
        1085                1090                1095

His His  Ser Ile Asn Cys Asn  Ser Thr Arg Thr Pro  Val Ala Lys
        1100                1105                1110

Glu Leu  Asn Tyr Asn Leu Asp  Thr His Ala Ser Thr  Gly Arg Ile
        1115                1120                1125

Lys Ala  Val Glu Lys Glu Ala  Cys Asn Ala Glu Ser  Asn Lys Lys
        1130                1135                1140

Lys Glu  Met Glu Leu Leu Gly  Ser Val Ala Lys Ser  Glu Ser Val
        1145                1150                1155

Pro Glu  Val Glu Ala Leu Leu  Ala Arg Leu Arg Ala  Leu
        1160                1165                1170

<210>  9
<211>  3516
<212>  DNA
<213>  Mus musculus

<400>  9
atggagaggc accgggcgcg cgctctcggc cgggacagca agtcgtcgcg gaggaagggc    60
ttgcagtccg cgccgcccgc tggcccctac gagcccgggg agaagcgacc caagttgcat   120
ttaaatatta gaacactgac agatgatatg ctggacaaat tgccagtat aagaattcca    180 gggagcaaga aagagagacc tccccttccc cacctgaaga ctgtgtctgg atcagtgac   240 agctcatcac tgtcctcaga gacaatggaa acaacccaa aggcgctgcc agagagtgaa   300
```

```
gtcttgaagc tttttgagaa gatgatggaa gatatgaatt taaatgaaga taaaaaggca    360
ccattgcggg aaaaagactt cggtatcaaa aaagaaatgg tgatgcagta cattaatact    420
gcttctaaga caggaagtct tagaagtagc cgacagatct cacctcagga atttctccat    480
gagctgaaaa tgggttacac agacgagaga cttttcacgt atctggagtc actccgagta    540
tcattgacca gtcatcctgt gagttgggtg caaagctttg gacacgaggg actcggatta    600
ttgctggaca ttttggaaaa actaattaat gggcaaatcc aagaaaagt tgtgaagaag     660
actcagcaca aagtcatcca gtgtctgaga gccctgatga acacacagta tggcttagaa    720
aggattatga gtgacaagag gagtctttcc ttgttggcaa aagccatgga tccaggcag    780
cccgctatga tggcagacgt ggtgaagctt ctgtctgcag tgtgcattgt cggcgaggaa    840
agcatccttg aagaagtgtt agaagccttg acttcagctg agaagaaag aaagattgac     900
agattttttt ccattgtgga aggcctccgg cataactcag tgaacctgca agttgcttgt    960
atgcagctca taaatgctct cgttacatct cctgatgatt tggacttcag gcttcacctc    1020
agaaatgaat ttatgcgttg tggattgaaa gagatattgc caaacttaaa gggcattaag    1080
aatgatggcc tggatataca acttaaagtc tttgatgagc acaagaaga gatttgagt    1140
gagttttttcc atcgccttga agacattaga gctgaacttg atgaagcatc tgatgtttac    1200
agcatgttat gggacacagt taaggaaact cgagcagagg gacatttct ttctattctt     1260
cagcatctcc tgctcattcg caatgatcgt tttataagag agcagtattt caaattaatt    1320
gatgagtgtg tgtcacagat tgtattacat agagatggaa cggaccctga cttcacatac    1380
agaaaaagac tagatttgga cttaagtcag tttgtagatg tttgcataga tcaggccaaa    1440
ctagatgagt gggaagagaa agcatccgaa cattgcaaga aatttgaaaa agagtgtact    1500
gaccaccaag aaacccaggc tcaattgcag aaaagagagg caaagattaa tgagcttcaa    1560
gcagagttac aagcttttaa atcccagttt ggtgccttgc cacctggtac aaaaattcct    1620
ttgcaacctt cagtagaagg tgaagctggc ccttcagccc ttcctcctgc cccaccagca    1680
ctcagtggag gagtgccgcc tcccccaccg ccccctcctc caccaccccc accactccca    1740
ggaatgccaa tgccatttgg tggccctgta ccaccaccac ctcctctggg attcctgggt    1800
gggcaaagct ctattccatt aaacctgcca tttggtttga accaaagaa agaatttaag    1860
cctgaaatca gcatgagaag attgaattgg ttaaagatcg gaccaaatga aatgtctgag    1920
aactgcttct ggatcaaagt aaatgaaaat aagtatgaaa atagggtttt gctttgtaaa    1980
cttgagaaca cttttttgttg ccaagaaaaa gagaaaagga atacaaatga ctttgatgag    2040
aagaaagtta ttaagaagag aatgaaggaa cttaaatttc tagatcctaa aattgctcag    2100
aacctttcaa tcttcctgag ctccttccgg gtgccatatg agaaaatcag gacgatgata    2160
ttggaagtgg atgaaacaca gttgtcagag tccatgattc agaacttaat aaagcacctt    2220
cctgatgagg agcagttgaa gtcattgtcc cagtttagaa gtgactataa cagtttgtgt    2280
gagcctgagc agttcgctgt tgtgatgagc aatgtgaaga gactccggcc acggctcagt    2340
gctattctct ttaagcttca atttgaagag caggtgaaca acatcaaacc tgacatcatg    2400
gctgtcagta ctgcctgcga ggagatcaag aagagcaaag gctttagcaa gttgctggaa    2460
```

```
cttgtgttgc taatgggaaa ctacatgaat gctggctccc ggaatgctca aaccttcgga    2520
tttgacctta gctctctctg taaactgaag gatacaaaat ctgcagatca gaaaaccaca    2580
ctcctccatt tcctggtaga tgtatgtgaa gaaaagcatg ctgacatcct tcactttgtg    2640
gacgatttgg cacatttaga caaagctagc agagtctctg tagaaatgct ggaaaagaac    2700
gtgaagcaga tgggaaggca gcttcaacag cttgagaaga atttggaaac ctttccccct    2760
cctgaggact tgcatgacaa gtttgtgata agatgtcca gcttcgttat cagtgcgaac    2820
gagcagtatg aaaaactctc cacactactg ggcagcatga cacaattgta ccagagtata    2880
atgggctact atgctgtcga catgaagaag gtttccgtgg aagagttttt taatgatctg    2940
aacaacttca gaacttcatt tatgctagca ttaaaggaaa acatcaaaaa acgagaagca    3000
gcagaaaagg agaaacgtgc caggatagcg aaagagcgag cagagaaaga gcgacttgaa    3060
cgccagcaag agaaaaagcg cttactagaa atgaaaactg agggagatga gacaggagtg    3120
atggatagtc tgctggaggc cttgcagtca ggggctgcct ccgcgacag aagaaaaagg    3180
acaccaaagc tgaaagatat tcggcagagt ctcagcccga tgtctcagag gcctgttctc    3240
aaagtttgta accatgaaaa tcagaaaatg cagttgacag aagggtcacg tccacaccac    3300
agtatcaatt gcaactccac caggactcca gtcgccaagg agcttaatta taatctagac    3360
actcatgcgt ctacagggag gatcaaggca gttgagaagg aagcctgtaa tgcagaaagc    3420
aacaaaaaaa aggaaatgga acttcttggc tctgttgcta aaagcgaatc agttcctgaa    3480
gttgaagccc tgctggcaag attacgagct ttataa                              3516
```

<210> 10
<211> 27
<212> PRT
<213> Artificial
<220>
<223> Fragment from mDia2

<400> 10

Asp Glu Thr Gly Val Met Asp Asx Leu Leu Glu Ala Leu Gln Ser Gly
1               5                   10                  15

Ala Ala Phe Arg Asp Arg Arg Lys Arg Thr Pro
            20                  25

<210> 11
<211> 31
<212> PRT
<213> Artificial
<220>
<223> Fragment from Diaphanous
<400> 11

Thr Gln Glu Gly Val Met Asp Ser Leu Leu Glu Ala Leu Gln Thr Gly
1               5                   10                  15

Ser Ala Phe Gly Gln Arg Asn Arg Gln Ala Arg Arg Gln Arg Asn
            20                  25                  30

```
<210>  12
<211>  22
<212>  PRT
<213>  Artificial

<220>
<223>  Fragment from WASP

<400>  12

Gly Arg Gly Ala Leu Leu Asp Gln Ile Arg Gln Gly Ile Gln Leu Asn
1               5                   10                  15

Lys Thr Pro Gly Ala Pro
            20

<210>  13
<211>  22
<212>  PRT
<213>  Artificial

<220>
<223>  Fragment from N-WASP

<400>  13

Gly Arg Asp Ala Leu Leu Asp Gln Ile Arg Gln Gly Ile Gln Leu Lys
1               5                   10                  15

Ser Val Ala Asp Gly Gln
            20

<210>  14
<211>  20
<212>  PRT
<213>  Artificial

<220>
<223>  Fragment from WIP

<400>  14

Gly Arg Asn Ala Leu Leu Ser Asp Ile Ser Lys Gly Lys Lys Leu Lys
1               5                   10                  15

Lys Thr Val Asp
            20

<210>  15
<211>  20
<212>  PRT
<213>  Artificial

<220>
<223>  Fragment from Cofilin

<400>  15

Gly Arg Asp Ala Leu Leu Gly Asp Ile Arg Lys Gly Met Lys Leu Lys
1               5                   10                  15

Lys Ala Glu Thr
            20
```

```
<210> 16
<211> 23
<212> PRT
<213> Artificial

<220>
<223> Fragment from Scar1

<400> 16

Ala Arg Ser Val Leu Leu Glu Ala Ile Arg Lys Gly Ile Gln Leu Arg
1               5                   10                  15

Lys Val Glu Glu Gln Arg Glu
            20

<210> 17
<211> 25
<212> PRT
<213> Artificial

<220>
<223> Fragment from mDia2

<400> 17

Val Met Asp Ser Leu Leu Glu Ala Leu Gln Ser Gly Ala Ala Phe Arg
1               5                   10                  15

Asp Arg Arg Lys Arg Thr Pro Lys Leu
            20                  25

<210> 18
<211> 23
<212> PRT
<213> Artificial

<220>
<223> Fragment from mDia3

<400> 18

Val Met Asp Asn Leu Leu Glu Ala Leu Gln Ser Gly Ala Ala Phe Arg
1               5                   10                  15

Asp Arg Arg Lys Arg Ile Pro
            20

<210> 19
<211> 21
<212> PRT
<213> Artificial

<220>
<223> Fragment from mDia1

<400> 19

Val Met Asp Ser Leu Leu Glu Ala Leu Gln Ser Gly Ala Ala Phe Arg
1               5                   10                  15

Arg Lys Arg Gly Pro
            20
```

```
<210>  20
<211>  26
<212>  PRT
<213>  Artificial

<220>
<223>  Fragment from Diaphanous

<400>  20

Val Met Asp Ser Leu Leu Glu Ala Leu Gln Thr Gly Ser Ala Phe Gly
1               5                   10                  15

Gln Arg Asn Arg Gln Ala Arg Arg Gln Arg
            20                  25

<210>  21
<211>  26
<212>  PRT
<213>  Artificial

<220>
<223>  Fragment from Bnilp

<400>  21

Val Met Asp Lys Leu Leu Glu Gln Leu Lys Asn Ala Gly Pro Ala Lys
1               5                   10                  15

Ser Asp Pro Ser Ser Ala Arg Lys Arg Ala
            20                  25

<210>  22
<211>  26
<212>  PRT
<213>  Artificial

<220>
<223>  Fragment from SepA

<400>  22

Ala Met Asp Ser Leu Leu Glu Lys Leu Arg Ala Ala Ala Pro Gln Ala
1               5                   10                  15

Lys Asp Gln Arg Asp Arg Arg Arg Arg Ala
            20                  25

<210>  23
<211>  11
<212>  PRT
<213>  Artificial

<220>
<223>  Fragment from WASP

<400>  23

His Val Met Gln Lys Arg Ser Arg Ala Ile His
1               5                   10
```

```
<210> 24
<211> 11
<212> PRT
<213> Artificial

<220>
<223> Fragment from ActA

<400> 24

Ala Glu Ile Lys Lys Arg Arg Lys Ala Ile Ala
1               5                   10

<210> 25
<211> 11
<212> PRT
<213> Artificial

<220>
<223> Fragment from Cofilin

<400> 25

Glu Glu Val Lys Lys Arg Lys Lys Ala Val Leu
1               5                   10

<210> 26
<211> 11
<212> PRT
<213> Artificial

<220>
<223> Fragment from mDia2

<400> 26
Ala Phe Arg Asp Arg Arg Lys Arg Thr Pro Lys
1               5                   10

<210> 27
<211> 31
<212> PRT
<213> Artificial

<220>
<223> Fragment from mDia2

<400> 27

Asp Glu Thr Gly Val Met Asp Ser Leu Leu Glu Ala Leu Gln Ser Gly
1               5                   10                  15

Ala Ala Phe Arg Asp Arg Arg Lys Arg Thr Pro Lys Leu Lys Asp
                20                  25                  30
```
--.

Column 56

Claim 7, line 42 replace "$C_1C_{20}$" with --$C_1$-$C_{20}$--.